United States Patent
Long et al.

(10) Patent No.: US 9,752,198 B2
(45) Date of Patent: Sep. 5, 2017

(54) CORN EVENT MIR162

(71) Applicant: Syngenta Participations AG, Basel (CH)

(72) Inventors: Nykoll Long, Holly Springs, NC (US); Jeffrey Bottoms, Durham, NC (US); Moez Rajabali Meghji, St. Louis, MO (US); Hope Hart, Durham, NC (US); Qiudeng Que, Durham, NC (US); Derrick Pulliam, Durham, NC (US)

(73) Assignee: Syngenta Participations AG, Basel (CH)

( * ) Notice: Subject to any disclaimer, the term of this patent is extended or adjusted under 35 U.S.C. 154(b) by 771 days.

(21) Appl. No.: 13/939,954

(22) Filed: Jul. 11, 2013

(65) Prior Publication Data

US 2014/0162272 A1    Jun. 12, 2014

Related U.S. Application Data

(62) Division of application No. 13/534,202, filed on Jun. 27, 2012, now Pat. No. 8,618,272, which is a division of application No. 12/301,824, filed on Jul. 15, 2009, now Pat. No. 8,232,456.

(60) Provisional application No. 60/810,499, filed on Jun. 3, 2006.

(51) Int. Cl.
    *C12Q 1/68* (2006.01)
    *C07K 14/415* (2006.01)
    *C12N 15/82* (2006.01)

(52) U.S. Cl.
    CPC .......... *C12Q 1/6895* (2013.01); *C07K 14/415* (2013.01); *C12N 15/8286* (2013.01); *C12Q 2600/13* (2013.01)

(58) Field of Classification Search
    USPC .............................. 435/6.12, 91.2; 536/24.33
    See application file for complete search history.

(56) References Cited

U.S. PATENT DOCUMENTS

| | | | |
|---|---|---|---|
| 4,683,195 A * | 7/1987 | Mullis | C12Q 1/6827 435/6.1 |
| 4,808,426 A | 2/1989 | Strop et al. | |
| 5,849,320 A | 12/1998 | Turnblad et al. | |
| 5,876,739 A | 3/1999 | Turnblad et al. | |
| 5,877,012 A | 3/1999 | Estruch et al. | |
| 6,429,360 B1 | 8/2002 | Estruch et al. | |
| 6,551,962 B1 | 4/2003 | Pershing et al. | |
| 7,361,813 B2 | 4/2008 | Steiner et al. | |
| 7,897,748 B2 | 3/2011 | Steiner et al. | |
| 8,232,456 B2 | 7/2012 | Long et al. | |
| 8,354,519 B2 | 1/2013 | Steiner et al. | |

FOREIGN PATENT DOCUMENTS

| | | |
|---|---|---|
| EP | WO 98/44137 A2 | 10/1998 |
| WO | WO 03/052073 A2 | 6/2003 |
| WO | WO 03/052073 A3 | 7/2005 |

OTHER PUBLICATIONS

Lowe et al. (Nucleic acid research, 1990, vol. 18(7), p. 1757-1761).*
The nucleic acid sequence search reports AC: ACF06316 & ACF06320.*
Syngenta Participations AG, International Application Ser. No. PCT/US07/012301, International Search Report, dated Sep. 30, 2008.
Syngenta Participations AG, International Application Ser. No. PCT/US07/012301, Written Opinion, dated Sep. 30, 2008.

* cited by examiner

*Primary Examiner* — David Thomas
(74) *Attorney, Agent, or Firm* — Yoshimi D. Barron

(57) ABSTRACT

A novel transgenic corn event designated MIR162 is disclosed. The invention relates to nucleic acids that are unique to event MIR162 and to methods for detecting the presence of the MIR162 event based on DNA sequences of the recombinant constructs inserted into the corn genome that resulted in the MIR162 event and of genomic sequences flanking the insertion site. The invention further relates to corn plants comprising the transgenic genotype of MIR162 and to methods for producing a corn plant by crossing a corn plant comprising the MIR162 genotype with itself or another corn variety. Seeds of corn plants comprising the MIR162 genotype are also objects of the present invention. The invention also relates to methods of controlling insects using MIR162 corn plants.

5 Claims, No Drawings

CORN EVENT MIR162

This application is a divisional of U.S. patent application Ser. No. 13/534,202, filed Jun. 27, 2012, which is a divisional of U.S. patent application Ser. No. 12/301,824, filed Jul. 15, 2009, now U.S. Pat. No. 8,232,456, which is a §371 of PCT/US2007/012301, filed May 24, 2007, and published Dec. 13, 2007 as WO 2007/142840, which claims priority from U.S. Provisional Application No. 60/810,499, filed Jun. 3, 2006. These documents are incorporated herein by reference in their entirety.

BACKGROUND

The present invention relates generally to the field of plant molecular biology, plant transformation, and plant breeding. More specifically, the invention relates to insect resistant transgenic corn plants comprising a novel transgenic genotype and to methods of detecting the presence of nucleic acids that are unique to the transgenic corn plants in a sample and compositions thereof.

Plant pests are a major factor in the loss of the world's important agricultural crops. About $8 billion are lost every year in the U.S. alone due to infestations of non-mammalian pests including insects. In addition to losses in field crops, insect pests are also a burden to vegetable and fruit growers, to producers of ornamental flowers, and to home gardeners.

Insect pests are mainly controlled by intensive applications of chemical pesticides, which are active through inhibition of insect growth, prevention of insect feeding or reproduction, or cause death. Good insect control can thus be reached, but these chemicals can sometimes also affect other, beneficial insects. Another problem resulting from the wide use of chemical pesticides is the appearance of resistant insect varieties. This has been partially alleviated by various resistance management practices, but there is an increasing need for alternative pest control agents. Biological pest control agents, such as *Bacillus thuringiensis* (Bt) strains expressing pesticidal toxins like δ-endotoxins, have also been applied to crop plants with satisfactory results, offering an alternative or compliment to chemical pesticides. The genes coding for some of these δ-endotoxins have been isolated and their expression in heterologous hosts have been shown to provide another tool for the control of economically important insect pests. In particular, the expression of Bt δ-endotoxins has provided efficient protection against selected insect pests, and transgenic plants expressing such toxins have been commercialized, allowing farmers to reduce applications of chemical insect control agents.

Another family of insecticidal proteins produced by *Bacillus* species during the vegetative stage of growth (vegetative insecticidal proteins (Vip)) has also been identified. U.S. Pat. Nos. 5,877,012, 6,107,279, and 6,137,033, herein incorporated by reference, describe a new class of insecticidal proteins called Vip3. Other disclosures, including WO 98/18932, WO 98/33991, WO 98/00546, and WO 99/57282, have also now identified homologues of the Vip3 class of proteins. Vip3 coding sequences encode approximately 88 kDa proteins that possess insecticidal activity against a wide spectrum of lepidopteran pests, including, but not limited to, black cutworm (BCW, *Agrotis ipsilon*), fall armyworm (FAW, *Spodoptera frugiperda*), tobacco budworm (TBW, *Heliothis virescens*), sugarcane borer, (SCB, *Diatraea saccharalis*), lesser cornstalk borer (LCB, *Elasmopalpus lignosellus*), and corn earworm (CEW, *Helicoverpa zea*), and when expressed in transgenic plants, for example corn (*Zea mays*), confer protection to the plant from insect feeding damage.

Present plant transformation methods generally lead to the random integration of transgenes like vip3 into a host-plant genome. This random insertion of introduced DNA into the plant's genome can be lethal if the foreign DNA happens to insert into, and thus mutate, a critically important native gene. In addition, even if a random insertion event does not impair the functioning of a host cell gene, the expression of an inserted foreign gene may be influenced by "position effects" caused by the surrounding genomic DNA. In some cases, the gene is inserted into sites where the position effects are strong enough to prevent the synthesis of an effective amount of product from the introduced gene. For example, it has been observed in plants that there may be wide variations in levels of expression of a heterologous gene introduced into a plant's chromosome among individually selected events. There may also be differences in spatial or temporal patterns of expression, for example, differences in the relative expression of a transgene in various plant tissues, that may not correspond to the patterns expected from transcriptional regulatory elements present in the introduced gene construct. In other instances, overproduction of the gene product has deleterious effects on the cell. Because of these potential problems, it is common to produce hundreds of different events and screen those events for a single event that has desired transgene expression patterns and levels for commercial purposes. However, once a commercially viable site within the plant's genome is identified it would be advantageous to target genes of interest to that non-detrimental site.

Several methods for the targeted insertion of a nucleotide sequence of interest into a specific chromosomal site within a plant cell have been described. Site-specific recombination systems have been identified in several prokaryotic and lower eukaryotic organisms. Such systems typically comprise one or more proteins that recognize two copies of a specific nucleotide sequence, cleave and ligate those nucleotide sequences, and thereby provide a precise, site-specific exchange of genetic information. Several site-specific recombinases are known in the art. These include, but are not limited to, e.g., the bacteriophage P1 Cre/lox system (Austin et al. (1981) Cell 25: 729-736), the R/RS recombinase system from the pSRi plasmid of the yeast *Zygosaccharomyces rouxii* (Araki et al. (1985) J. Mol. Biol. 182: 191-203), the Gin/gix system of phage Mu (Maeser and Kahlmann (1991) Mol. Gen. Genet. 230: 170-176), the FLP/FRT recombinase system from the 2 .mu.m plasmid of the yeast *Saccharomyces cerevisiae* (Broach et al. (1982) Cell 29: 227-234), and the Int recombinase from bacteriophage Lambda (Landy (1989) Annu. Rev. Biochem. 58: 912-949; Landy (1993) Curr. Opin. Genet. Dev. 3: 699-707; Lorbach et al. (2000) J. Mol. Biol. 296: 1175-1181; and WO 01/16345). One particularly useful site-specific targeting approach, disclosed in US Patent Application Publication No. 2006/0130179, herein incorporated by reference, uses lambda integrase mediated recombination. The method comprises introducing into a plant cell a target nucleotide sequence comprising a first Integrase Recognition Site; introducing into the plant cell a donor nucleotide sequence comprising a second Integrase Recognition Site; and introducing into the plant cell an Integrase or Integrase complex. Another useful site-specific targeting approach is disclosed in US Patent Application Publication No. 2006/0253918, herein incorporated by reference, which uses homologous recombination to integrate one or more genes (gene stacking) at specific locations in the genome.

An event that has desired levels or patterns of transgene expression is useful for introgressing the transgene into other genetic backgrounds by sexual out-crossing using conventional breeding methods. Progeny of such crosses maintain the transgene expression characteristics of the original transformant. This strategy is used to ensure reliable gene expression in a number of varieties that are well adapted to local growing conditions. It would also be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example. It is possible to detect the presence of a transgene by any well-known nucleic acid detection method including but not limited to thermal amplification (polymerase chain reaction (PCR)) using polynucleotide primers or DNA hybridization using nucleic acid probes. Typically, for the sake of simplicity and uniformity of reagents and methodologies for use in detecting a particular DNA construct that has been used for transforming various plant varieties, these detection methods generally focus on frequently used genetic elements, for example, promoters, terminators, and marker genes, because for many DNA constructs, the coding sequence region is interchangeable. As a result, such methods may not be useful for discriminating between constructs that differ only with reference to the coding sequence. In addition, such methods may not be useful for discriminating between different events, particularly those produced using the same DNA construct unless the sequence of chromosomal DNA adjacent to the inserted heterologous DNA ("flanking DNA") is known.

For the foregoing reasons, there is a need for insect resistant transgenic corn events comprising novel nucleic acid sequences which are unique to the transgenic corn event, useful for identifying the transgenic corn event and for detecting nucleic acids from the transgenic corn event in a biological sample, as well as kits comprising the reagents necessary for use in detecting these nucleic acids in a biological sample. There is a further need to provide specific target sites within the maize genome to allow for targeting and control of insertion of nucleotide sequences to be integrated into the corn genome.

SUMMARY

The present invention relates to a transformed corn (*Zea mays*) event, designated MIR162 comprising a novel transgenic genotype that comprises a vip3Aa20 coding sequence, which is unique to event MIR162. The vip3Aa20 coding sequence encodes a Vip3Aa20 insecticidal protein that confers insect resistance to MIR162 corn plants. The MIR162 event also comprises a pmi coding sequence encoding a PMI protein that confers upon corn cells the ability to utilize mannose as a carbon source. In addition to the vip3A20 coding sequence, the present invention also provides other nucleic acids that are unique to MIR162. The invention also provides transgenic corn plants comprising the nucleic acids unique to MIR162, seed from the transgenic corn plants, and to methods for producing a transgenic corn plant comprising the unique nucleic acids of the invention by crossing a corn inbred comprising the nucleic acids unique to MIR162 with itself or another corn line of a different genotype. An example of seed, and hence corn plants grown from the seed, comprising nucleic acids unique to MIR162 was deposited at the American Type Culture Collection as accession No. PTA-8166. The transgenic corn plants of the invention may have essentially all of the morphological and physiological characteristics of corresponding isogenic non-transgenic corn plants in addition to those conferred upon the corn plants by the novel genotype of the invention. Biological samples and extracts from MIR162 corn plants, tissues and seeds are also provided by the present invention. The present invention also provides compositions and methods for detecting the presence of nucleic acids unique to MIR162 in biological samples based on the DNA sequence of the recombinant expression cassettes inserted into the corn genome that resulted in the MIR162 event and of genomic sequences flanking the insertion site. The present invention also provides a non-detrimental insertion target site on a maize chromosome useful for inserting genes of interest to a specific location on the chromosome and to methods of altering a maize genome by inserting heterologous nucleic acids at the disclosed insertion site or in the vicinity of the disclosed insertion site. The MIR162 event can be further characterized by analyzing expression levels of the Vip3Aa20 and PMI proteins as well as by testing MIR162 for efficacy against lepidopteran insect pests. The present invention also provides methods of producing transgenic corn plants resistant to a broader spectrum of insect pests by stacking the Vip3Aa20 insect resistant trait with insect resistance traits different than Vip3Aa20.

The foregoing and other aspects of the invention will become more apparent from the following detailed description.

DESCRIPTION OF THE SEQUENCES IN THE SEQUENCE LISTING

SEQ ID NO: 1 is the Vip3Aa20 coding sequence in MIR162.

SEQ ID NO: 2 is the Vip3Aa20 amino acid sequence.

SEQ ID NO: 3 is the sequence of plasmid pNOV1300.

SEQ ID Nos: 4-12 are primers and probes useful in a TAQMAN assay.

SEQ ID NO: 13 is the sequence of a vip3Aa20 probe.

SEQ ID NO: 14 is the sequence of a pmi probe.

SEQ ID Nos: 15-37 are primers useful in the present invention.

SEQ ID No: 38 is the sequence of a vip3Aa20 amplicon.

SEQ ID Nos: 39-40 are primers useful in the present invention.

SEQ ID No: 41 is the sequence of the CJ134/179 5' amplicon.

SEQ ID Nos: 42-43 are primers useful in the present invention.

SEQ ID NO: 44 is a vip3Aa20 3' amplicon.

SEQ ID NO: 45 is the 5' genome-insert junction.

SEQ ID NO: 46 is corn genome sequence flanking 5' to insert.

SEQ ID NO: 47 is the 3' insert-genome junction.

SEQ ID NO: 48 is corn genome flanking 3' to insert.

SEQ ID NO: 49 is the MIR162 insert and flanking sequences.

SEQ ID Nos. 50-54 are primers useful in the present invention.

SEQ ID NO: 55 is a 5' PCR amplicon

SEQ ID Nos. 56-58 are primers useful in the present invention.

SEQ ID NO: 59 is a 3' PCR amplicon.

SEQ ID Nos. 60-105 are primers useful in the present invention.

SEQ ID NO: 106 is the sequence of the region of maize chromosome 5 comprising the disclosed chromosomal target site.

SEQ ID NO: 107 is the maize genomic sequence that was displaced by the insertion of heterologous DNA in MIR162.

DETAILED DESCRIPTION

The following definitions and methods are provided to better define the present invention and to guide those of ordinary skill in the art in the practice of the present invention. Unless otherwise noted, terms used herein are to be understood according to conventional usage by those of ordinary skill in the relevant art. Definitions of common terms in molecular biology may also be found in Rieger et al., Glossary of Genetics: Classical and Molecular, 5$^{th}$ edition, Springer-Verlag: New York, 1994. The nomenclature for DNA bases and amino acids as set forth in 37 C.F.R. §1.822 is used herein.

As used herein, the term "amplified" means the construction of multiple copies of a nucleic acid molecule or multiple copies complementary to the nucleic acid molecule using at least one of the nucleic acid molecules as a template. Amplification systems include, but not limited to the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology Principles and Applications*, D. H. Persing et al., Ed., American Society for Microbiology, Washington, D.C. (1993). The product of amplification is termed an amplicon.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

As used herein, the term "corn" means *Zea mays* or maize and includes all plant varieties that can be bred with corn, including wild maize species.

"Detection kit" as used herein refers to a kit of parts useful in detecting the presence or absence of DNA unique to MIR162 plants in a sample, wherein the kit comprises nucleic acid probes and/or primers of the present invention, which hybridize specifically under high stringency conditions to a target DNA sequence, and other materials necessary to enable nucleic acid hybridization or amplification methods.

As used herein the term transgenic "event" refers to a recombinant plant produced by transformation and regeneration of a plant cell or tissue with heterologous DNA, for example, an expression cassette that includes a gene of interest. The term "event" refers to the original transformant and/or progeny of the transformant that include the heterologous DNA. The term "event" also refers to progeny produced by a sexual outcross between the transformant and another corn line. Even after repeated backcrossing to a recurrent parent, the inserted DNA and the flanking DNA from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA. Normally, transformation of plant tissue produces multiple events, each of which represent insertion of a DNA construct into a different location in the genome of a plant cell. Based on the expression of the transgene or other desirable characteristics, a particular event is selected. Thus, "event MIR162", "MIR162" or "MIR162 event" may be used interchangeably.

An insect resistant MIR162 corn plant can be bred by first sexually crossing a first parental corn plant consisting of a corn plant grown from a transgenic MIR162 corn plant, such as a MIR162 corn plant grown from the seed deposited at the ATCC under accession No. PTA-6188, and progeny thereof derived from transformation with the expression cassettes of the embodiments of the present invention that confers insect resistance, and a second parental corn plant that lacks insect resistance, thereby producing a plurality of first progeny plants; and then selecting a first progeny plant that is resistant to insects; and selfing the first progeny plant, thereby producing a plurality of second progeny plants; and then selecting from the second progeny plants an insect resistant plant. These steps can further include the backcrossing of the first insect resistant progeny plant or the second insect resistant progeny plant to the second parental corn plant or a third parental corn plant, thereby producing a corn plant that is resistant to insects.

"Expression cassette" as used herein means a nucleic acid molecule capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation process known in the art. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

A "gene" is a defined region that is located within a genome and that, besides the aforementioned coding sequence, may comprise other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability.

"Genotype" as used herein is the genetic material inherited from parent corn plants not all of which is necessarily expressed in the descendant corn plants. The MIR162 genotype refers to the heterologous genetic material transformed into the genome of a plant as well as the genetic material flanking the inserted sequence.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Operably-linked" refers to the association of nucleic acid sequences on a single nucleic acid fragment so that the function of one affects the function of the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

"Primers" as used herein are isolated nucleic acids that are annealed to a complimentary target DNA strand by nucleic acid hybridization to form a hybrid between the primer and the target DNA strand, and then extended along the target DNA strand by a polymerase, such as DNA polymerase. Primer pairs or sets can be used for amplification of a nucleic acid molecule, for example, by the polymerase chain reaction (PCR) or other conventional nucleic-acid amplification methods.

A "probe" is an isolated nucleic acid to which is attached a conventional detectable label or reporter molecule, such as a radioactive isotope, ligand, chemiluminescent agent, or enzyme. Such a probe is complementary to a strand of a target nucleic acid, in the case of the present invention, to a strand of genomic DNA from corn event MIR162. The DNA of MIR162 can be from a corn plant or from a sample that includes DNA from MIR162. Probes according to the present invention include not only deoxyribonucleic or ribonucleic acids but also polyamides and other probe materials that bind specifically to a target DNA sequence and can be used to detect the presence of that target DNA sequence.

Primers and probes are generally between 10 and 15 nucleotides or more in length. Primers and probes can also be at least 20 nucleotides or more in length, or at least 25 nucleotides or more, or at least 30 nucleotides or more in length. Such primers and probes hybridize specifically to a target sequence under high stringency hybridization conditions. Primers and probes according to the present invention may have complete sequence complementarity with the target sequence, although probes differing from the target sequence and which retain the ability to hybridize to target sequences may be designed by conventional methods.

As used herein gene or trait "stacking" is combining desired traits into one transgenic line. Plant breeders stack transgenic traits by making crosses between parents that each have a desired trait and then identifying offspring that have both of these desired traits. Another way to stack genes is by transferring two or more genes into the cell nucleus of a plant at the same time during transformation. Another way to stack genes is by re-transforming a transgenic plant with another gene of interest. For example, gene stacking can be used to combine two different insect resistance traits, an insect resistance trait and a disease resistance trait, or a herbicide resistance trait. The use of a selectable marker in addition to a gene of interest would also be considered gene stacking.

"Stringent conditions" or "stringent hybridization conditions" include reference to conditions under which a probe will hybridize to its target sequence, to a detectably greater degree than to other sequences. Stringent conditions are target-sequence-dependent and will differ depending on the structure of the polynucleotide. By controlling the stringency of the hybridization and/or wash conditions, target sequences can be identified which are 100% complementary to the probe (homologous probing). Alternatively, stringency conditions can be adjusted to allow some mismatching in sequences so that lower degrees of similarity are detected (heterologous probing). Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes*, Part I, Chapter 2 "Overview of principles of hybridization and the strategy of nucleic acid probe assays", Elsevier: New York; and *Current Protocols in Molecular Biology*, Chapter 2, Ausubel et al., Eds., Greene Publishing and Wiley-Interscience: New York (1995), and also Sambrook et al. (2001) *Molecular Cloning: A Laboratory Manual* ($5^{th}$ Ed. Cols Spring Harbor Laboratory, Cold Spring Harbor, N.Y.).

Specificity is typically the function of post-hybridization washes, the critical factors being the ionic strength and temperature of the final wash solution. Generally, high stringency hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, under high stringency conditions a probe will hybridize to its target subsequence, but to no other sequences.

An example of high stringency hybridization conditions for hybridization of complementary nucleic acids which have more than 100 complementary residues on a filter in a Southern or northern blot is 50% formamide with 1 mg of heparin at 42° C., with the hybridization being carried out overnight. An example of very high stringency wash conditions is 0.15M NaCl at 72° C. for about 15 minutes. An example of high stringency wash conditions is a 0.2×SSC wash at 65° C. for 15 minutes (see, Sambrook, infra, for a description of SSC buffer).

Exemplary hybridization conditions for the present invention include hybridization in 7% SDS, 0.25 M $NaPO_4$ pH 7.2 at 67° C. overnight, followed by two washings in 5% SDS, 0.20 M $NaPO_4$ pH7.2 at 65° C. for 30 minutes each wash, and two washings in 1% SDS, 0.20 M $NaPO_4$ pH7.2 at 65° C. for 30 minutes each wash. An exemplary medium stringency wash for a duplex of, e.g., more than 100 nucleotides, is 1×SSC at 45° C. for 15 minutes. An exemplary low stringency wash for a duplex of, e.g., more than 100 nucleotides, is 4-6×SSC at 40° C. for 15 minutes.

For probes of about 10 to 50 nucleotides, high stringency conditions typically involve salt concentrations of less than about 1.0 M Na ion, typically about 0.01 to 1.0 M Na ion concentration (or other salts) at pH 7.0 to 8.3, and the temperature is typically at least about 30° C. High stringency conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under high stringency conditions are still substantially identical if the proteins that they encode are substantially identical. This occurs, e.g., when a copy of a nucleic acid is created using the maximum codon degeneracy permitted by the genetic code.

The following are exemplary sets of hybridization/wash conditions that may be used to hybridize nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C. The sequences of the present invention may be detected using all the above conditions. For the purposes of defining the invention, the high stringency conditions are used.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule. As used herein, "transgenic" refers to a plant, plant cell, or multitude of structured or unstructured plant cells having integrated, via well known techniques of genetic manipulation and gene insertion, a sequence of nucleic acid representing a gene of interest into the plant genome, and typically into a chromosome of a cell nucleus, mitochondria or other organelle containing chromosomes, at a locus different to, or in a number of copies greater than, that normally present in the native plant or plant cell. Transgenic plants result from the manipulation and insertion of such nucleic acid sequences, as opposed to naturally occurring mutations, to produce a non-naturally occurring plant or a plant with a non-naturally occurring genotype. Techniques for transformation of plants and plant cells are well known in the art and may comprise for example electroporation, microinjection, *Agrobacterium*-mediated transformation, and ballistic transformation.

As used herein, the term "unique" to MIR162 means distinctively characteristic of MIR162. Therefore, nucleic acids unique to event MIR162 are not found in other non-MIR162 corn plants.

The "Vip3" class of proteins comprises, for example, Vip3Aa, Vip3Ab, Vip3Ac, Vip3Ad, Vip3Ae, VipAf, Vip3Ag, Vip3Ba, and Vip3Bb, and their homologues. "Homologue" means that the indicated protein or polypeptide bears a defined relationship to other members of the Vip3 class of proteins. "Vip3Aa20" is a Vip3 homologue unique to event MIR162. It was generated by spontaneous mutations introduced into the maize-optimized vip3Aa19 gene comprised in pNOV1300 (SEQ ID NO: 3) during the plant transformation process.

This invention relates to a genetically improved line of corn that produces an insect control protein, Vip3Aa20, and a phosphomannose isomerase enzyme (PMI) that allows the plant to utilize mannose as a carbon source. The invention is particularly drawn to a transgenic corn event designated MIR162 comprising a novel genotype, as well as to compositions and methods for detecting nucleic acids unique to MIR162 in a biological sample. The invention is further drawn to corn plants comprising the MIR162 genotype, to transgenic seed from the corn plants, and to methods for producing a corn plant comprising the MIR162 genotype by crossing a corn inbred comprising the MIR162 genotype with itself or another corn line. Corn plants comprising the MIR162 genotype of the invention are useful in controlling lepidopteran insect pests including, but not limited to, black cutworm (BCW, *Agrotis ipsilon*), fall armyworm (FAW, *Spodoptera frugiperda*), tobacco budworm (TBW, *Heliothis virescens*), sugarcane borer (SCB, *Diatraea saccharalis*), lesser cornstalk borer (LCB, *Elasmopalpus lignosellus*), corn earworm (CEW, *Helicoverpa zea*), and western bean cutworm (WBCW, *Striacosta albicosta*). The invention is further drawn to a method of protecting transgenic corn from feeding damage whereby stacking the insect resistance trait of MIR162 with a different insect resistance trait in the same transgenic plant results is a corn plant that is protected from feeding damage to a greater degree than the insect resistance traits alone.

In one embodiment, the present invention encompasses an isolated nucleic acid molecule comprising a nucleotide sequence that is unique to event MIR162.

In another embodiment, the present invention encompasses an isolated nucleic acid molecule that links a heterologous DNA molecule inserted into the genome of MIR162 to genome DNA in MIR162 comprising at least 10 or more (for example 15, 20, 25, 50 or more) contiguous nucleotides of the heterologous DNA molecule and at least 10 or more (for example 15, 20, 25, 50, or more) contiguous nucleotides of the genome DNA flanking the point of insertion of the heterologous DNA molecule. Also included are nucleotide sequences that comprise 10 or more nucleotides of contiguous insert sequence from event MIR162 and at least one nucleotide of flanking DNA from event MIR162 adjacent to the insert sequence. Such nucleotide sequences are unique to and diagnostic for event MIR162. Nucleic acid amplification or hybridization of genomic DNA from MIR162 produces an amplicon comprising such unique sequences and is diagnostic for event MIR162. In one aspect of this embodiment, the nucleotide sequence is selected from the group consisting of SEQ ID NO: 1, SEQ ID NO: 38, SEQ ID NO: 41, SEQ ID NO: 45, SEQ ID NO: 47, SEQ ID NO: 49, SEQ ID NO: 55, SEQ ID NO: 59, and the complements thereof.

In another embodiment, the invention encompasses an isolated nucleic acid molecule comprising a nucleotide sequence which comprises at least one junction sequence of event MIR162, wherein a junction sequence spans the junction between a heterologous expression cassette inserted into the corn genome and DNA from the corn genome flanking the insertion site and is diagnostic for the event. In one aspect of this embodiment, the junction sequence is selected from the group consisting of SEQ ID NO: 45, SEQ ID NO: 47, and the complements thereof.

In another embodiment, the present invention encompasses an isolated nucleic acid molecule linking a heterologous DNA molecule to the corn plant genome in event MIR162 comprising a sequence of from about 11 to about 20 contiguous nucleotides selected from the group consisting of SEQ ID NO: 45, SEQ ID NO: 47, and the complements thereof.

In another embodiment, the invention encompasses an isolated nucleic acid molecule comprising a nucleotide sequence selected from the group consisting of SEQ ID NO: 1, SEQ ID NO: 38, SEQ ID NO: 41, SEQ ID NO: 45, SEQ ID NO: 47, SEQ ID NO: 49, SEQ ID NO: 55, SEQ ID NO: 59, and the complements thereof. In one aspect of this embodiment, the isolated nucleic acid molecule is comprised in a corn seed deposited at the American Type Culture Collection under the accession No. PTA-8166, or in plants grown from the seed.

In one embodiment of the present invention, an amplicon comprising a nucleotide sequence unique to event MIR162 is provided. In one aspect of this embodiment, the nucleotide sequence is selected from the group consisting of SEQ ID NO: 1, SEQ ID NO: 38, SEQ ID NO: 41, SEQ ID NO: 45, SEQ ID NO: 47, SEQ ID NO: 49, SEQ ID NO: 55, SEQ ID NO: 59, and the complements thereof.

In another embodiment, the present invention encompasses flanking sequence primers for detecting event MIR162. Such flanking sequence primers comprise a nucleotide sequence of at least 10-15 contiguous nucleotides from the 5' or the 3' flanking sequence. In one aspect of this embodiment, the contiguous nucleotides are selected from nucleotides 1-1088 (inclusive) of SEQ ID NO: 49 (arbitrarily designated herein as the 5' flanking sequence), or the complements thereof. In another aspect of this embodiment, the 5' flanking sequence primers are selected from the group consisting of SEQ ID NO: 36, SEQ ID NO: 39, SEQ ID NO: 53, SEQ ID NOs: 68-80, and the complements thereof. In another aspect of this embodiment, the contiguous nucleotides are selected from nucleotides 9391-10579 (inclusive) of SEQ ID NO: 49 (arbitrarily designated herein as the 3' flanking sequence), or the complements thereof. In yet another aspect of this embodiment, the 3' flanking sequence primers are selected from the group consisting of SEQ ID NO: 58, SEQ ID NOs: 97-105, and the complements thereof.

In still another embodiment, the present invention encompasses a pair of polynucleotide primers comprising a first polynucleotide primer and a second polynucleotide primer that function together in the presence of a event MIR162 DNA template in a sample to produce an amplicon diagnostic for event MIR162. In one aspect of this embodiment, the first primer and/or the second primer is chosen from SEQ ID NO: 1 or the compliment thereof. In another aspect of this embodiment, the first primer and/or the second primer is selected from the group consisting of SEQ ID NOs: 15-35, SEQ ID NO: 37, SEQ ID NO: 42, and the complements thereof. In yet another aspect of this embodiment, the amplicon that is produced by the pair of primers comprises SEQ ID NO: 1, SEQ ID NO: 38, SEQ ID NO: 44, or the complements thereof.

In another embodiment, the present invention encompasses a pair of polynucleotide primers comprising a first polynucleotide primer and a second polynucleotide primer which function together in the presence of a event MIR162 DNA template in a sample to produce an amplicon diagnostic for event MIR162, wherein the first primer is or is complementary to a corn plant genome sequence flanking the point of insertion of a heterologous DNA sequence inserted into the genome of event MIR162, and the second polynucleotide primer sequence is or is complementary to the heterologous DNA sequence inserted into the genome of event MIR162.

In one aspect of this embodiment, the first polynucleotide primer comprises at least 10 contiguous nucleotides from a nucleotide sequence selected from the group consisting of nucleotides 1-1088 of SEQ ID NO: 49, nucleotides 9391-10579 of SEQ ID NO: 49, and the complements thereof. In a further aspect of this embodiment, the first primer is selected from the group consisting of SEQ ID NO: 36, SEQ ID NO: 39, SEQ ID NO: 53, SEQ ID NO: 57, SEQ ID NOs: 68-72, SEQ ID NO: 79, SEQ ID NO: 80, SEQ ID NOs: 97-105, and the complements thereof. In another aspect of this embodiment, the second polynucleotide primer comprises at least 10 contiguous nucleotides from position 1089-9390 of SEQ ID NO: 49, or complements thereof. In still a further aspect of this embodiment, the second polynucleotide primer is selected from the group consisting of SEQ ID NOs: 15-35, SEQ ID NO: 37, SEQ ID NO: 40, SEQ ID NOs: 50-52, SEQ ID NOs: 54, SEQ ID NO: 56, SEQ ID NO: 57, SEQ ID NO: 63, SEQ ID NO: 73, SEQ ID NO: 82, SEQ ID NO: 96, and the complements thereof.

In another aspect of this embodiment, the first polynucleotide primer, which is set forth in SEQ ID NO: 36, and the second polynucleotide primer which is set forth in SEQ ID NO: 37, function together in the presence of a event MIR162 DNA template in a sample to produce an amplicon diagnostic for event MIR162 as described in Example 4. In one embodiment of this aspect, the amplicon comprises the nucleotide sequence set forth in SEQ ID NO: 38.

In yet another aspect of this embodiment, the first polynucleotide primer, which is set forth in SEQ ID NO: 39, and the second polynucleotide primer, which is set forth in SEQ ID NO: 40, function together in the presence of a corn event MIR162 DNA template in a sample to produce an amplicon diagnostic for the corn event MIR162 as described in Example 4. In one embodiment of this aspect, the amplicon comprises the nucleotide sequence set forth in SEQ ID NO: 41.

In another aspect of this embodiment, the first polynucleotide primer, which is set forth in SEQ ID NO: 53, and the second polynucleotide primer, which is set forth in SEQ ID NO: 54, function together in the presence of a corn event MIR162 DNA template in a sample to produce an amplicon diagnostic for the corn event MIR162 as described in Example 5. In one embodiment, the amplicon comprises the nucleotide sequence set forth in SEQ ID NO: 55.

In a still a further aspect of this embodiment, the first polynucleotide primer, which is set forth in SEQ ID NO: 58, and the second polynucleotide primer, which is set forth in SEQ ID NO: 56, function together in the presence of a corn event MIR162 DNA template in a sample to produce an amplicon diagnostic for the corn event MIR162 as described in Example 5. In one embodiment, the amplicon comprises the nucleotide sequence set forth in SEQ ID NO: 59.

Of course, it is well within the skill in the art to obtain additional sequence further out into the genome sequence flanking either end of the inserted heterologous DNA sequences for use as a primer sequence that can be used in such primer pairs for amplifying the sequences that are diagnostic for the MIR162 event. For the purposes of this disclosure, the phrase "further out into the genome sequence flanking either end of the inserted heterologous DNA sequences" refers specifically to a sequential movement away from the ends of the inserted heterologous DNA sequences, the points at which the inserted DNA sequences are adjacent to native genomic DNA sequence, and out into the genomic DNA of the particular chromosome into which the heterologous DNA sequences were inserted. Preferably, a primer sequence corresponding to or complementary to a part of the insert sequence should prime the transcriptional extension of a nascent strand of DNA or RNA toward the nearest flanking sequence junction. Consequently, a primer sequence corresponding to or complementary to a part of the genomic flanking sequence should prime the transcriptional extension of a nascent strand of DNA or RNA toward the nearest flanking sequence junction. A primer sequence can be, or can be complementary to, a heterologous DNA sequence inserted into the chromosome of the plant, or a genomic flanking sequence. One skilled in the art would readily recognize the benefit of whether a primer sequence would need to be, or would need to be complementary to, the sequence as set forth within the inserted heterologous DNA sequence or as set forth SEQ ID NO: 38 depending upon the nature of the product desired to be obtained through the use of the nested set of primers intended for use in amplifying a particular flanking sequence containing the junction between the genomic DNA sequence and the inserted heterologous DNA sequence.

In another embodiment, the present invention encompasses an isolated insecticidal protein comprising SEQ ID NO: 2 and a nucleic acid molecule encoding SEQ ID NO: 2. In one aspect of this embodiment, the nucleic acid molecule is SEQ ID NO: 1. The present invention also encompasses a chimeric gene comprising a heterologous promoter operably linked to the nucleic acid molecule, and to recombinant vectors and host cells comprising the chimeric gene.

In yet another embodiment, the present invention encompasses a method of detecting the presence of a nucleic acid molecule that is unique to event MIR162 in a sample comprising corn nucleic acids, wherein the method comprises: (a) contacting the sample with a pair of polynucleotide primers that, when used in a nucleic acid amplification reaction with genomic DNA from event MIR162 produces an amplicon that is diagnostic for event MIR162; (b) performing a nucleic acid amplification reaction, thereby producing the amplicon; and (c) detecting the amplicon. In one aspect of this embodiment, the amplicon comprises a nucleotide sequence selected from the group consisting of SEQ ID NO: 1, SEQ ID NO: 38, SEQ ID NO: 41, SEQ ID NO: 45, SEQ ID NO: 47, SEQ ID NO: 49, SEQ ID NO: 55, SEQ ID NO: 59, and the compliments thereof.

In another embodiment, the present invention encompasses a method of detecting the presence of a nucleic acid molecule that is unique to event MIR162 in a sample comprising corn nucleic acids, wherein the method comprises: (a) contacting the sample with a probe that hybridizes under high stringency conditions with genomic DNA from event MIR162 and does not hybridize under high stringency conditions with DNA from a control corn plant; (b) subjecting the sample and probe to high stringency hybridization conditions; and (c) detecting hybridization of the probe to the DNA. Detection can be by any means well known in the art including fluorescent, chemiluminescent, radiological, immunological, and the like. In the case in which hybridization is intended to be used as a means for amplification of a particular sequence to produce an amplicon which is diagnostic for the MIR162 event, the production and detection by any means well known in the art of the amplicon is intended to be indicative of the intended hybridization to the target sequence where one probe or primer is utilized, or sequences where two or more probes or primers are utilized. The term "biological sample" is intended to comprise a sample that contains or is suspected of containing a nucleic acid comprising from between five and ten nucleotides either side of the point at which one or the other of the two terminal ends of the inserted heterologous DNA sequence contacts the genomic DNA sequence within the chromosome into which the heterologous DNA sequence was inserted, herein also known as the junction sequences. In addition, the junction sequence comprises as little as two nucleotides: those being the first nucleotide within the flanking genomic DNA adjacent to and covalently linked to the first nucleotide within the inserted heterologous DNA sequence. In one aspect of this embodiment, the probe comprises a nucleotide sequence selected from the group consisting of SEQ ID NO: 1, SEQ ID NO: 38, SEQ ID NO: 41, SEQ ID NO: 45, SEQ ID NO: 47, SEQ ID NO: 49, SEQ ID NO: 55, SEQ ID NO: 59, and the complements thereof.

In yet another embodiment, the present invention encompasses a kit for the detection of nucleic acids that are unique to event MIR162 in biological sample. The kit includes at least one nucleic acid molecule of sufficient length of contiguous polynucleotides to function as a primer or probe in a nucleic acid detection method, and which upon amplification of or hybridization to a target nucleic acid sequence in a sample followed by detection of the amplicon or hybridization to the target sequence, are diagnostic for the presence of nucleic acid sequences unique to event MIR162 in the sample. The kit further includes other materials necessary to enable nucleic acid hybridization or amplification methods. In one aspect of this embodiment, a nucleic acid molecule contained in the kit comprises a nucleotide sequence from SEQ ID NO: 1 or SEQ ID NO: 49. In another aspect of this embodiment, the nucleic acid molecule is a primer selected from the group consisting of SEQ ID NOs: 15-37, SEQ ID NO: 39, SEQ ID NO: 40, SEQ ID NO: 42, SEQ ID NO: 43, SEQ ID NOs: 50-54, SEQ ID NOs: 56-58, SEQ ID NOs: 60-105, and the complements thereof. In yet another aspect of this embodiment, the amplicon comprises SEQ ID NO: 1, SEQ ID NO: 38, SEQ ID NO: 41, SEQ ID NO: 45, SEQ ID NO: 47, SEQ ID NO: 49, SEQ ID NO: 55, SEQ ID NO: 59, or the complements thereof. A variety of detection methods can be used including, but not limited to TAQMAN (Perkin Elmer), thermal amplification, ligase chain reaction, southern hybridization, ELISA methods, and colorimetric and fluorescent detection methods. In particular the present invention provides for kits for detecting the presence of the target sequence, i.e., at least the vip3Aa20 sequence or a junction sequence, in a sample containing genomic nucleic acid from MIR162. The kit is comprised of at least one polynucleotide capable of binding to the target site or substantially adjacent to the target site and at least one means for detecting the binding of the polynucleotide to the target site. The detecting means can be fluorescent, chemiluminescent, colorimetric, or isotopic and can be coupled at least with immunological methods for detecting the binding. A kit is also envisioned which can detect the presence of the target site in a sample, i.e., at least the vip3Aa20 sequence or a junction sequence of MIR162, taking advantage of two or more polynucleotide sequences which together are capable of binding to nucleotide sequences adjacent to or within about 100 base pairs, or within about 200 base pairs, or within about 500 base pairs or within about 1000 base pairs of the target sequence and which can be extended toward each other to form an amplicon which contains at least the target site.

In another embodiment, the present invention encompasses a method of detecting Vip3Aa20 protein in a biological sample, the method comprising: (a) extracting protein from event MIR162 tissue; (b) assaying the extracted protein using an immunological method comprising antibody specific for the Vip3Aa20 protein produced by the MIR162 event; and (c) detecting the binding of said antibody to the Vip3Aa20 protein.

In yet another embodiment, the present invention encompasses a biological sample derived from a event MIR162 corn plant, tissue, or seed, wherein the sample comprises a nucleotide sequence which is or is complementary to a sequence that is unique to event MIR162, and wherein the sequence is detectable in the sample using a nucleic acid amplification or nucleic acid hybridization method. In one aspect of this embodiment, the nucleotide sequence is or is complementary to SEQ ID NO: 1, SEQ ID NO: 38, SEQ ID NO: 41, SEQ ID NO: 45, SEQ ID NO: 47, SEQ ID NO: 49, SEQ ID NO: 55, or SEQ ID NO: 59. In another aspect of this embodiment, the sample is selected from the group consisting of corn flour, corn meal, corn syrup, corn oil, cornstarch, and cereals manufactured in whole or in part to contain corn by-products.

In another embodiment, the present invention encompasses an extract of a biological sample derived from a MIR162 corn plant, tissue, or seed comprising a nucleotide sequence which is or is complementary to a sequence that is unique to MIR162. In one aspect of this embodiment, the sequence is detectable in the extract using a nucleic acid amplification or nucleic acid hybridization method. In another aspect of this embodiment, the sequence is or is complementary to SEQ ID NO: 1, SEQ ID NO: 38, SEQ ID NO: 41, SEQ ID NO: 45, SEQ ID NO: 47, SEQ ID NO: 49, SEQ ID NO: 55, or SEQ ID NO: 59. In yet another aspect of this embodiment, the sample is selected from the group consisting of corn flour, corn meal, corn syrup, corn oil, cornstarch, and cereals manufactured in whole or in part to contain corn by-products.

Another embodiment of the present invention encompasses a corn plant, or parts thereof, and seed from a corn plant comprising the genotype of the transgenic event MIR162, wherein the genotype comprises a nucleotide sequence set forth in SEQ ID NO: 1, SEQ ID NO: 38, SEQ ID NO: 41, SEQ ID NO: 45, SEQ ID NO: 47, SEQ ID NO: 49, SEQ ID NO: 55, SEQ ID NO: 59, or the complements thereof. One example of corn seed comprising the nucleic acid molecules of the invention was deposited 23 Jan. 2007 and assigned the ATCC Accession No. PTA-8166. In one aspect of this embodiment, the corn plant is from the inbred corn lines CG5NA58, CG5NA58A, CG3ND97, CG5NA01, CG5NF22, CG4NU15, CG00685, CG00526, CG00716, NP904, NP911, NP948, NP934, NP982, NP991, NP993, NP2010, NP2013, NP2015, NP2017, NP2029, NP2031, NP2034, NP2045, NP2052, NP2138, NP2151, NP2166, NP2161, NP2171, NP2174, NP2208, NP2213, NP2222, NP2275, NP2276, NP2316, BCTT609, AF031, NPH8431, 894, BUTT201, R327H, 2044BT, and 2070BT. One skilled in the art will recognize however, that the MIR162 genotype can be introgressed into any plant variety that can be bred with corn, including wild maize species, and thus the list of inbred lines of this embodiment are not meant to be limiting.

In another embodiment, the present invention encompasses a corn plant comprising at least a first and a second DNA sequence linked together to form a contiguous nucleotide sequence, wherein the first DNA sequence is within a junction sequence and comprises at least about 11 contiguous nucleotides selected from the group consisting of nucleotides 1079-1098 of SEQ ID NO: 49, nucleotides 9381-9400, and the complements thereof, wherein the second DNA sequence is within the heterologous insert DNA sequence set forth in SEQ ID NO: 49, and the complements thereof; and wherein the first and the second DNA sequences are useful as nucleotide primers or probes for detecting the presence of corn event MIR162 nucleic acid sequences in a biological sample. In one aspect of this embodiment, the nucleotide primers are used in a DNA amplification method to amplify a target DNA sequence from template DNA extracted from the corn plant and the corn plant is identifiable from other corn plants by the production of an amplicon corresponding to a DNA sequence comprising SEQ ID NO: 45 or SEQ ID NO: 47.

Corn plants of the invention can be further characterized in that simultaneously digesting the plant's genomic DNA with the restriction endonucleases KpnI, EcoRV or NcoI results in an about a 8 kb, a 13 kb or 4.6 kb vip3Aa20 hybridizing band, respectively, using a vip3Aa20 probe under high stringency conditions. Exemplified herein is a vip3Aa20 probe comprising the nucleotide sequence set forth in SEQ ID NO: 13.

Corn plants of the invention can be further characterized in that digesting the plant's genomic DNA with the restriction endonuclease Acc65I or BamHI results in a single pmi hybridizing band using a pmi probe under high stringency conditions. Exemplified herein is a pmi probe comprising the nucleotide sequence set forth in SEQ ID NO: 14.

In one embodiment, the present invention provides a corn plant, wherein the MIR162 genotype confers upon the corn plant insect resistance or ability to utilize mannose as a carbon source, or both insect resistance and the ability to utilize mannose as a carbon source. In one aspect of this embodiment, the transgenic genotype conferring insect resistance upon the corn plant of the invention comprises a vip3Aa20 gene and the transgenic genotype conferring the ability to utilize mannose as a carbon source upon the maize plant of the invention comprises a pmi gene.

In yet another embodiment, the present invention provides a method for producing a corn plant resistant to lepidopteran pests comprising: (a) sexually crossing a first parent corn plant with a second parent corn plant, wherein said first or second parent corn plant comprises event MIR162 DNA, thereby producing a plurality of first generation progeny plants; (b) selecting a first generation progeny plant that is resistant to one or more lepidopteran pests; (c) selfing the first generation progeny plant, thereby producing a plurality of second generation progeny plants; and (d) selecting from the second generation progeny plants, a plant that is resistant to one or more lepidopteran pests; wherein the second generation progeny plants comprise a nucleotide sequence selected from the group consisting of SEQ ID NO: 1, SEQ ID NO: 45, SEQ ID NO: 47, SEQ ID NO: 49, SEQ ID NO: 55, and SEQ ID NO: 59.

In another embodiment, the present invention provides a method of producing hybrid corn seeds comprising: (a) planting seeds of a first inbred corn line comprising a nucleotide sequence selected from the group consisting of SEQ ID NO: 1, SEQ ID NO: 45, SEQ ID NO: 47, SEQ ID NO: 49, SEQ ID NO: 55, and SEQ ID NO: 59, and seeds of a second inbred line having a different genotype; (b) cultivating corn plants resulting from said planting until time of flowering; (c) emasculating said flowers of plants of one of the corn inbred lines; (d) sexually crossing the two different inbred lines with each other; and (e) harvesting the hybrid seed produced thereby. In one aspect of this embodiment, the first inbred corn line provides the female parents. In another aspect of this embodiment, the first inbred corn line provides the male parents. The present invention also encompasses the hybrid seed produced by the embodied method and hybrid plants grown from the seed.

One skilled in the art will recognize that the transgenic genotype of MIR162 can be introgressed by breeding into other corn lines comprising different transgenic genotypes. For example, a MIR162 corn inbred can be crossed with a corn inbred comprising the transgenic genotype of the lepidopteran resistant Bt11 event (U.S. Pat. Nos. 6,114,608 and 6,342,660, herein incorporated by reference). The resulting seed and progeny plants have the stacked insect resistance traits and the combined spectrum of activity of Cry1Ab and Vip3Aa20. Another trait stack encompassed by the present invention includes combining the MIR162 insect resistance trait and the MIR604 insect resistance trait (US Patent Application publication No. 2005/0216970, published Sep. 29, 2005, herein incorporated by reference). The stacked traits in the resulting seed and progeny confer upon the plants an increased spectrum of activity; i.e. the plants are active against both lepidopteran and coleopteran insect pests.

Therefore, the present invention encompasses a method of protecting a transgenic corn plant from feeding damage by one or more insect pests wherein the method comprises stacking in the same transgenic corn plant a Vip3Aa20 insect resistance trait with another insect resistance trait that is different from Vip3Aa20, whereby the stacked traits protect the corn plant against feeding damage by one or more insect pests to a greater degree than would be expected due to the insect resistance traits alone. In one aspect of this embodiment, the Vip3Aa20 insect resistance trait comprised in event MIR162 is stacked with the Cry3A055 insect resistance trait comprised in event MIR604 in the same transgenic corn plant by sexually crossing event MIR162 with event MIR604 or by transforming the traits together into the same plant.

Examples of other transgenic events which can be crossed with a MIR162 inbred include, the glyphosate tolerant GA21 event, the glyphosate tolerant/lepidopteran insect resistant MON802 event, the lepidopteran resistant DBT418 event, the male sterile event MS3, the phosphinothricin tolerant event B16, the lepidopteran insect resistant event MON 80100, the phosphinothricin tolerant events T14 and T25, the lepidopteran insect resistant event 176, and the coleopteran resistant event MON863, all of which are known in the art. It will be further recognized that other combinations or stacks can be made with the transgenic genotype of the invention and thus these examples should not be viewed as limiting.

One skilled in the art will also recognize that transgenic corn seed comprising the MIR162 genotype can be treated with various seed-treatment chemicals, including insecticides, to augment or syngergize the insecticidal activity of the Vip3Aa20 protein.

The subject invention discloses herein a specific site on chromosome 5 in the maize genome that is excellent for insertion of heterologous nucleic acids. Also disclosed is a 5' molecular marker (opie2; nucleotides 1680-3338 of SEQ ID NO: 106) and a 3' molecular marker (gag; nucleotides 43,275-45,086 of SEQ ID NO: 106) useful in identifying the location of a targeting site on chromosome 5. Thus, the subject invention provides methods to introduce heterologous nucleic acids of interest into this pre-established target site or in the vicinity of this target site. The subject invention also encompasses a corn seed and/or a corn plant comprising any heterologous nucleotide sequence inserted at the disclosed target site or in the general vicinity of such site. One option to accomplish such targeted integration is to substitute a different insert in place of the vip3Aa20 expression cassette exemplified herein. In this general regard, targeted homologous recombination, for example without limitation, can be used according to the subject invention. "Homologous recombination" refers to a reaction between any pair of nucleotide sequences having corresponding sites containing a similar nucleotide sequence (i.e., homologous sequences) through which the two molecules can interact (recombine) to form a new, recombinant DNA sequence. The sites of similar nucleotide sequence are each referred to herein as a "homology sequence". Generally, the frequency of homologous recombination increases as the length of the homology sequence increases. Thus, while homologous recombination can occur between two nucleotide sequences that are less than identical, the recombination frequency (or efficiency) declines as the divergence between the two sequences increases. Recombination may be accomplished using one homology sequence on each of the donor and target molecules, thereby generating a "single-crossover" recombination product. Alternatively, two homology sequences may be placed on each of the target and donor nucleotide sequences. Recombination between two homology sequences on the donor with two homology sequences on the target generates a "double-crossover" recombination product. If the homology sequences on the donor molecule flank a sequence that is to be manipulated (e.g., a sequence of interest), the double-crossover recombination with the target molecule will result in a recombination product wherein the sequence of interest replaces a DNA sequence that was originally between the homology sequences on the target molecule. The exchange of DNA sequence between the target and donor through a double-crossover recombination event is termed "sequence replacement." This type of technology is the subject of, for example, US patent Application Publication No. 2006/0253918, herein incorporated by reference. With the disclosed target site now being identified and with the sequences surrounding the identified target site, the skilled person will recognize that other methods for targeted integration of heterologous nucleic acids may be used. Such methods, for example without limitation, are disclosed in US Patent Application Publication No. 2007/0039074 and US Patent Application Publication No. 2006/0130179.

In one embodiment, the present invention encompasses a maize chromosomal target site located on chromosome 5 between a opie2 molecular marker set forth as nucleotides 1680-3338 of SEQ ID NO: 106 and a gag molecular marker set forth as nucleotides 43,275-45,086 of SEQ ID NO: 106, wherein the target site comprises a heterologous nucleic acid. In another embodiment, the maize chromosomal target site is located on chromosome 5 between nucleotides 25,454 and 25,513 of SEQ ID NO: 106. In yet another embodiment, the chromosomal target site is flanked 5' by nucleotides 5,454 to 25,454 of SEQ ID NO: 106 and flanked 3' by nucleotides 25,513 to 45,513 of SEQ ID NO: 106.

In one embodiment, the present invention encompasses a method of making a transgenic maize plant comprising inserting a heterologous nucleic acid at a position on chromosome 5 located between a opie2 molecular marker set forth as nucleotides 1680-3338 of SEQ ID NO: 106 and a gag molecular marker set forth as nucleotides 43,275-45,086 of SEQ ID NO: 106. In another embodiment, the heterologous nucleic acid is inserted on chromosome 5 between nucleotides 25,454 and 25,513 of SEQ ID NO: 106. In still another embodiment, the inserted heterologous nucleic acid is flanked 5' by nucleotides 5,454 to 25,454 of SEQ ID NO: 106 and flanked 3' by nucleotides 25,513 to 45,513 of SEQ ID NO: 106

The transgenic genotype of the present invention can be introgressed in any corn inbred or hybrid using art recognized breeding techniques. The goal of plant breeding is to combine in a single variety or hybrid various desirable traits. For field crops, these traits may include resistance to insects and diseases, tolerance to herbicides, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Corn (*Zea mays* L.), can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the ears.

A reliable method of controlling male fertility in plants offers the opportunity for improved plant breeding. This is especially true for development of corn hybrids, which relies upon some sort of male sterility system. There are several options for controlling male fertility available to breeders, such as: manual or mechanical emasculation (or detasseling), cytoplasmic male sterility, genetic male sterility, gametocides and the like.

Hybrid corn seed is typically produced by a male sterility system incorporating manual or mechanical detasseling. Alternate strips of two corn inbreds are planted in a field, and the pollen-bearing tassels are removed from one of the inbreds (female). Providing that there is sufficient isolation from sources of foreign corn pollen, the ears of the detasseled inbred will be fertilized only from the other inbred (male), and the resulting seed is therefore hybrid and will form hybrid plants.

The laborious, and occasionally unreliable, detasseling process can be avoided by using one of many methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329,308 and PCT application PCT/CA90/00037 published as WO 90/08828).

The use of male sterile inbreds is but one factor in the production of corn hybrids. Plant breeding techniques known in the art and used in a corn plant breeding program include, but are not limited to, recurrent selection, backcrossing, pedigree breeding, restriction length polymorphism enhanced selection, genetic marker enhanced selection and transformation. The development of corn hybrids in a corn plant breeding program requires, in general, the development of homozygous inbred lines, the crossing of these lines, and the evaluation of the crosses. Pedigree breeding and recurrent selection breeding methods are used to develop inbred lines from breeding populations. Corn plant breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development, as practiced in a corn plant-breeding program, are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$; etc.

Recurrent selection breeding, backcrossing for example, can be used to improve an inbred line and a hybrid that is made using those inbreds. Backcrossing can be used to transfer a specific desirable trait from one inbred or source to an inbred that lacks that trait. This can be accomplished, for example, by first crossing a superior inbred (recurrent parent) to a donor inbred (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait, the progeny will be homozygous for loci controlling the characteristic being transferred, but will be like the superior parent for essentially all other genes. The last backcross generation is then selfed to give pure breeding progeny for the gene(s) being transferred. A hybrid developed from inbreds containing the transferred gene(s) is essentially the same as a hybrid developed from the same inbreds without the transferred gene(s).

Elite inbred lines, that is, pure breeding, homozygous inbred lines, can also be used as starting materials for breeding or source populations from which to develop other inbred lines. These inbred lines derived from elite inbred lines can be developed using the pedigree breeding and recurrent selection breeding methods described earlier. As an example, when backcross breeding is used to create these derived lines in a corn plant-breeding program, elite inbreds can be used as a parental line or starting material or source population and can serve as either the donor or recurrent parent.

A single cross corn hybrid results from the cross of two inbred lines, each of which has a genotype that complements the genotype of the other. The hybrid progeny of the first generation is designated $F_1$. In the development of commercial hybrids in a corn plant-breeding program, only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a corn hybrid in a corn plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny ($F_1$). During the inbreeding process in corn, the vigor of the lines decreases. Vigor is restored when two different inbred lines are crossed to produce the hybrid progeny ($F_1$). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)×(C×D). A three-way cross hybrid is produced from three inbred lines where two of the inbred lines are crossed (A×B) and then the resulting $F_1$ hybrid is crossed with the third inbred (A×B)×C. Much of the hybrid vigor exhibited by $F_1$ hybrids is lost in the next generation ($F_2$). Consequently, seed from hybrids is not used for planting stock.

Hybrid seed production requires elimination or inactivation of pollen produced by the female parent. Incomplete removal or inactivation of the pollen provides the potential for self-pollination. This inadvertently self-pollinated seed may be unintentionally harvested and packaged with hybrid seed.

Once the seed is planted, it is possible to identify and select these self-pollinated plants. These self-pollinated plants will be genetically equivalent to the female inbred line used to produce the hybrid.

Typically these self-pollinated plants can be identified and selected due to their decreased vigor. Female selfs are identified by their less vigorous appearance for vegetative and/or reproductive characteristics, including shorter plant height, small ear size, ear and kernel shape, cob color, or other characteristics.

Identification of these self-pollinated lines can also be accomplished through molecular marker analyses. See, "The Identification of Female Selfs in Hybrid Maize: A Comparison Using Electrophoresis and Morphology", Smith, J. S. C. and Wych, R. D., Seed Science and Technology 14, pp. 1-8 (1995), the disclosure of which is expressly incorporated herein by reference. Through these technologies, the homozygosity of the self-pollinated line can be verified by analyzing allelic composition at various loci along the genome. Those methods allow for rapid identification of the invention disclosed herein. See also, "Identification of Atypical Plants in Hybrid Maize Seed by Postcontrol and Electrophoresis" Sarca, V. et al., Probleme de Genetica Teoritica si Aplicata Vol. 20 (1) p. 29-42.

As is readily apparent to one skilled in the art, the foregoing are only some of the various ways by which the inbred of the present invention can be obtained by those looking to introgress the transgenic genotype of the invention into other corn lines. Other means are available, and the above examples are illustrative only.

The following examples are intended solely to illustrate one or more preferred embodiments of the invention and are not to be construed as limiting the scope of the invention.

EXAMPLES

Example 1. Transformation and Selection of the MIR162 Event

The MIR604 event was produced by Agrobacterium-mediated transformation of a proprietary corn (Zea mays) line Immature embryos were transformed essentially as described in Negrotto et al. (Plant Cell Reports 19: 798-803, 2000), incorporated herein by reference, using a DNA fragment from plasmid pNOV1300 (SEQ ID NO: 3). pNOV1300 contains a nucleotide sequence comprising tandem expression cassettes. The first expression cassette comprises a ZmUbiInt promoter region from a Zea mays polyubiquitin gene, which contains the first intron (GenBank® Accession number S94464) operably linked to a vip3Aa19 coding sequence further operably linked to PEPC Intron #9 from the phosphoenolpyruvate carboxylase gene (GenBank® Accession Number X15239) from Zea mays (Matsuoka and Minami, 1989. European J. Of Biochem. 181: 593-598) and a 35S terminator sequence from the 35S RNA from the cauliflower mosaic virus genome (Similar to GenBank® Accession Number AF140604). Its function is to provide a polyadenylation sequence (Franck et al., 1980. Cell 21:285-294). The vip3Aa19 gene in pNOV1300 comprises a synthetic maize-optimized vip3Aa coding sequence (Estruch, et al., 1999.) which was synthesized to accommodate the preferred codon usage for maize (Murray et al., 1989). The synthetic vip3Aa19 coding sequence used in plant transformations encodes the identical amino acid sequence as the native vip3Aa1 coding sequence found in the soil bacterium Bacillus thuringiensis strain AB88 (U.S. Pat. No. 5,877,012), with the exception of a single amino acid difference at position 284; the native vip3Aa1 coding sequence encodes lysine, whereas the synthetic vip3Aa19 coding sequence encodes glutamine at this position. The vip3Aa19 coding sequence encodes an insect control protein, Vip3Aa19 that provides resistance to lepidopteran insects. The second expression cassette is comprised of a ZmUbiInt promoter operably linked to a pmi coding sequence (also known as E. coli manA) encoding phosphomannose isomerase (GenBank® Accession number M15380), which catalyzes the isomerization of mannose-6-phosphate to fructose-6-phosphate (Negrotto et al., 2000). The pmi coding sequence is further operably linked to a nopaline synthase 3' end transcription termination and polyadenylation sequence.

Immature embryos were excised from 8-12 day old ears and rinsed with fresh medium in preparation for transformation. Embryos were mixed with the suspension of Agrobacterium cells harboring the transformation vector pNOV1300, vortexed for 30 seconds, and allowed to incubate for an additional 5 minutes. Excess solution containing Agrobacterium was aspirated and embryos were then moved to plates containing a non-selective culture medium. Embryos were co-cultured with the remaining Agrobacterium at 22° C. for 2-3 days in the dark. Embryos were transferred to culture medium supplemented with ticarcillin (100 mg/ml) and silver nitrate (1.6 mg/l) and incubated in the dark for 10 days. Embryos producing embryogenic callus were transferred to cell culture medium containing mannose.

Regenerated plantlets were tested by TAQMAN® PCR analysis (see Example 2) for the presence of both the pmi and vip3Aa19 genes, as well as for the absence of the antibiotic resistance spectinomycin (spec) gene. It was later discovered (See Example 4 below) that during the transformation process two mutations were introduced into the vip3Aa19 coding sequence, one of which resulted in an amino acid change in the Vip3Aa19 protein. Therefore, this new vip3Aa coding sequence, which is unique to event MIR162, was designated vip3Aa20. The vip3Aa20 coding sequence encodes isoleucine at position 129 in place of the methionine residue encoded by the vip3Aa19 gene.

Plants positive for both transgenes, and negative for the spec gene, were transferred to the greenhouse for further propagation. Positive events were identified and screened using insect bioassays against fall armyworm. Insecticidal events were characterized for copy number by TAQMAN analysis. MIR162 was chosen for further analysis based on having a single copy of the transgenes, good protein expression as identified by ELISA, and good insecticidal activity against fall armyworm.

The breeding pedigree of the MIR162 event was as follows: T₀ MIR162 plant (x NPH8431)→→NPH8431 (MIR162) F₁ (x NP2161)→NP2161(MIR162) F₁ (x NP2161)→NP2161 (MIR162) BC1F₁ (x B9620)→F₁ (x B9620)→BC1F₁ (x B9620)→BC2F₁ (x B9620)→BC3F₁ (x B9620)→BC4F₁ (x B9620). Plant material from the BC4 generation was used for the Southern analysis, copy number determination and sequencing of the insert DNA. Negative controls for the experiments consisted of 10 negative segregant plants from the BC4 generation.

Example 2. MIR162 Detection by TAQMAN PCR

TAQMAN analysis was essentially carried out as described in Ingham et al. (Biotechniques, 31:132-140, 2001) herein incorporated by reference. Briefly, genomic DNA was isolated from leaves of transgenic and non-transgenic corn plants using the Puregene® Genomic DNA Extraction kit (Gentra Systems, Minneapolis, Minn.) essentially according to the manufacturer's instruction, except all steps were conducted in 1.2 ml 96-well plates. The dried DNA pellet was resuspended in TE buffer (10 Mm Tris-HCl, pH 8.0, 1 mM EDTA).

TAQMAN PCR reactions were carried out in 96-well plates. For the endogenous corn gene control, primers and probes were designed specific to the Zea mays alcohol dehydrogenase (adhI) coding sequence (Genbank accession no. AF044295). It will be recognized by the skilled person that other corn genes can be used as endogenous controls.

Reactions were multiplexed to simultaneously amplify vip3Aa and adhI or pmi and adhI. For each sample, a master mixture was generated by combining 20 μL extracted genomic DNA with 35 μL 2× TAQMAN Universal PCR Master Mix (Applied Biosystems) supplemented with primers to a final concentration of 900 nM each, probes to a final concentration of 100 nM each, and water to a 70 μL final volume. This mixture was distributed into three replicates of 20 μL each in 96-well amplification plates and sealed with optically clear heat seal film (Marsh Bio Products). PCR was run in the ABI Prism 7700 instrument using the following amplification parameters: 2 min at 50° C. and 10 min at 95° C., followed by 35 cycles of 15 s at 95° C. and 1 min at 60° C.

Results of the TAQMAN analysis demonstrated that event MIR162 had one copy of the vip3Aa20 gene and one copy of the pmi gene.

Primers and probes that were used in the TAQMAN PCR reactions are shown in Table 1.

TABLE 1

Primers used in TAQMAN Assay.

| Primer Name | Primer Sequence | Sequence No: |
|---|---|---|
| Vip3Aa-forward | 5'CACCTTCAGCAACCCGAACTA3' | SEQ ID NO: 4 |
| Vip3Aa-reverse | 5'GCTTAGCCTCCACGATCATCTT3' | SEQ ID NO: 5 |
| Vip3Aa-probe | 5'GTCCTCGTCGCTGCCCTTCACCT3' (5' label = FAM, 3' label = TAMRA) | SEQ ID NO: 6 |
| PMI-forward | 5'CCGGGTGAATCAGCGTTT3' | SEQ ID NO: 7 |
| PMI-reverse | 5'GCCGTGGCCTTTGACAGT3' | SEQ ID NO: 8 |
| PMI-probe | 5'TGCCGCCAACGAATCACCGG3' (5' label = FAM, 3'label = TAMRA) | SEQ ID NO: 9 |
| ZmADH-267forward | 5'GAACGTGTGTTGGGTTTGCAT3' | SEQ ID NO: 10 |
| ZmADH-337 reverse | 5'TCCAGCAATCCTTGCACCTT3' | SEQ ID NO: 11 |
| ZmADH-316 probe | 5'TGCAGCCTAACCATGCGCAGGGTA3' (5'label = TET, 3' label = TAMRA) | SEQ ID NO: 12 |

Example 3. MIR162 Detection by Southern Blot

Genomic DNA used for southern analysis was isolated from pooled leaf tissue of 10 plants representing the BC4 generation of MIR162 using essentially the method of Thomas et al. (Theor. Appl. Genet. 86:173-180, 1993), incorporated herein by reference. All plants used for DNA isolation were individually analyzed using TAQMAN PCR (as described in Example 2) to confirm the presence of a single copy of the vip3Aa20 gene and the pmi gene. For the negative segregant controls, DNA was isolated from pooled leaf tissue of negative segregants from the BC4 generation. These negative segregant plants were individually analyzed using TAQMAN PCR to confirm the absence of the vip3Aa20 and pmi genes, but were, as expected, positive for the endogenous maize adhI gene.

Southern analysis was carried out using conventional molecular biology techniques. (See Chomczynski, P. 1992. Analytical Biochemistry 201:34-139) Genomic DNA (7.5 μg) was digested with restriction enzymes that digest within the event MIR162 insert, but not within the coding sequence that corresponds to the specific probe used in the experiment. This approach allowed for determination of the number of copies of each gene, corresponding to the specific probe used for each Southern analysis, which was incorporated into event MIR162.

Another series of restriction digests was performed in which the insert was digested with restriction enzymes that would release a fragment of known size from the insert. This approach provided additional evidence for the presence of a single copy of each coding sequence present in MIR162 and allowed for the detection of partial copies of the insert that may be closely linked to the MIR162 insert. Following agarose gel electrophoresis and alkaline transfer to a ZetaProbe® GT membrane (Bio-Rad, Cat. No. 162-0195), hybridizations were carried out using full-length PCR generated element probes. The probes were labeled with $^{32}$P via random priming using the MegaPrime™ system (Amersham Biosciences, Cat. No. RPN1607). Hybridization was carried out at 65° C., followed by multiple washes in 2×SSC, 0.1% SDS and then 0.1×SSC and 0.1% SDS. The membranes were then subjected to autoradiography.

Included in each Southern analysis were three control samples: (1) DNA from a negative (non-transformed) segregant used to identify any endogenous *Zea mays* sequences that may cross-hybridize with the element-specific probe; (2) DNA from a negative segregant into which is introduced an amount of digested pNOV1300 that is equal to one copy number based on plasmid size was introduced, to demonstrate the sensitivity of the experiment in detecting a single gene copy within the *Zea mays* genome; and (3) Digested pNOV1300 plasmid equal to one copy number based on plasmid size, to act as a positive control for hybridization as well as to demonstrate the sensitivity of the experiment.

The results of Southern analyses demonstrated that the MIR162 insert contains a single copy of the vip3Aa20 gene and pmi gene and contains no pNOV1300 backbone sequences. A vip3Aa19 probe (SEQ ID NO: 13) was used for the vip3Aa20 Southern analysis. The nucleotide sequences of vip3Aa19 and vip3Aa20 differ by two nucleotides and are 99.9% identical. Therefore, the vip3Aa19 probe hybridized to the vip3Aa20 sequence present in MIR162 under stringent conditions. Using the vip3Aa19 probe, a KpnI and an EcoRV digest resulted in single hybridization bands approximately 8 kb and 13 kb in size, respectively. In addition, an NcoI double digest resulted in a single hybridization band consistent with the expected size of 4.6 kb. Using the pmi probe (SEQ ID NO: 14), a Acc65I and a BamHI digest resulted in single hybridization bands of approximately 4 kb and 6 kb in size, respectively. In addition, an XmaI+HindIII double digest resulted in a single hybridization band consistent with the expected size of 8.1 kb. The 8.1 kb XmaI+HindIII pNOV1300 band (positive control) also hybridized with the vip3Aa19 and pmi probes as expected. Some cross-hybridization in the plasmid-only lanes with the DNA ladder probe was detected. Typically commercially available DNA ladders may contain some vector sequences that can cross-hybridize with the plasmid control sequences as observed in these experiments, but, this does not impact the findings of this study. Finally, a pNOV1300 backbone probe did not hybridize demonstrating the absence of incorporation of any pNOV1300 vector backbone sequences into MIR162 during the transformation process.

Example 4. Heterologous DNA Insert Sequencing

The nucleotide sequence of the vip3Aa and pmi coding sequences in the heterologous DNA molecule inserted in MIR162 was determined to demonstrate overall integrity of the insert, contiguousness of the functional elements and to detect any individual basepair changes. The coding sequences were amplified from DNA derived from the BC4 generation. PCR amplification was carried out using either Expand High Fidelity PCR system (Roche, Cat. No. 1732650) or PfuUltra™ Hotstart High-Fidelity DNA polymerase (Stratagene, Cat. No. 600390). Each PCR product was individually cloned into either pCR®-XL-TOPO vector (Invitrogen, Cat. No. K4700-20) or pCR®-BluntII-TOPO vector (Invitrogen, Cat. No. K2800-20) and three separate clones for each PCR product were identified and sequenced. Sequencing was carried out using the ABI3730XL analyzer using ABI BigDye® 1.1 or Big Dye 3.1 dGTP (for GC-rich templates) chemistry. The sequence analysis was done using the Phred, Phrap, and Consed package from the University of Washington and was carried out to an error rate of less than 1 in 10,000 bases (Ewing & Green, 1998. Genome Research 8:186-194). The final consensus sequence for each gene was determined by combining the sequence data from the three individual clones to generate one consensus sequence for each gene. Sequence alignment was performed using the ClustalW program with the following parameters: scoring matrix blosum55, gap opening penalty 15, gap extension penalty 6.66 (Thompson et al, 1994. Nucleic Acids Research 22:4673-4680).

The full vip3Aa20 coding sequence was PCR amplified using primers MOV3Aa-01-5': 5'ATGAACAAGAACAACACCAA3' (SEQ ID NO: 15) and MOV3Aa-01-3': 5'CTACTTGATGCTCACGTCGTAG3' (SEQ ID NO: 16) and PfuUltra Hotstart enzyme generating a 2370 bp product. The PCR amplicon was sequenced using the primers shown in Table 2.

TABLE 2

| Primer Name | quence (5'→3') | Sequence No. |
|---|---|---|
| b03503b | ACGAGCAGAACCAGGTGC | SEQ ID NO: 17 |
| b03503c | GGTGAAGAAGGACGGCAG | SEQ ID NO: 18 |
| b03503d | ACCTGTCGCAAGCTGCTGGG | SEQ ID NO: 19 |
| b03503e | TGGACAAGCTGCTGTGTC | SEQ ID NO: 20 |
| b03503f | TGCAGGCCGACGAGAACAG | SEQ ID NO: 21 |
| b03503g | TGATCCAGTACACCGTGAA | SEQ ID NO: 22 |
| b03503h | ACCCTGACCCTGTACCAG | SEQ ID NO: 23 |
| b03504b | GTGTTGCCGCTGATGTTG | SEQ ID NO: 24 |
| b03504c | CGTACTCGGTCTTCGGCT | SEQ ID NO: 25 |
| b03504d | CTGCAGGCCAAAGCCGTT | SEQ ID NO: 26 |
| b03504e | TCGCCGTAGATCACCTCG | SEQ ID NO: 27 |
| b03504f | GCTTGCGACAGGTGGTCA | SEQ ID NO: 28 |
| b03504g | TTGCTGCTGGTCTCGGTGG | SEQ ID NO: 29 |
| b03504h | CGTTGGCGATCTTAAGGAT | SEQ ID NO: 30 |
| b00203c | GCAAGCCATCGATTCAC | SEQ ID NO: 31 |
| b00203d | GCAACACCCTGACCCTG | SEQ ID NO: 32 |
| b00203e | TCTACGACGTGAGCATCAAG | SEQ ID NO: 33 |
| b00203f | GTAGAAGTGCACGATCGGG | SEQ ID NO: 34 |
| b00203g | CGGTGCTGGTCCAGTTG | SEQ ID NO: 35 |

Two other PCR reactions overlapped the full vip3Aa20 coding sequence. The 5' end of vip3Aa20 was covered with a PCR amplification using primers 162INSERT-F2: 5'ACACCAATGATGCAAATAGGC3' (SEQ ID NO: 36)

and VIP_R4 5'GAAGGTGTTCAGGTAGAACTCGAAG3' (SEQ ID NO: 37) and Expand High Fidelity enzyme. The second reaction covered the 3' end of vip3Aa20; the product was amplified with primers VIP-F3: 5'GGTGCTGTTCGA-GAAGAGGT3' (SEQ ID NO: 42) and PMI_REV1: 5'CGATTTATCACTCTCAATCACAT3' (SEQ ID NO: 43) and Expand High Fidelity enzyme. The amplicons generated by these reactions comprised a 2946 bp nucleotide sequence (SEQ ID NO: 38) and a 2577 bp nucleotide sequence (SEQ ID NO: 44), respectively.

The consensus sequence data revealed two nucleotide changes in the vip3Aa coding sequence in MIR162 (designated vip3Aa20; SEQ ID NO: 1) compared to the vip3Aa coding sequence in pNOV1300 (designated vip3Aa19), which was used to transform MIR162. The first nucleotide change, a G to T mutation, occurred at position 387 of the vip3Aa19 coding sequence (SEQ ID NO: 3). This mutation resulted in the methionine at position 129 of Vip3Aa19 being changed to isoleucine in Vip3Aa20 (M129I), SEQ ID NO: 2. The second nucleotide change occurred at position 1683 of the coding sequence, a G to C mutation, but did not result in an amino acid change. Therefore, the vip3Aa20 coding sequence (SEQ ID NO: 1) and the Vip3Aa20 protein (SEQ ID NO: 2) are unique to the MIR162 event and can be used to identify any plant comprising the MIR162 transgenic genotype. The pmi coding sequence MIR162 was identical to that in the transformation plasmid pNOV 1300. An alignment of the Vip3Aa20 and Vip3Aa19 insecticidal proteins is shown in Table 3.

TABLE 3

Comparison of Vip3Aa20 and Vip3Aa19 amino acid sequences.

| Name | Sequence Alignment |
|---|---|
| Vip3Aa20 | (1) MNKNNTKLSTRALPSFIDYFNGIYGFATGIKDIMNMIFKTDTGGDLTLDE |
| Vip3Aa19 | (1) MNKNNTKLSTRALPSFIDYFNGIYGFATGIKDIMNMIFKTDTGGDLTLDE |
| Vip3Aa20 | (51) ILKNQQLLNDISGKLDGVNGSLNDLIAQGNLNTELSKEILKIANEQNQVL |
| Vip3Aa19 | (51) ILKNQQLLNDISGKLDGVNGSLNDLIAQGNLNTELSKEILKIANEQNQVL |
| Vip3Aa20 | (101) NDVNNKLDAINTMLRVYLPKITSMLSDVIKQNYALSLQIEYLSKQLQEIS |
| Vip3Aa19 | (101) NDVNNKLDAINTMLRVYLPKITSMLSDVMKQNYALSLQIEYLSKQLQEIS |
| Vip3Aa20 | (151) DKLDIINVNVLINSTLTEITPAYQRIKYVNEKFEELTFATETSSKVKKDG |
| Vip3Aa19 | (151) DKLDIINVNVLINSTLTEITPAYQRIKYVNEKFEELTFATETSSKVKKDG |
| Vip3Aa20 | (201) SPADILDELTELTELAKSVTKNDVDGFEFYLNTFHDVMVGNNLFGRSALK |
| Vip3Aa19 | (201) SPADILDELTELTELAKSVTKNDVDGFEFYLNTFHDVMVGNNLFGRSALK |
| Vip3Aa20 | (251) TASELITKENVKTSGSEVGNVYNFLIVLTALQAQAFLTLTTCRKLLGLAD |
| Vip3Aa19 | (251) TASELITKENVKTSGSEVGNVYNFLIVLTALQAQAFLTLTTCRKLLGLAD |
| Vip3Aa20 | (301) IDYTSIMNEHLNKEKEEFRVNILPTLSNTFSNPNYAKVKGSDEDAKMIVE |
| Vip3Aa19 | (301) IDYTSIMNEHLNKEKEEFRVNILPTLSNTFSNPNYAKVKGSDEDAKMIVE |
| Vip3Aa20 | (351) AKPGHALIGFEISNDSITVLKVYEAKLKQNYQVDKDSLSEVIYGDMDKLL |
| Vip3Aa19 | (351) AKPGHALIGFEISNDSITVLKVYEAKLKQNYQVDKDSLSEVIYGDMDKLL |
| Vip3Aa20 | (401) CPDQSEQIYYTNNIVFPNEYVITKIDFTKKMKTLRYEVTANFYDSSTGEI |
| Vip3Aa19 | (401) CPDQSEQIYYTNNIVFPNEYVITKIDFTKKMKTLRYEVTANFYDSSTGEI |
| Vip3Aa20 | (451) DLNKKKVESSEAEYRTLSANDDGVYMPLGVISETFLTPINGFGLQADENS |
| Vip3Aa19 | (451) DLNKKKVESSEAEYRTLSANDDGVYMPLGVISETFLTPINGFGLQADENS |
| Vip3Aa20 | (501) RLITLTCKSYLRELLLATDLSNKETKLIVPPSGFISNIVENGSIEEDNLE |
| Vip3Aa19 | (501) RLITLTCKSYLRELLLATDLSNKETKLIVPPSGFISNIVENGSIEEDNLE |
| Vip3Aa20 | (551) PWKANNKNAYVDHTGGVNGTKALYVHKDGGISQFIGDKLKPKTEYVIQYT |
| Vip3Aa19 | (551) PWKANNKNAYVDHTGGVNGTKALYVHKDGGISQFIGDKLKPKTEYVIQYT |
| Vip3Aa20 | (601) VKGKPSIHLKDENTGYIHYEDTNNNLEDYQTINKRFTTGTDLKGVYLILK |
| Vip3Aa19 | (601) VKGKPSIHLKDENTGYIHYEDTNNNLEDYQTINKRFTTGTDLKGVYLILK |
| Vip3Aa20 | (651) SQNGDEAWGDNFIILEISPSEKLLSPELINTNNWTSTGSTNISGNTLTLY |
| Vip3Aa19 | (651) SQNGDEAWGDNFIILEISPSEKLLSPELINTNNWTSTGSTNISGNTLTLY |
| Vip3Aa20 | (701) QGGRGILKQNLQLDSFSTYRVYFSVSGDANVRIRNSREVLFEKRYMSGAK |
| Vip3Aa19 | (701) QGGRGILKQNLQLDSFSTYRVYFSVSGDANVRIRNSREVLFEKRYMSGAK |
| Vip3Aa20 | (751) DVSEMFTTKFEKDNFYIELSQGNNLYGGPIVHFYDVSIK |
| Vip3Aa19 | (751) DVSEMFTTKFEKDNFYIELSQGNNLYGGPIVHFYDVSIK |

The shaded box indicates the amino acid change.

Example 5. Analysis of Flanking DNA Sequence

A number of methods are known to those of skill in the art to amplify unknown DNA sequences adjacent to a core region of known sequence. Those methods include, but are not limited to, inverse PCR (iPCR) [Ochman et. al., Genetics 120:621-623 (1988); Triglia et. al., Nucleic Acids Res. 16:8186 (1988)], panhandle PCR [Jones and Winistorfer, Nucleic Acids Res. 20:595-600 (1992); Jones and Winistorfer, Biotechniques 23:132-138 (1997)], cassette ligation-anchored PCR [Mueller and Wold, Science 246:780-786 (1989)], vectorette-PCR [Riley et. al., Nucleic Acids Res. 18:2887-2890 (1990)], novel-Alu-PCR [Puskas et. al., Nucleic Acids Res. 22:3251-3252 (1994)] and Thermal Asymmetric Interlaced PCR (TAIL-PCR) [Liu and Whittier, Genomics 25:673-681 (1995)].

One method used to amplify corn genome DNA sequence flanking the heterologous DNA inserted into event MIR162 was vectorette PCR essentially as described by Riley et al., Nucleic Acids Res. 18:2887-2890 (1990), incorporated herein by reference.

The 5' flanking sequence and junction sequence was confirmed using standard PCR procedures. The following primer pairs, or complements thereof, were used to confirm the sequence: 162INSERT-F2: 5'ACACCAATGATG-CAAATAGGC3' (SEQ ID NO: 36)/VIP_R4: 5'GAAGGT-GTTCAGGTAGAACTCGAAG3' (SEQ ID NO: 37) and CJB 179: 5'ATGCAAATAGGCTGGGAATAGTC3' (SEQ ID NO: 39)/CJB 134 5'GTACCAGCTTGCTGAGTGGCT3' (SEQ ID NO: 40). The resulting amplicon has the sequence shown is SEQ ID NO: 41 and comprises the 5' junction sequence of SEQ ID NO: 45. It will be recognized that other primer sequences can be used to confirm the flanking and junction sequences. Using this method, the MIR162 insert was found to be flanked 5' by nucleotides 1040-1088 of the corn genomic sequence shown in SEQ ID NO: 46.

A larger region of the 5' flanking sequence from event MIR162 was generated using the Seegene DNA Walking SpeedUp™ Premix kit following the manufacturer's instructions.

A first PCR reaction was performed independently in four individual tubes using primer FE1002: 5'CGTGACTCCCT-TAATTCTCCGCT3' (SEQ ID NO: 50) with one of the DW-ACP 1, 2, 3, or 4 primers supplied by the manufacturer. The following reagents were mixed in a PCR tube on ice: 100 µg MIR162 genomic DNA, 4 µl 2.5 µM DW-ACP (one each with DW-ACP 1, 2, 3, or 4), 4 µl 2.5 µM FE1002, 19 µl distilled water, and 25 µl 2× SeeAmp™ ACP™ Master Mix II. The tubes were placed in a preheated (94° C.) thermal cycler. PCR was completed using the following program: one cycle at 94° C. for five minutes, 42° C. for one minute, and 72° C. for two minutes, 30 cycles of 94° C. for 40 seconds, 55° C. for 40 seconds, and 72° C. for 90 seconds, and one cycle at 72° C. for seven minutes. The PCR products were purified using Exonuclease I and Shrimp Alkaline Phosphatase.

A second PCR reaction was performed independently in four individual tubes using primer FE1003: 5'GATCAGAT-TGTCGTTTCCCGCCTT3' (SEQ ID NO: 51) with the DW-ACPN primer supplied by the manufacturer of the kit. The following reagents were mixed in a PCR tube on ice: 3 µl purified PCR product, 1 µl 10 µM DW-ACPN, 1 µl 10 µM FE1003, 5 µl distilled water, and 10 µl 2× SeeAmp™ ACP™ Master Mix II. The tubes were placed in a preheated (94° C.) thermal cycler. PCR was completed using the following program: one cycle at 94° C. for five minutes, 35 cycles of 94° C. for 40 seconds, 60° C. for 40 seconds, and 72° C. for 90 seconds, and one cycle at 72° C. for seven minutes.

A third PCR reaction was performed independently in four individual tubes using primer FE1004: 5'GATT-GTCGTTTCCCGCCTTCAGTT3' (SEQ ID NO: 52) with the Universal primer supplied by the manufacturer. The following reagents were mixed in a PCR tube on ice: 2 µl purified PCR product, 1 µl 10 µM Universal primer, 1 µl 10 µM FE1004, 6 µl distilled water, and 10 µl 2× SeeAmp™ ACP™ Master Mix II. The tubes were placed in a preheated (94° C.) thermal cycler. PCR was completed using the following program: one cycle at 94° C. for five minutes, 35 cycles of 94° C. for 40 seconds, 60° C. for 40 seconds, and 72° C. for 90 seconds, and one cycle at 72° C. for seven minutes.

Ten µl of the PCR products were run on a 1% agarose gel containing ethidium bromide. The appropriate band was extracted from the agarose gel and purified using a Qiagen Qiaquick Gel Extraction Kit according to the manufacturer's instructions. The extracted DNA was cloned into an Invitrogen TOPO-XL cloning vector according to the manufacturer's instructions. This clone was transformed into E. coli, and the plasmid DNA was extracted from the cells after overnight growth with a Qiagen Miniprep kit according to the manufacturer's instructions. This plasmid was used for end run sequencing.

A new primer was designed within the new, previously unknown sequence to be used with a primer in the heterologous DNA insert to amplify the full 1 kb of flanking sequence out of the genomic DNA. Flanking sequence primer 162DWConf3: 5'CCTGTGTTGTTGGAACA-GACTTCTGTC3' (SEQ ID NO: 53) and insert DNA primer FE0900: 5'GGCTCCTTCAACGTTGCGGTTCTGTC3' (SEQ ID NO: 54) were used to amplify a nucleic acid molecule comprising the 5' flanking sequence for confirmation. The sequence of the resulting amplicon is set forth in SEQ ID NO: 55. This 5' amplicon comprises the 5' junction sequence set forth in SEQ ID NO: 45. Ten µl of the PCR product (amplicon) was run on a 1% agarose gel containing ethidium bromide. The appropriate band was extracted from the agarose gel and purified using a Qiagen Qiaquick Gel Extraction Kit according to the manufacturer's instructions. The extracted DNA was cloned into an Invitrogen TOPO-XL cloning vector according to the manufacturer's instructions. This clone was transformed into E. coli. Plasmid DNA was extracted from the cells after overnight growth in media with a Qiagen Miniprep kit according to the manufacturer's instructions. Three plasmids were completely sequenced using the primers shown in Table 4. The plasmid sequences were aligned to generate the complete confirmed 5' flanking sequence. Using this method, approximately 1 kb of the 5' flanking sequence (SEQ ID NO: 46) was determined

TABLE 4

Primer sequences.

| Primer Name | Sequence (5'→3')      | Sequence No.  |
|-------------|-----------------------|---------------|
| b00201h     | TTCACGGGAGACTTTATCTG  | SEQ ID NO: 60 |
| b00605a     | CCGATTCATTAATGCAG     | SEQ ID NO: 61 |
| b00701b     | ACGTAAAACGGCTTGTC     | SEQ ID NO: 62 |
| b00702b     | GTTTAAACTGAAGGCGG     | SEQ ID NO: 63 |
| b00704h     | AATAATATCACTCTGTACATCC | SEQ ID NO: 64 |

TABLE 4-continued

Primer sequences.

| Primer Name | Sequence (5'→3') | Sequence No. |
|---|---|---|
| b01106f | GTTGTAAAACGACGG | SEQ ID NO: 65 |
| b01709f | TAGGCACCCCAGGCTTTA | SEQ ID NO: 66 |
| b03504a | AATTGAATTTAGCGGCCG | SEQ ID NO: 67 |
| b05102f | GGTCCCTACAACATAAATAG | SEQ ID NO: 68 |
| b05102g | TTCGTCCCTACTATCAACGC | SEQ ID NO: 69 |
| b05102h | CTTTAGGCATCAGCGGGT | SEQ ID NO: 70 |
| b05103a | AGCATCTGCGTAAGCACA | SEQ ID NO: 71 |
| b05103b | CTGATGACACCAATGATGC | SEQ ID NO: 72 |
| b05103c | GATCAGATTGTCGTTTCCC | SEQ ID NO: 73 |
| b05103d | GCATCATTGGTGTCATCAG | SEQ ID NO: 74 |
| b05103e | TGTGCTTACGCAGATGCT | SEQ ID NO: 75 |
| b05103f | ACCCGCTGATGCCTAAAG | SEQ ID NO: 76 |
| b05103g | GCGTTGATAGTAGGGACGAA | SEQ ID NO: 77 |
| b05103h | CTATTTATGTTGTAGGGACC | SEQ ID NO: 78 |
| b05210a | CTAGACTGGAAAGCGGAG | SEQ ID NO: 79 |
| b05210b | CCACTTTCATCCCTAGTTG | SEQ ID NO: 80 |

The 3' flanking sequence from event MIR162 was generated using the Clonetech GenomeWalker™ Universal kit (Clonetech Laboratories, Inc.) following the manufacturer's instructions.

First, pools of uncloned, adaptor-ligated genomic DNA fragments, known as GenomeWalker "libraries" were constructed. Each library was constructed by digesting the MIR162 genomic DNA with a restriction enzyme (DraI, EcoRV, PvuII, StuI, and XmnI) as follows: For example, 25 μl MIR162 genomic DNA (0.1 μg/μl), 8 μl restriction enzyme (10 units/μl), 10 μl restriction enzyme buffer (10×), and 57 μl distilled H2O were mixed in a tube and incubated at 37° C. overnight.

DNA was then purified by using several rounds of phenol/chloroform extraction. Finally, the DNA was precipitated and washed with ethanol, dried and dissolved into 20 μl of TE buffer.

To ligate the GenomeWalker Adapter ends to the MIR162 genomic DNA, 4 μl of the digested, purified genomic DNA was mixed with 1.9 μl of GenomeWalker Adapter (25 μM), 1.6 μl 10× Ligation Buffer, and 0.5 μl T4 DNA Ligase (6 units/μl). These reactions were incubated overnight at 16° C. The reactions were stopped with incubation at 70° C. for five minutes. After the reaction was stopped, 72 μl of TE was added to each tube, and the contents were mixed thoroughly.

A first PCR reaction was performed using primer AP1, supplied by the manufacturer, with different primers designed within the known heterologous insert DNA sequence (Round 1 "gene specific primers" or "GSP1"). The following reagents were mixed in a PCR tube on ice: 1 μl of the appropriate MIR162 DNA library, 1 μl 10 μM AP1, 1 μl 10 μM GSP1, 1 μl 10 mM dNTPs, 5 μl 10× Advantage 2 PCR Buffer, 1 μl of BD Advantage 2 Polymerase, and 40 μl distilled water. PCR was completed using the following program: seven cycles at 94° C. for 25 seconds and 72° C. for four minutes, 32 cycles at 94° C. for 25 seconds and 67° C. for four minutes, and one cycle at 67° C. for four minutes.

Each primary PCR reaction was diluted 50-fold by adding 1 μl of the primary PCR product with 49 μl of distilled water. The reactions that worked were (1) the DraI and the XmnI libraries with the GSP1 primer 162GW3F1: 5'TCTCTT-GCTAAGCTGGGAGCTCGATCCG3' (SEQ ID NO: 56) and primer AP1.

A second PCR reaction was performed independently using primer AP2, supplied by the manufacturer, with different primers designed within the known heterologous insert DNA sequence (Round 2 "gene specific primers" or "GSP2"). The following reagents were mixed in a PCR tube on ice: 1 μl of the appropriate diluted primary PCR product, 1 μl 10 μM AP2, 1 μl 10 μM GSP2, 1 μl 10 mM dNTPs, 5 μl 10× Advantage 2 PCR Buffer, 1 μl of BD Advantage 2 Polymerase, and 40 μl distilled water. PCR was completed using the following program: five cycles at 94° C. for 25 seconds and 72° C. for four minutes, 20 cycles at 94° C. for 25 seconds and 67° C. for four minutes, and one cycle at 67° C. for four minutes. The reactions that worked were (1) the DraI and the XmnI libraries with the GSP2 primer 162GW3F2: 5'AAGATTGAATCCTGTTGCCGGTCTT-GCG3' (SEQ ID NO: 57) and primer AP2.

Ten μl of the PCR products were run on a 1% agarose gel containing ethidium bromide. The appropriate band was extracted from the agarose gel and purified using a Qiagen Qiaquick Gel Extraction Kit according to the manufacturer's instructions. The extracted DNA was cloned into an Invitrogen TOPO-XL cloning vector according to the manufacturer's instructions. This clone was transformed into E. coli, and the plasmid DNA was extracted from the cells after overnight growth with a Qiagen Miniprep kit according to the manufacturer's instructions. This plasmid was sequenced using end run sequencing.

A new primer was designed within the new, previously unknown sequence to be used with a primer in the insert DNA to amplify approximately 1 kb of 3' flanking sequence out of the genomic DNA. The insert DNA primer 162GW3F1: 5'TCTCTTGCTAAGCTGGGAGCTC-GATCCG3' (SEQ ID NO: 56) and a 3' flanking sequence primer 1623'GWR1: 5CTGGTGAACCGATTTTTACG-GAGG3' (SEQ ID NO: 58) were used to amplify a nucleic acid molecule comprising the 3' flanking sequence for confirmation. The sequence of the resulting amplicon is set forth in SEQ ID NO: 59. This 3' amplicon comprises the 3' junction sequence set forth in SEQ ID NO: 47. Ten μl of the PCR amplicon was run on a 1% agarose gel containing ethidium bromide. The appropriate band was extracted from the agarose gel and purified using a Qiagen Qiaquick Gel Extraction Kit according to the manufacturer's instructions. The extracted DNA was cloned into an Invitrogen TOPO-XL cloning vector according to the manufacturer's instructions. This clone was transformed into E. coli. Plasmid DNA was extracted from the cells after overnight growth in media with a Qiagen Miniprep kit according to the manufacturer's instructions. Three plasmids were completely sequenced using the primers shown in Table 5. The plasmid sequences were aligned to generate the complete confirmed 3' flanking sequence (SEQ ID NO: 48).

TABLE 5

Primer sequences.

| Primer Name | Sequence (5'→3') | Sequence No. |
|---|---|---|
| b00106a | GATTGAATCCTGTTGCC | SEQ ID NO: 81 |
| b00106b | TCTCATAAATAACGTCATGC | SEQ ID NO: 82 |
| b00108a | TCTGTGGATAACCGTATTAC | SEQ ID NO: 83 |

TABLE 5-continued

Primer sequences.

| Primer Name | Sequence (5'→3') | Sequence No. |
|---|---|---|
| b00201h | TTCACGGGAGACTTTATCTG | SEQ ID NO: 60 |
| b00605a | CCGATTCATTAATGCAG | SEQ ID NO: 61 |
| b00704h | AATAATATCACTCTGTACATCC | SEQ ID NO: 64 |
| b00712e | AGTAACATAGATGACACCGC | SEQ ID NO: 84 |
| b01106a | CCAGTGTGCTGGAATTCG | SEQ ID NO: 85 |
| b01106f | GTTGTAAAACGACGG | SEQ ID NO: 65 |
| b01107h | CCAGTGTGATGGATATCTGC | SEQ ID NO: 86 |
| b01108e | CCAGTGTGCTGGAATTCG | SEQ ID NO: 87 |
| b01111f | CCAGTGTGATGGATATCTGC | SEQ ID NO: 88 |
| b01709f | TAGGCACCCCAGGCTTTA | SEQ ID NO: 66 |
| b02701a | GTGTGCTGGAATTCGCCCTT | SEQ ID NO: 89 |
| b02701e | TATCTGCAGAATTCGCCCTT | SEQ ID NO: 90 |
| b02702a | GTGTGCTGGAATTCGCCCTT | SEQ ID NO: 91 |
| b02702e | TATCTGCAGAATTCGCCCTT | SEQ ID NO: 92 |
| b02703a | GTGTGCTGGAATTCGCCCTT | SEQ ID NO: 93 |
| b02703e | TATCTGCAGAATTCGCCCTT | SEQ ID NO: 94 |
| b02704a | GTGTGCTGGAATTCGCCCTT | SEQ ID NO: 95 |
| b02811a | GGTCTTGCGATGATTATC | SEQ ID NO: 96 |
| b05104c | GAGAGGAATGGCAGCAGA | SEQ ID NO: 97 |
| b05104d | CATGACGGGTTTGAGATT | SEQ ID NO: 98 |
| b05104e | AATCTCAAACCCGTCATG | SEQ ID NO: 99 |
| b05104f | TCTGCTGCCATTCCTCTC | SEQ ID NO: 100 |
| b05104g | GATCAACCCGGAGAGGAAT | SEQ ID NO: 101 |
| b05104h | CCATGACGGGTTTGAGAT | SEQ ID NO: 102 |
| b05105c | CAACCGACCTGACAAGTGAC | SEQ ID NO: 103 |
| b05105e | ATCTCAAACCCGTCATGG | SEQ ID NO: 104 |
| b05105f | ATTCCTCTCCGGGTTGATC | SEQ ID NO: 105 |

Example 6. Detection of Vip3Aa20 Protein in MIR162 by ELISA

Extracts were prepared from MIR162 leaves, roots, pith, kernels, silk, pollen and whole plants. They were quantitatively analyzed for Vip3Aa20 by ELISA using immunoaffinity purified goat anti-Vip3A and Protein A-purified rabbit anti-Vip3A polyclonal antibodies using art recognized ELISA procedures. Vip3Aa20 was detected in all tissues analyzed across all growth stages. The mean level of Vip3Aa20 protein detected in the whole plant at anthesis and seed maturity was 10 µg/g fresh weight and 16 µg/g fresh weight, respectively. The mean level of Vip3Aa20 protein in leaves at anthesis was 22 µg/g fresh weight.

Example 7. Field Efficacy of MIR162

The MIR162 event was tested in the field for efficacy against fall armyworm (FAW, *Spodoptera frugiperda*), corn earworm (CEW, *Helicoverpa zea*), black cutworm (BCW, *Agrotis ipsilon*), and European corn borer (ECB, *Ostrinia nubilalis*). Performance of the MIR162 event was compared with that of Warrior (Syngenta, Inc.), a conventional insecticide standard applied at a rate of 11.2 g a.i./acre, the transgenic corn event Bt11, comprising a cry1Ab gene, and a Bt11×MIR162 hybrid, produced by crossing a Bt11 inbred line with a MIR162 inbred line.

Twenty-eight trials were planted in 13 states that represented the major corn growing regions of the continental United States. Trials were planted in a randomized complete block design with four replicated plots per block. Plots were 17.5 row feet per treatment per replication. Planting density was targeted at approximately 30,000 plants/acre. Immunodiagnostic strips were used to confirm the presence or absence of the Vip3Aa20 and Cry1Ab proteins in the different treatment groups.

Natural pest infestations were utilized in trials where populations were sufficiently high; where they were not, artificial infestations were carried out. Artificial infestation with two $2^{nd}$- to $3^{rd}$-instar larvae at V1-V2 was utilized in the BCW trials. Plots were rated at 3, 7, and 14 days post-infestation. BCW damage was recorded as partially damaged plants and fully cut plants. FAW plots were rated 7 and 14 days post-infestation or after $3^{rd}$-instar larvae were observed in control plants. The following scale was used to evaluate FAW and CEW leaf damage:

0.01—No visible leaf damage
    1—Pin-hole damage on a few leaves
    2—Small amount of shot-hole damage on a few leaves
    3—Shot-hole damage on several leaves
    4—Shot-hole damage and lesions on a few leaves
    5—Lesions on several leaves
    6—Large lesions on several leaves
    7—Large lesions and portions eaten away on a few leaves
    8—Large lesions and portions eaten away on several leaves
    9—Large lesions and portions eaten away on most leaves Plant damage was assessed for both first and second generation ECB. The following scale was used for rating first generation damage, typically when larvae were in the $3^{rd}$ to 4th instar:

1—No visible leaf damage
    2—Small amount of shot-hole injury on a few leaves
    3-Shot-hole injury common on several leaves
    4—Several leaves with shot-holes and elongated lesions
    5—Several leaves with elongated lesions
    6—Several leaves with elongated lesions about 2.5 cm
    7—Long lesions common on about one half of the leaves
    8—Long lesions common on about two-thirds of the leaves
    9—Most leaves with long lesions Second generation ECB damage was assessed three to four weeks after artificial infestation or the end of the peak egg laying period. The following measurements were taken: number live larvae/stalk, number live larvae/shank, number live larvae/ear, number of tunnels/stalk, cumulative tunnel length (cm)/stalk, cumulative tunnel length (cm)/shank, number tunnels/ear, cumulative tunnel length kernel damage (cm)/ear, and % infested plants.

CEW trials were generally planted late to increase natural infestation levels. Feeding damage to ears was evaluated when CEW larvae on control plants were at the L5-L6 growth stage. Ear ratings included recording the number of larvae observed per ear and length of visible kernel feeding measured from the ear tip to the average lowest kernel destroyed.

Results of the BCW field trial are shown in Table 6. Less than 3% of the MIR162 plants and Bt11×MIR162 plants were cut by BCW larvae. Significant numbers of Bt11 and control plants were cut. Plants comprising the MIR162 genotype had less BCW feeding damage than the conventional insecticide treated plants.

TABLE 6

Stalk damage ratings from five trials with BCW at 21 days after infestation. Damage was measured as percent of total plants cut.

| Treatment | % Cut Plants |
| --- | --- |
| MIR162 | 2 |
| Bt11 | 42 |
| Bt11 X MIR162 | 3 |
| Warrior Insecticide | 12 |
| Negative Control | 40 |

The FAW field trial results are shown in Table 7. FAW feeding damage was measured on a scale of 0.01 to 9. Mean feeding damage in the MIR162 hybrids was very low (<1) and significantly lower than average damage observed in the Bt11 and conventional insecticide treatments. Insect pressure in these trials was heavy with approximately 50 to 100 neonate larvae/plant. Bt11 provided some protection from damage, whereas the conventional insecticide treatment provided no protection, sustaining the same amount of damage as the control.

TABLE 7

Leaf feeding damage ratings from five trials for FAW. Mean damage ratings at 14 days after infestation are presented for each treatment.

| Treatment | Mean Leaf Damage Rating (0.01-9) |
| --- | --- |
| MIR162 | 0.90 |
| Bt11 | 2.52 |
| Bt11 X MIR162 | 0.84 |
| Warrior Insecticide | 3.60 |
| Negative Control | 3.78 |

Results of the trials to assess first generation ECB damage are presented in Table 8. ECB feeding damage was rated on a scale of 1-9. In these trials, MIR162 conferred minimal protection against ECB feeding damage. Bt11 fully protected the plants from ECB feeding damage. The Bt11× MIR162 plants had the same level of protection as the Bt11 plants. The conventional insecticide treatment provided better protection than the MIR162 trait but significantly less protection than that provided by Bt11.

TABLE 8

Leaf feeding damage field trial. Mean damage ratings at 14 days after infestation.

| Treatment | Mean Leaf Damage Rating (1-9) |
| --- | --- |
| MIR162 | 2.95 |
| Bt11 | 1.00 |
| Bt11 X MIR162 | 1.00 |
| Warrior Insecticide | 2.05 |
| Negative Control | 3.88 |

Second generation ECB damage results are presented in Table 9. Feeding damaged was measured as cumulative tunnel length in each corn stalk (if more than one tunnel was found, tunnel lengths were summed). The Bt11 and Bt11× MIR162 treatments provided strong protection against stalk boring, whereas no protection against tunneling was provided by MIR162 alone or the insecticide treatment.

TABLE 9

Stalk damage ratings from seven trials for second generation ECB larvae measured in tunnel length (cm) per stalk. Measurements were taken three to four weeks after artificial infestation.

| Treatment | Mean Tunnel Length (cm) |
| --- | --- |
| MIR162 | 5.46 |
| Bt11 | 0.37 |
| Bt11 X MIR162 | 0.48 |
| Warrior Insecticide | 5.06 |
| Negative Control | 5.04 |

Results of trials to assess CEW damage are presented in Table 10. Feeding damage was rated as length of kernel damage per ear, measured from the ear tip to the average lowest kernel destroyed. Significant ear damage was observed in the Bt11, insecticide, and check plots. Bt11 provided some level of protection compared to untreated check and was comparable to the protection provided by the conventional insecticide treatment. MIR162 and Bt11× MIR162 provided almost complete protection of the ears from CEW larval feeding damage.

TABLE 10

Ear damage ratings from six trials for CEW measured as average length of feeding damage. Measurements were taken when CEW larvae were L5-L6 in check plants.

| Treatment | Mean Ear Damage (cm) |
| --- | --- |
| MIR162 | 0.17 |
| Bt11 | 2.24 |
| Bt11 X MIR162 | 0.02 |
| Warrior Insecticide | 2.20 |
| Negative Control | 3.42 |

Example 8. Efficacy of MIR162 Against Western Bean Cutworm

Current commercial transgenic events producing Cry1Ab protein have not provided acceptable levels of protection against the western bean cutworm (WBCW, *Striacosta albicosta*). Therefore, MIR162 alone and stacked with other transgenic genotypes was tested for efficacy against WBCW.

WBCW eggs were collected from wild caught female moths. Larvae were fed on a meridic black cutworm diet until use in the experiments. Corn plants were field grown.

The following treatments were tested: MIR162, Bt11, MIR604, MIR162×Bt11, MIR162×MIR604, MIR604× Bt11, Force® (Syngenta, Inc.), a conventional insecticide applied at planting to a negative isoline, and two negative control isolines. MIR604 is a novel transgenic corn event that comprises a cry3A055 gene encoding a protein that is active against corn rootworm (*Diabrotica* spp.) larvae and is disclosed in US Patent Application publication No. 2005/0216970, published Sep. 29, 2005, herein incorporated by reference.

For the experiments, a two-inch piece of green silks and husk was cut from ears from field grown corn plants in each treatment and replication. The terminal brown ends of the silks were removed and the husk discarded. Approximately 1.5 inches of silks were placed in individual 14 ml plastic cups. One larva was then placed in each cup and the cups sealed. Several different stages of larvae were tested ranging from $3^{rd}$ to $6^{th}$-instars. Cups containing silks and larvae were held at natural day length and room temperature for the duration of the experiments. Larval survival was recorded after eight days. Treatments were replicated four times per experiment.

Results of the WBCW experiments are presented in Table 11. Survival of WBCW on silks from the negative isolines and the conventional insecticide treatment were nearly 100%. Survival of WBCW larvae on Bt11 and MIR604 silks, tested either alone or in combination in the same plant, was not different from survival on the negative isolines. Survival of WBCW larvae was reduced when larvae were fed silks from MIR162. The combination of MIR162×Bt11 in the same plant did not decrease survival any further than MIR162 alone. However, surprisingly, when the MIR162 transgenic genotype was stacked with the MIR604 transgenic genotype in the same plant, larval mortality significantly increased compared to MIR162 or MIR604 alone.

TABLE 11

Percent (±SE) survival of WBCW larvae on corn silks.

| Treatment | Experiment Number | | | | | | |
|---|---|---|---|---|---|---|---|
| | 1 | 2 | 3 | 4 | 5 | 6 | 7 |
| Bt11 | 75 (25) | 75 (25) | 100 (0) | 100 (0) | 100 (0) | 100 (0) | 100 (0) |
| MIR162 | 25 (25) | 0 (0) | 0 (0) | 50 (29) | 50 (29) | 50 (29) | 0 (0) |
| MIR604 | | | | | 100 (0) | 100 (0) | 100 (0) |
| MIR162xBt11 | 25 (25) | 25 (25) | 0 (0) | 0 (0) | 25 (25) | 25 (25) | 25 (25) |
| MIR162xMIR604 | | | | | 0 (0) | 25 (25) | 50 (29) |
| MIR604xBt11 | | | | | | | 75 (25) |
| Force | | | | | 100 (0) | 100 (0) | 100 (0) |
| Neg. Control #1 | 100 (0) | 75 (25) | 100 (0) | 100 (0) | 75 (25) | 100 (0) | 100 (0) |
| Neg. Control #2 | 100 (0) | 100 (0) | 100 (0) | 100 (0) | 100 (0) | 100 (0) | 100 (0) |

Example 9. Use of Event Mir162 Insertion Site for Targeted Integration in Maize

The MIR162 flanking sequences disclosed in SEQ ID NO: 46 and SEQ ID NO: 48 were used to search maize genomic databases. Identical matches to both flanking sequences where found on a BAC clone, CH201-307P5, of chromosome 5 (NCBI Accession No. AC185313) on Contig 13 (SEQ ID NO: 106). More specifically, the MIR162 insert is on chromosome 5 between a 5' molecular marker, designated herein as the Opie2 marker (nucleotides 1680-3338 of SEQ ID NO: 106), and a 3' molecular marker, designated herein as the gag marker (nucleotides 43,275-45,086 of SEQ ID NO: 106). Using this information, it was determined that the heterologous DNA inserted into MIR162 displaced 58 nucleotides of maize genomic DNA, nucleotides 25,455 to 25,512 of SEQ ID NO: 106 (also shown as SEQ ID NO: 107), which is between the 5' flanking sequence (nucleotides 1-25,454 of SEQ ID NO: 106) and the 3' flanking sequence (nucleotides 25,513-51,328 of SEQ ID NO: 106).

Consistent agronomic performance of the transgene of event MIR162 over several generations under field conditions suggests that these identified regions around the MIR162 insertion site provide good genomic locations for the targeted integration of other transgenic genes of interest. Such targeted integration overcomes the problems with so-called "positions effects," and the risk of creating a mutation in the genome upon integration of the transgene into the host. Further advantages of such targeted integration include, but are not limited to, reducing the large number of transformation events that must be screened and tested before obtaining a transgenic plant that exhibits the desired level of transgene expression without also exhibiting abnormalities resulting from the inadvertent insertion of the transgene into an important locus in the host genome. Moreover, such targeted integration allows for stacking transgenes rendering the breeding of elite plant lines with both genes more efficient.

Using the above disclosed teaching, the skilled person is able to use methods know in the art to target heterologous nucleic acids of interest to the same insertion site on chromosome 5 as that in MIR162 or to a site in close proximity to the insertion site in MIR162. One such method is disclosed in US Patent Application Publication No. 20060253918, herein incorporated by reference in its entirety. Briefly, up to 20 Kb of the genomic sequence flanking 5' to the insertion site (nucleotides 5,454 to 25,454 of SEQ ID NO: 106) and up to 20 Kb of the genomic sequence flanking 3' to the insertion site (nucleotides 25,513 to 45,513 of SEQ OD NO: 106) are used to flank the gene or genes of interest that are intended to be inserted into a genomic location on Chromosome 5 via homologous recombination. These sequences can be further flanked by T-DNA border repeats such as the left border (LB) and right border (RB) repeat sequences and other booster sequences for enhancing T-DNA delivery efficiency. The gene or genes of interest can be placed exactly as in the MIR162 insertion site or can be placed anywhere within the 20 Kb regions around the MIR162 insertion sites to confer consistent level of transgene expression without detrimental effects on the plant. The DNA vectors containing the gene or genes of interest and flanking sequences can be delivered into plant cells via one of the several methods known to those skilled in the art, including but not limited to *Agrobacterium*-mediated transformation. The insertion of the DNA vector into the MIR162 target site can be further enhanced by one of the several methods, including but not limited to the co-expression or up-regulation of recombination enhancing genes or down-regulation of endogenous recombination suppression genes. Furthermore, it is known in the art that cleavage of specific sequences in the genome can be used to increase homologous recombination frequency, therefore insertion into the MIR162 insertion site and its flanking regions can be enhanced by expression of natural or designed sequence-specific endonucleases for cleaving these sequences. Thus, using the teaching provided herein, any heterologous nucleic acid can be inserted on maize chromosome 5 at a target site located between nucleotides 25,454 and 45,513 of SEQ ID NO: 106 or a target site in the vicinity to this site.

Example 10. Use of Event MIR162 Insertion Site and Flanking Sequences for Stabilization of Gene Expression The genomic sequences flanking the MIR162 insertion site may also be used to stabilize expression of other gene(s) of interest when inserted as a transgene in other genomic locations in maize and other crops. Specifically, up to 20 Kb of the genomic sequence flanking 5' to the insertion site (nucleotides 5,454 to 25,454 of SEQ ID NO: 106) and up to 20 Kb of the genomic sequence flanking 3' to the insertion site (nucleotides 25,513 to 45,513 of SEQ OD NO: 106) are used to flank the gene or genes of interest that are intended to be inserted into the genome of plants. These sequences can be further flanked by T-DNA border repeats such as the left border (LB) and right border (RB) repeat sequences and other booster sequences for enhancing T-DNA delivery efficiency. The gene or genes of interest can be placed exactly as in the MIR162 insertion site or can be placed anywhere within the 20 Kb regions around the MIR162 insertion sites to confer consistent level of transgene expression. The DNA vectors containing the gene or genes of interest and MIR162 insertion site flanking sequence can be delivered into plant cells via one of the several methods known to those skilled in the art, including but not limited to protoplast transformation, biolistic bombardment and *Agrobacterium*-mediated transformation. The delivered DNA can be integrated randomly into a plant genome or can also be present as part of the independently segregating genetic units such as artificial chromosome or mini-chromosome. The DNA vectors containing the gene(s) of interest and the MIR162 insertion site flanking sequences can be delivered into plant cells. Thus, by surrounding a gene or genes of interest with the genomic sequence flanking the MIR162 insertion site, the expression of such genes are stabilized in a transgenic host plant such as a dicot plant or a monocot plant like corn.

DEPOSIT

Applicants have made a deposit of corn seed of event MIR162 disclosed above on 23 Jan. 2007 in accordance with the Budapest Treaty at the American Type Culture Collection (ATCC), 1801 University Boulevard, Manassas, Va. 20110 under ATCC Accession No. PTA-8166. The deposit will be maintained in the depositary for a period of 30 years, or 5 years after the last request, or the effective life of the patent, whichever is longer, and will be replaced as necessary during that period. Applicants impose no restrictions on the availability of the deposited material from the ATCC; however, Applicants have no authority to waive any restrictions imposed by law on the transfer of biological material or its transportation in commerce. Applicants do not waive any infringement of their rights granted under this patent or under the Plant Variety Protection Act (7 USC 2321 et seq.).

All publications and published patent documents cited in this specification are incorporated herein by reference to the same extent as if each individual publication or patent document was specifically and individually indicated to be incorporated by reference.

What is claimed is:

1. A method of detecting the presence of a nucleic acid molecule that is unique to event MIR162 in a sample comprising corn nucleic acids, the method comprising:
   (a) contacting the sample with a pair of primers that, when used in a nucleic-acid amplification reaction with genomic DNA from event MIR162 produces an amplicon that is diagnostic for event MIR162;
   (b) performing a nucleic acid amplification reaction, thereby producing the amplicon; and
   (c) detecting the amplicon.

2. A method of detecting the presence of a nucleic acid molecule that is unique to event MIR162 in a sample comprising corn nucleic acids, the method comprising:
   (a) contacting the sample with a probe that hybridizes under high stringency conditions with genomic DNA from event MIR162 and does not hybridize under high stringency conditions with DNA of a control corn plant, wherein the probe comprises the nucleotide sequence of SEQ ID NO: 45 or SEQ ID NO: 47;
   (b) subjecting the sample and probe to high stringency hybridization conditions; and
   (c) detecting hybridization of the probe to the nucleic acid molecule.

3. An amplicon diagnostic for event MIR162, wherein said amplicon is at least 20 nucleotides in length and comprises the nucleic acid sequence of SEQ ID NO: 45, SEQ ID NO: 47, the nucleotide of position 387 of SEQ ID NO: 1 or the nucleotide of position 1683 of SEQ ID NO: 1.

4. A pair of polynucleotide primers comprising a first polynucleotide primer and a second polynucleotide primer which function together in the presence of an event MIR162 DNA template in a sample to produce an amplicon diagnostic for event MIR162, wherein said first primer and second primer comprise at least 10 contiguous nucleotides of SEQ ID NO: 1 and wherein said amplicon is at least 20 nucleotides in length and comprises the nucleotide of position 387 of SEQ ID NO: 1 and/or position 1683 of SEQ ID NO: 1.

5. A method of detecting the presence of a nucleic acid molecule that is unique to event MIR162 in a sample comprising corn nucleic acids, the method comprising:
   (a) contacting the sample with a pair of primers of claim 4 that, when used in a nucleic-acid amplification reaction with genomic DNA from event MIR162 produces an amplicon that is diagnostic for event MIR162;
   (b) performing a nucleic acid amplification reaction, thereby producing the amplicon; and
   (c) detecting the amplicon.

* * * * *

UNITED STATES PATENT AND TRADEMARK OFFICE
CERTIFICATE OF CORRECTION

PATENT NO. : 9,752,198 B2  
APPLICATION NO. : 13/939954  
DATED : September 5, 2017  
INVENTOR(S) : Long et al.

Page 1 of 1

It is certified that error appears in the above-identified patent and that said Letters Patent is hereby corrected as shown below:

On the Title Page

In Item (62), the phrase "Division of application No. 13/534,202, filed on Jun. 27, 2012, now Pat. No. 8,618,272, which is a division of application No. 12/301,824, filed on Jul. 15, 2009, now Pat. No. 8,232,456." should read -- Division of application No. 13/534,202, filed on Jun. 27, 2012, now Pat. No. 8,618,272, which is a division of application No. 12/301,824, filed as application No. PCT/US2007/012301 on May 24, 2007, now Pat. No. 8,232,456. --

Signed and Sealed this  
Twenty-fourth Day of January, 2023

Katherine Kelly Vidal  
*Director of the United States Patent and Trademark Office*

SEQUENCE LISTING

```
<160> NUMBER OF SEQ ID NOS: 107

<210> SEQ ID NO 1
<211> LENGTH: 2370
<212> TYPE: DNA
<213> ORGANISM: Artificial Sequence
<220> FEATURE:
<223> OTHER INFORMATION: vip3Aa20 coding sequence

<400> SEQUENCE: 1
atgaacaaga acaacaccaa gctgagcacc cgcgccctgc cgagcttcat cgactacttc      60
aacggcatct acggcttcgc caccggcatc aaggacatca tgaacatgat cttcaagacc     120
gacaccggcg gcgacctgac cctggacgag atcctgaaga accagcagct gctgaacgac     180
atcagcggca agctggacgg cgtgaacggc agcctgaacg acctgatcgc ccagggcaac     240
ctgaacaccg agctgagcaa ggagatcctt aagatcgcca acgagcagaa ccaggtgctg     300
aacgacgtga acaacaagct ggacgccatc aacaccatgc tgcgcgtgta cctgccgaag     360
atcaccagca tgctgagcga cgtgattaag cagaactacg ccctgagcct gcagatcgag     420
tacctgagca agcagctgca ggagatcagc gacaagctgg acatcatcaa cgtgaacgtc     480
ctgatcaaca gcaccctgac cgagatcacc ccggcctacc agcgcatcaa gtacgtgaac     540
gagaagttcg aagagctgac cttcgccacc gagaccagca gcaaggtgaa gaaggacggc     600
agcccggccg acatcctgga cgagctgacc gagctgaccg agctggcgaa gagcgtgacc     660
aagaacgacg tggacggctt cgagttctac ctgaacacct ccacgacgt gatggtgggc     720 aacaacctgt tcggccgcag cgccctgaag accgccagcg agctgatcac caaggagaac     780
gtgaagacca gcggcagcga ggtgggcaac gtgtacaact tcctgatcgt gctgaccgcc     840
ctgcaggccc aggccttcct gacgctgacc acctgtcgca agctgctggg cctggccgac     900
```

```
atcgactaca ccagcatcat gaacgagcac ttgaacaagg agaaggagga gttccgcgtg    960
aacatcctgc cgaccctgag caacaccttc agcaacccga actacgccaa ggtgaagggc   1020
agcgacgagg acgccaagat gatcgtggag gctaagccgg ccacgcgtt gatcggcttc    1080
gagatcagca acgacagcat caccgtgctg aaggtgtacg aggccaagct gaagcagaac   1140
taccaggtgg acaaggacag cttgagcgag gtgatctacg cgacatgga caagctgctg    1200
tgtccggacc agagcgagca aatctactac accaacaaca tcgtgttccc gaacgagtac   1260
gtgatcacca agatcgactt caccaagaag atgaagaccc tgcgctacga ggtgaccgcc   1320
aacttctacg acagcagcac cggcgagatc gacctgaaca agaagaaggt ggagagcagc   1380
gaggccgagt accgcaccct gagcgcgaac gacgacggcg tctacatgcc actgggcgtg   1440
atcagcgaga ccttcctgac cccgatcaac ggctttggcc tgcaggccga cgagaacagc   1500
cgcctgatca ccctgacctg taagagctac ctgcgcgagc tgctgctagc caccgacctg   1560
agcaacaagg agaccaagct gatcgtgcca ccgagcggct tcatcagcaa catcgtggag   1620
aacggcagca tcgaggagga caacctggag ccgtggaagg ccaacaacaa gaacgcctac   1680
gtcgaccaca ccggcggcgt gaacggcacc aaggccctgt acgtgcacaa ggacggcggc   1740
atcagccagt tcatcggcga caagctgaag ccgaagaccg agtacgtgat ccagtacacc   1800
gtgaagggca agccatcgat tcacctgaag gacgagaaca ccggctacat ccactacgag   1860
gacaccaaca caacctggga ggactaccag accatcaaca agcgcttcac caccggcacc   1920
gacctgaagg gcgtgtacct gatcctgaag agccagaacg gcgacgaggc ctggggcgac   1980
aacttcatca tcctggagat cagcccgagc gagaagctgc tgagcccgga gctgatcaac   2040
accaacaact ggaccagcac cggcagcacc aacatcagcg gcaacaccct gaccctgtac   2100
cagggcggcc gcggcatcct gaagcagaac ctgcagctgg acagcttcag cacctaccgc   2160
gtgtacttca gcgtgagcgg cgacgccaac gtgcgcatcc gcaactcccg cgaggtgctg   2220
ttcgagaaga ggtacatgag cggcgccaag gacgtgagcg agatgttcac caccaagttc   2280
gagaaggaca acttctacat cgagctgagc cagggcaaca acctgtacgg cggcccgatc   2340
gtgcacttct acgacgtgag catcaagtag                                    2370
```

<210> SEQ ID NO 2
<211> LENGTH: 789
<212> TYPE: PRT
<213> ORGANISM: Artificial Sequence
<220> FEATURE:
<223> OTHER INFORMATION: Vip3Aa toxin
<220> FEATURE:
<221> NAME/KEY: MISC_FEATURE
<222> LOCATION: (1)..(789)
<223> OTHER INFORMATION: Vip3Aa20 protein produced by MIR162

<400> SEQUENCE: 2

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

```
Leu Asn Thr Glu Leu Ser Lys Glu Ile Leu Lys Ile Ala Asn Glu Gln
                 85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
            115                 120                 125

Ile Lys Gln Asn Tyr Ala Leu Ser Leu Gln Ile Glu Tyr Leu Ser Lys
            130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
            195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Ser Glu Val Gly Asn Val Tyr
            260                 265                 270

Asn Phe Leu Ile Val Leu Thr Ala Leu Gln Ala Gln Ala Phe Leu Thr
            275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
            355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
            435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
```

-continued

```
            500             505             510
Glu Leu Leu Leu Ala Thr Asp Leu Ser Asn Lys Glu Thr Lys Leu Ile
            515             520             525

Val Pro Pro Ser Gly Phe Ile Ser Asn Ile Val Glu Asn Gly Ser Ile
        530             535             540

Glu Glu Asp Asn Leu Glu Pro Trp Lys Ala Asn Asn Lys Asn Ala Tyr
545             550             555             560

Val Asp His Thr Gly Gly Val Asn Gly Thr Lys Ala Leu Tyr Val His
            565             570             575

Lys Asp Gly Gly Ile Ser Gln Phe Ile Gly Asp Lys Leu Lys Pro Lys
        580             585             590

Thr Glu Tyr Val Ile Gln Tyr Thr Val Lys Gly Lys Pro Ser Ile His
            595             600             605

Leu Lys Asp Glu Asn Thr Gly Tyr Ile His Tyr Glu Asp Thr Asn Asn
            610             615             620

Asn Leu Glu Asp Tyr Gln Thr Ile Asn Lys Arg Phe Thr Thr Gly Thr
625             630             635             640

Asp Leu Lys Gly Val Tyr Leu Ile Leu Lys Ser Gln Asn Gly Asp Glu
            645             650             655

Ala Trp Gly Asp Asn Phe Ile Ile Leu Glu Ile Ser Pro Ser Glu Lys
            660             665             670

Leu Leu Ser Pro Glu Leu Ile Asn Thr Asn Asn Trp Thr Ser Thr Gly
        675             680             685

Ser Thr Asn Ile Ser Gly Asn Thr Leu Thr Leu Tyr Gln Gly Gly Arg
    690             695             700

Gly Ile Leu Lys Gln Asn Leu Gln Leu Asp Ser Phe Ser Thr Tyr Arg
705             710             715             720

Val Tyr Phe Ser Val Ser Gly Asp Ala Asn Val Arg Ile Arg Asn Ser
            725             730             735

Arg Glu Val Leu Phe Glu Lys Arg Tyr Met Ser Gly Ala Lys Asp Val
            740             745             750

Ser Glu Met Phe Thr Thr Lys Phe Glu Lys Asp Asn Phe Tyr Ile Glu
        755             760             765

Leu Ser Gln Gly Asn Asn Leu Tyr Gly Gly Pro Ile Val His Phe Tyr
    770             775             780

Asp Val Ser Ile Lys
785

<210> SEQ ID NO 3
<211> LENGTH: 14405
<212> TYPE: DNA
<213> ORGANISM: Artificial Sequence
<220> FEATURE:
<223> OTHER INFORMATION: Plasmid pNOV1300

<400> SEQUENCE: 3
atgaacaaga caacaccaa gctgagcacc cgcgccctgc cgagcttcat cgactacttc      60
aacggcatct acggcttcgc caccggcatc aaggacatca tgaacatgat cttcaagacc     120
gacaccggcg cgacctgac cctggacgag atcctgaaga ccagcagct gctgaacgac     180 atcagcggca agctggacgg cgtgaacggc agcctgaacg acctgatcgc ccagggcaac     240
ctgaacaccg agctgagcaa ggagatcctt aagatcgcca acgagcagaa ccaggtgctg     300
aacgacgtga caacaagct ggacgccatc aacaccatgc tgcgcgtgta cctgccgaag     360
atcaccagca tgctgagcga cgtgatgaag cagaactacg ccctgagcct gcagatcgag     420
```

```
tacctgagca agcagctgca ggagatcagc gacaagctgg acatcatcaa cgtgaacgtc     480
ctgatcaaca gcaccctgac cgagatcacc ccggcctacc agcgcatcaa gtacgtgaac     540
gagaagttcg aagagctgac cttcgccacc gagaccagca gcaaggtgaa gaaggacggc     600
agcccggccg acatcctgga cgagctgacc gagctgaccg agctggcgaa gagcgtgacc     660
aagaacgacg tggacggctt cgagttctac ctgaacacct tccacgacgt gatggtgggc     720
aacaacctgt tcggccgcag cgccctgaag accgccagcg agctgatcac caaggagaac     780
gtgaagacca gcggcagcga ggtgggcaac gtgtacaact tcctgatcgt gctgaccgcc     840
ctgcaggccc aggccttcct gaccctgacc acctgtcgca agctgctggg cctggccgac     900
atcgactaca ccagcatcat gaacgagcac ttgaacaagg agaaggagga gttccgcgtg     960
aacatcctgc cgaccctgag caacaccttc agcaacccga actacgccaa ggtgaagggc    1020
agcgacgagg acgccaagat gatcgtggag gctaagccgg ccacgcgtt gatcggcttc     1080 gagatcagca cgacagcat caccgtgctg aaggtgtacg aggccaagct gaagcagaac     1140
taccaggtgg acaaggacag cttgagcgag gtgatctacg gcgacatgga caagctgctg    1200
tgtccggacc agagcgagca aatctactac accaacaaca tcgtgttccc gaacgagtac    1260
gtgatcacca agatcgactt caccaagaag atgaagaccc tgcgctacga ggtgaccgcc    1320
aacttctacg acagcagcac cggcgagatc gacctgaaca agaagaaggt ggagagcagc    1380
gaggccgagt accgcaccct gagcgcgaac gacgacggcg tctacatgcc actgggcgtg    1440
atcagcgaga ccttcctgac cccgatcaac ggctttggcc tgcaggccga cgagaacagc    1500
cgcctgatca ccctgacctg taagagctac ctgcgcgagc tgctgctagc caccgacctg    1560
agcaacaagg agaccaagct gatcgtgcca ccgagcggct tcatcagcaa catcgtggag    1620
aacggcagca tcgaggagga caacctggag ccgtggaagg ccaacaacaa gaacgcctac    1680
gtggaccaca ccggcggcgt gaacggcacc aaggccctgt acgtgcacaa ggacggcggc    1740
atcagccagt tcatcggcga caagctgaag ccgaagaccg agtacgtgat ccagtacacc    1800
gtgaagggca agccatcgat tcacctgaag gacgagaaca ccggctacat ccactacgag    1860
gacaccaaca acaacctgga ggactaccag accatcaaca gcgcttcac caccggcacc     1920 gacctgaagg gcgtgtacct gatcctgaag agccagaacg cgacgaggc ctggggcgac     1980 aacttcatca tcctggagat cagcccgagc gagaagctgc tgagcccgga gctgatcaac    2040
accaacaact ggaccagcac cggcagcacc aacatcagcg gcaacaccct gaccctgtac    2100
cagggcggcc gcggcatcct gaagcagaac ctgcagctgg acagcttcag cacctaccgc    2160
gtgtacttca gcgtgagcgg cgacgccaac gtgcgcatcc gcaactcccg cgaggtgctg    2220
ttcgagaaga ggtacatgag cggcgccaag gacgtgagcg agatgttcac caccaagttc    2280
gagaaggaca acttctacat cgagctgagc cagggcaaca acctgtacgg cggcccgatc    2340
gtgcacttct acgacgtgag catcaagtag gagctctaga tctgttctgc acaaagtgga    2400
gtagtcagtc atcgatcagg aaccagacac cagacttta ttcatacagt gaagtgaagt     2460
gaagtgcagt gcagtgagtt gctggtttt gtacaactta gtatgtattt gtatttgtaa     2520
aatacttcta tcaataaaat ttctaattcc taaaaccaaa atccaggggt accagcttgc    2580
atgcctgcag tgcagcgtga cccggtcgtg cccctctcta gagataatga gcattgcatg    2640
tctaagttat aaaaaattac cacatatttt ttttgtcaca cttgtttgaa gtgcagttta    2700
tctatcttta tacatatatt taaactttac tctacgaata atataatcta tagtactaca    2760
```

```
ataatatcag tgttttagag aatcatataa atgaacagtt agacatggtc taaaggacaa    2820
ttgagtattt tgacaacagg actctacagt tttatctttt tagtgtgcat gtgttctcct    2880 tttttttgc aaatagcttc acctatataa tacttcatcc attttattag tacatccatt     2940
tagggtttag ggttaatggt ttttatagac taattttttt agtacatcta ttttattcta    3000
ttttagcctc taaattaaga aaactaaaac tctattttag tttttttatt taataattta    3060
gatataaaat agaataaaat aaagtgacta aaaattaaac aaatacccott taagaaatta   3120 aaaaaactaa ggaaacattt ttcttgtttc gagtagataa tgccagcctg ttaaacgccg    3180
tcgacgagtc taacggacac caaccagcga accagcagcg tcgcgtcggg ccaagcgaag    3240
cagacggcac ggcatctctg tcgctgcctc tggacccctc tcgagagttc cgctccaccg    3300
ttggacttgc tccgctgtcg gcatccagaa attgcgtggc ggagcggcag acgtgagccg    3360
gcacggcagg cggcctcctc ctcctctcac ggcaccggca gctacggggg attcctttcc    3420
caccgctcct tcgctttccc ttcctcgccc gccgtaataa atagacaccc cctccacacc    3480
ctctttcccc aacctcgtgt tgttcggagc gcacacacac acaaccagat ctcccccaaa    3540
tccacccgtc ggcacctccg cttcaaggta cgccgctcgt cctcccccccc ccccctctc   3600 taccttctct agatcggcgt tccggtccat ggttagggcc cggtagttct acttctgttc    3660
atgtttgtgt tagatccgtg tttgtgttag atccgtgctg ctagcgttcg tacacggatg    3720
cgacctgtac gtcagacacg ttctgattgc taacttgcca gtgtttctct ttggggaatc    3780
ctgggatggc tctagccgtt ccgcagacgg gatcgatttc atgattttt ttgtttcgtt     3840 gcatagggtt tggtttgccc ttttcccttta tttcaatata tgccgtgcac ttgtttgtcg    3900
ggtcatcttt tcatgctttt ttttgtcttg gttgtgatga tgtggtctgg ttgggcggtc    3960
gttctagatc ggagtagaat tctgtttcaa actacctggt ggatttatta attttggatc    4020
tgtatgtgtg tgccatacat attcatagtt acgaattgaa gatgatggat ggaaatatcg    4080
atctaggata ggtatacatg ttgatgcggg ttttactgat gcatatacag agatgctttt    4140
tgttcgcttg gttgtgatga tgtggtgtgg ttgggcggtc gttcattcgt tctagatcgg    4200 agtagaaatac tgtttcaaac tacctggtgt atttattaat tttggaactg tatgtgtgtg    4260
tcatacatct tcatagttac gagtttaaga tggatggaaa tatcgatcta ggataggtat    4320
acatgttgat gtgggtttta ctgatgcata tacatgatgg catatgcagc atctattcat    4380
atgctctaac cttgagtacc tatctattat aataaacaag tatgttttat aattattttg    4440
atcttgatat acttggatga tggcatatgc agcagctata tgtggatttt tttagccctg    4500
ccttcatacg ctatttattt gcttggtact gtttcttttg tcgatgctca ccctgttgtt    4560
tggtgttact tctgcaggga tccccgatca tgcaaaaact cattaactca gtgcaaaact    4620
atgcctgggg cagcaaaacg gcgttgactg aactttatgg tatggaaaat ccgtccagcc    4680
agccgatggc cgagctgtgg atgggcgcac atccgaaaag cagttcacga gtgcagaatg    4740
ccgccggaga tatcgtttca ctgcgtgatg tgattgagag tgataaatcg actctgctcg    4800
gagaggccgt tgccaaacgc tttggcgaac tgccttttcct gttcaaagta ttatgcgcag    4860
cacagccact ctccattcag gttcatccaa acaaacacaa ttctgaaatc ggttttgcca    4920
aagaaaatgc cgcaggtatc ccgatggatg ccgccgagcg taactataaa gatcctaacc    4980
acaagccgga gctggttttt gcgctgacgc ctttccttgc gatgaacgcg tttcgtgaat    5040
tttccgagat tgtctcccta ctccagccgg tcgcaggtgc acatccggcg attgctcact    5100
ttttacaaca gcctgatgcc gaacgtttaa gcgaactgtt cgccagcctg ttgaatatgc    5160
```

```
agggtgaaga aaaatcccgc gcgctggcga ttttaaaatc ggccctcgat agccagcagg   5220
gtgaaccgtg gcaaacgatt cgtttaattt ctgaatttta cccggaagac agcggtctgt   5280
tctccccgct attgctgaat gtggtgaaat tgaaccctgg cgaagcgatg ttcctgttcg   5340
ctgaaacacc gcacgcttac ctgcaaggcg tggcgctgga agtgatggca aactccgata   5400
acgtgctgcg tgcgggtctg acgcctaaat acattgatat tccggaactg gttgccaatg   5460
tgaaattcga agccaaaccg gctaaccagt tgttgaccca gccggtgaaa caaggtgcag   5520
aactggactt cccgattcca gtggatgatt ttgccttctc gctgcatgac cttagtgata   5580
aagaaaccac cattagccag cagagtgccg ccattttgtt ctgcgtcgaa ggcgatgcaa   5640
cgttgtggaa aggttctcag cagttacagc ttaaaccggg tgaatcagcg tttattgccg   5700
ccaacgaatc accggtgact gtcaaaggcc acggccgttt agcgcgtgtt acaacaagc   5760 tgtaagagct tactgaaaaa attaacatct cttgctaagc tgggagctcg atccgtcgac   5820
ctgcagatcg ttcaaacatt tggcaataaa gtttcttaag attgaatcct gttgccggtc   5880
ttgcgatgat tatcatataa tttctgttga attacgttaa gcatgtaata attaacatgt   5940
aatgcatgac gttatttatg agatgggttt ttatgattag agtcccgcaa ttatacattt   6000
aatacgcgat agaaaacaaa atatagcgcg caaactagga taaattatcg cgcgcggtgt   6060
catctatgtt actagatccc cgggtctaga caattcagta cattaaaaac gtccgcaatg   6120
tgttattaag ttgtctaagc gtcaatttgt ttacaccaca atatatcctg ccaccagcca   6180
gccaacagct ccccgaccgg cagctcggca caaaatcacc actcgataca ggcagcccat   6240
cagtccggga cggcgtcagc gggagagccg ttgtaaggcg gcagactttg ctcatgttac   6300
cgatgctatt cggaagaacg gcaactaagc tgccgggttt gaaacacgga tgatctcgcg   6360
gagggtagca tgttgattgt aacgatgaca gagcgttgct gcctgtgatc aaatatcatc   6420
tccctcgcag agatccgaat tatcagcctt cttattcatt tctcgcttaa ccgtgacagg   6480
ctgtcgatct tgagaactat gccgacataa taggaaatcg ctggataaag ccgctgagga   6540
agctgagtgg cgctatttct ttagaagtga acgttgacga tcgtcgaccg taccccgatg   6600
aattaattcg gacgtacgtt ctgaacacag ctggatactt acttgggcga ttgtcataca   6660
tgacatcaac aatgtacccg tttgtgtaac cgtctcttgg aggttcgtat gacactagtg   6720
gttcccctca gcttgcgact agatgttgag gcctaacatt ttattagaga gcaggctagt   6780
tgcttagata catgatcttc aggccgttat ctgtcagggc aagcgaaaat tggccattta   6840
tgacgaccaa tgccccgcag aagctcccat ctttgccgcc atagacgccg cgcccccctt   6900
ttggggtgta gaacatcctt ttgccagatg tggaaaagaa gttcgttgtc ccattgttgg   6960
caatgacgta gtagccggcg aaagtgcgag acccatttgc gctatatata agcctacgat   7020
ttccgttgcg actattgtcg taattggatg aactattatc gtagttgctc tcagagttgt   7080
cgtaatttga tggactattg tcgtaattgc ttatggagtt gtcgtagttg cttggagaaa   7140
tgtcgtagtt ggatggggag tagtcatagg gaagacgagc ttcatccact aaaacaattg   7200
gcaggtcagc aagtgcctgc cccgatgcca tcgcaagtac gaggcttaga accaccttca   7260
acagatcgcg catagtcttc cccagctctc taacgcttga gttaagccgc gccgcgaagc   7320
ggcgtcggct tgaacgaatt gttagacatt atttgccgac taccttggtg atctcgcctt   7380
tcacgtagta aacaaattct tccaactgat ctgcgcgcga ggccaagcga tcttcttgtc   7440
caagataagc ctgcctagct tcaagtatga cgggctgata ctgggccggc aggcgctcca   7500
```

```
ttgcccagtc ggcagcgaca tccttcggcg cgattttgcc ggttactgcg ctgtaccaaa    7560
tgcgggacaa cgtaagcact acatttcgct catcgccagc ccagtcgggc ggcgagttcc    7620
atagcgttaa ggtttcattt agcgcctcaa atagatcctg ttcaggaacc ggatcaaaga    7680
gttcctccgc cgctggacct accaaggcaa cgctatgttc tcttgctttt gtcagcaaga    7740
tagccagatc aatgtcgatc gtggctggct cgaagatacc tgcaagaatg tcattgcgct    7800
gccattctcc aaattgcagt tcgcgcttag ctggataacg ccacggaatg atgtcgtcgt    7860
gcacaacaat ggtgacttct acagcgcgga gaatctcgct ctctccaggg gaagccgaag    7920
tttccaaaag gtcgttgatc aaagctcgcc gcgttgtttc atcaagcctt acggtcaccg    7980
taaccagcaa atcaatatca ctgtgtggct tcaggccgcc atccactgcg gagccgtaca    8040
aatgtacggc cagcaacgtc ggttcgagat ggcgctcgat gacgccaact acctctgata    8100
gttgagtcga tacttcggcg atcaccgctt ccctcatgat gtttaactcc tgaattaagc    8160
cgcgccgcga agcggtgtcg gcttgaatga attgttaggc gtcatcctgt gctcccgaga    8220
accagtacca gtacatcgct gtttcgttcg agacttgagg tctagtttta tacgtgaaca    8280
ggtcaatgcc gccgagagta aagccacatt ttgcgtacaa attgcaggca ggtacattgt    8340
tcgtttgtgt ctctaatcgt atgccaagga gctgtctgct tagtgccacc tttttcgcaa    8400
attcgatgag actgtgcgcg actccttttgc ctcggtgcgt gtgcgacaca acaatgtgtt    8460
cgatagaggc tagatcgttc catgttgagt tgagttcaat cttcccgaca agctcttggt    8520
cgatgaatgc gccatagcaa gcagagtctt catcagagtc atcatccgag atgtaatcct    8580
tccggtaggg gctcacactt ctggtagata gttcaaagcc ttggtcggat aggtgcacat    8640
cgaacacttc acgaacaatg aaatggttct cagcatccaa tgtttccgcc acctgctcag    8700
ggatcaccga aatcttcata tgacgcctaa cgcctggcac agcggatcgc aaacctggcg    8760
cggcttttgg cacaaaaggc gtgacaggtt tgcgaatccg ttgctgccac ttgttaaccc    8820
ttttgccaga tttggtaact ataatttatg ttagaggcga agtcttgggt aaaaactggc    8880
ctaaaattgc tggggatttc aggaaagtaa acatcacctt ccggctcgat gtctattgta    8940
gatatatgta gtgtatctac ttgatcgggg gatctgctgc ctcgcgcgtt cggtgatga    9000 cggtgaaaac ctctgacaca tgcagctccc ggagacggtc acagcttgtc tgtaagcgga    9060
tgccgggagc agacaagccc gtcagggcgc gtcagcgggt gttggcgggt gtcggggcgc    9120
agccatgacc cagtcacgta gcgatagcgg agtgtatact ggcttaacta tgcggcatca    9180
gagcagattg tactgagagt gcaccatatg cggtgtgaaa taccgcacag atgcgtaagg    9240
agaaaatacc gcatcaggcg ctcttccgct tcctcgctca ctgactcgct gcgctcggtc    9300
gttcggctgc ggcgagcggt atcagctcac tcaaaggcgg taatacggtt atccacagaa    9360
tcaggggata acgcaggaaa gaacatgtga gcaaaaggcc agcaaaaggc caggaaccgt    9420
aaaaaggccg cgttgctggc gtttttccat aggctccgcc cccctgacga gcatcacaaa    9480
aatcgacgct caagtcagag gtggcgaaac ccgacaggac tataaagata ccaggcgttt    9540
ccccctggaa gctccctcgt gcgctctcct gttccgaccc tgccgcttac cggatacctg    9600
tccgcctttc tcccttcggg aagcgtggcg ctttctcata gctcacgctg taggtatctc    9660
agttcggtgt aggtcgttcg ctccaagctg ggctgtgtgc acgaaccccc cgttcagccc    9720
gaccgctgcg ccttatccgg taactatcgt cttgagtcca acccggtaag acacgactta    9780
tcgccactgg cagcagccac tggtaacagg attagcagag cgaggtatgt aggcggtgct    9840
acagagttct tgaagtggtg gcctaactac ggctacacta aaggacagt atttggtatc    9900
```

```
tgcgctctgc tgaagccagt taccttcgga aaaagagttg gtagctcttg atccggcaaa   9960
caaaccaccg ctggtagcgg tggttttttt gtttgcaagc agcagattac gcgcagaaaa  10020
aaaggatctc aagaagatcc tttgatcttt tctacggggt ctgacgctca gtggaacgaa  10080
aactcacgtt aagggatttt ggtcatgaga ttatcaaaaa ggatcttcac ctagatcctt  10140
ttaaattaaa aatgaagttt taaatcaatc taaagtatat atgagtaaac ttggtctgac  10200
agttaccaat gcttaatcag tgaggcacct atctcagcga tctgtctatt tcgttcatcc  10260
atagttgcct gactcccgt cgtgtagata actacgatac gggagggctt accatctggc  10320
cccagtgctg caatgatacc gcgagaccca cgctcaccgg ctccagattt atcagcaata  10380
aaccagccag ccggaagggc cgagcgcaga agtggtcctg caactttatc cgcctccatc  10440
cagtctatta attgttgccg ggaagctaga gtaagtagtt cgccagttaa tagtttgcgc  10500
aacgttgttg ccattgctgc agggggggg ggggggggt tccattgttc attccacgga  10560
caaaaacaga aaaggaaac gacagaggcc aaaaagctcg ctttcagcac ctgtcgtttc  10620 cttctttc agagggtatt ttaaataaaa acattaagtt atgacgaaga agaacggaaa  10680
cgccttaaac cggaaaattt tcataaatag cgaaaacccg cgaggtcgcc gccccgtaac  10740
ctgtcggatc accggaaagg acccgtaaag tgataatgat tatcatctac atatcacaac  10800
gtgcgtggag gccatcaaac cacgtcaaat aatcaattat gacgcaggta tcgtattaat  10860
tgatctgcat caacttaacg taaaaacaac ttcagacaat acaaatcagc gacactgaat  10920
acggggcaac ctcatgtccc ccccccccc ccccctgcag gcatcgtggt gtcacgctcg  10980
tcgtttggta tggcttcatt cagctccggt tcccaacgat caaggcgagt tacatgatcc  11040
cccatgttgt gcaaaaaagc ggttagctcc ttcggtcctc cgatcgttgt cagaagtaag  11100
ttggccgcag tgttatcact catggttatg gcagcactgc ataattctct tactgtcatg  11160
ccatccgtaa gatgcttttc tgtgactggt gagtactcaa ccaagtcatt ctgagaatag  11220
tgtatgcggc gaccgagttg ctcttgcccg gcgtcaacac gggataatac cgcgccacat  11280
agcagaactt taaaagtgct catcattgga aaacgttctt cggggcgaaa actctcaagg  11340
atcttaccgc tgttgagatc cagttcgatg taacccactc gtgcacccaa ctgatcttca  11400
gcatctttta ctttcaccag cgtttctggg tgagcaaaaa caggaaggca aaatgccgca  11460
aaaaagggaa taagggcgac acggaaatgt tgaatactca tactcttcct ttttcaatat  11520
tattgaagca tttatcaggg ttattgtctc atgagcggat acatatttga atgtatttag  11580
aaaaataaac aaataggggt tccgcgcaca tttccccgaa aagtgccacc tgacgtctaa  11640
gaaaccatta ttatcatgac attaacctat aaaaataggc gtatcacgag gccctttcgt  11700
cttcaagaat tggtcgacga tcttgctgcg ttcggatatt tcgtggagt cccgccaca  11760 gacccggatt gaaggcgaga tccagcaact cgcgccagat catcctgtga cggaactttg  11820
gcgcgtgatg actggccagg acgtcggccg aaagagcgac aagcagatca cgcttttcga  11880
cagcgtcgga tttgcgatcg aggattttc ggcgctgcgc tacgtccgcg accgcgttga  11940
gggatcaagc cacagcagcc cactcgacct tctagccgac ccagacgagc caagggatct  12000
ttttggaatg ctgctccgtc gtcaggcttt ccgacgtttg ggtggttgaa cagaagtcat  12060
tatcgcacgg aatgccaagc actcccgagg ggaaccctgt ggttggcatg cacatacaaa  12120
tggacgaacg gataaacctt ttcacgcct tttaaatatc cgattattct aataaacgct  12180
cttttctctt aggtttaccc gccaatatat cctgtcaaac actgatagtt taaactgaag  12240
```

```
gcgggaaacg acaatctgat catgagcgga gaattaaggg agtcacgtta tgacccccgc   12300
cgatgacgcg ggacaagccg ttttacgttt ggaactgaca gaaccgcaac gttgaaggag   12360
ccactcagca agctggtaca agcttgcatg cctgcagtgc agcgtgaccc ggtcgtgccc   12420
ctctctagag ataatgagca ttgcatgtct aagttataaa aaattaccac atattttttt   12480
tgtcacactt gtttgaagtg cagtttatct atctttatac atatatttaa actttactct   12540
acgaataata taatctatag tactacaata atatcagtgt tttagagaat catataaatg   12600
aacagttaga catggtctaa aggacaattg agtattttga caacaggact ctacagtttt   12660
atctttttag tgtgcatgtg ttctcctttt tttttgcaaa tagcttcacc tatataatac   12720
ttcatccatt ttattagtac atccatttag ggtttagggt taatggtttt tatagactaa   12780 ttttttttagt acatctattt tattctattt tagcctctaa attaagaaaa ctaaaactct   12840
attttagttt ttttatttaa taatttagat ataaaataga ataaaataaa gtgactaaaa   12900
attaaacaaa tacccttttaa gaaattaaaa aaactaagga acatttttc ttgtttcgag   12960 tagataatgc cagcctgtta aacgccgtcg acgagtctaa cggacaccaa ccagcgaacc   13020
agcagcgtcg cgtcgggcca agcgaagcag acggcacggc atctctgtcg ctgcctctgg   13080
acccctctcg agagttccgc tccaccgttg gacttgctcc gctgtcggca tccagaaatt   13140
gcgtggcgga gcggcagacg tgagccggca cggcaggcgg cctcctcctc ctctcacggc   13200
accggcagct acgggggatt ccttttccac cgctccttcg cttttccctt ctcgcccgcc   13260
gtaataaata gacaccccct ccacacccctc tttccccaac ctcgtgttgt tcggagcgca   13320
cacacacaca accagatctc ccccaaatcc acccgtcggc acctccgctt caaggtacgc   13380
cgctcgtcct cccccccccc ccctctctac cttctctaga tcggcgttcc ggtccatggt   13440
tagggcccgg tagttctact tctgttcatg tttgtgttag atccgtgttt gtgttagatc   13500
cgtgctgcta gcgttcgtac acggatgcga cctgtacgtc agacacgttc tgattgctaa   13560
cttgccagtg ttttctcttg gggaatcctg ggatggctct agccgttccg cagacgggat   13620
cgatttcatg attttttttg tttcgttgca tagggtttgg tttgcccttt tcctttatt    13680 caatatatgc cgtgcacttg tttgtcgggt catcttttca tgctttttt tgtcttggtt    13740 gtgatgatgt ggtctggttg ggcggtcgtt ctagatcgga gtagaattct gtttcaaact   13800
acctggtgga tttattaatt ttggatctgt atgtgtgtgc catacatatt catagttacg   13860
aattgaagat gatggatgga aatatcgatc taggataggt atacatgttg atgcgggttt   13920
tactgatgca tatacagaga tgcttttttgt tcgcttggtt gtgatgatgt ggtgtggttg   13980
ggcggtcgtt cattcgttct agatcggagt agaatactgt ttcaaactac ctggtgtatt   14040
tattaatttt ggaactgtat gtgtgtgtca tacatcttca tagttacgag tttaagatgg   14100
atggaaatat cgatctagga taggtataca tgttgatgtg ggttttactg atgcatatac   14160
atgatggcat atgcagcatc tattcatatg ctctaacctt gagtacctat ctattataat   14220
aaacaagtat gttttataat tatttgatc ttgatatact tggatgatgg catatgcagc   14280
agctatatgt ggattttttt agccctgcct tcatacgcta tttatttgct tggtactgtt   14340
tcttttgtcg atgctcaccc tgttgtttgg tgttacttct gcaggtcgac tctagaggat   14400
ccacc                                                              14405
```

<210> SEQ ID NO 4
<211> LENGTH: 21
<212> TYPE: DNA
<213> ORGANISM: Artificial Sequence

```
<220> FEATURE:
<223> OTHER INFORMATION: Chemically synthesized - vip3Aa TAQMAN primer

<400> SEQUENCE: 4
caccttcagc aacccgaact a                                              21

<210> SEQ ID NO 5
<211> LENGTH: 22
<212> TYPE: DNA
<213> ORGANISM: Artificial Sequence
<220> FEATURE:
<223> OTHER INFORMATION: Chemmicall synthesized - vip3Aa TAQMAN primer
      rev

<400> SEQUENCE: 5
gcttagcctc cacgatcatc tt                                             22

<210> SEQ ID NO 6
<211> LENGTH: 23
<212> TYPE: DNA
<213> ORGANISM: Artificial Sequence
<220> FEATURE:
<223> OTHER INFORMATION: Chemically synthesized - vip3Aa TAQMAN probe

<400> SEQUENCE: 6
gtcctcgtcg ctgcccttca cct                                            23

<210> SEQ ID NO 7
<211> LENGTH: 18
<212> TYPE: DNA
<213> ORGANISM: Artificial Sequence
<220> FEATURE:
<223> OTHER INFORMATION: Chemically synthesized - pmi TAQMAN primer for

<400> SEQUENCE: 7
ccgggtgaat cagcgttt                                                  18

<210> SEQ ID NO 8
<211> LENGTH: 18
<212> TYPE: DNA
<213> ORGANISM: Artificial Sequence
<220> FEATURE:
<223> OTHER INFORMATION: Chemically synthesized - pmi TAQMAN primer rev

<400> SEQUENCE: 8
gccgtggcct ttgacagt                                                  18

<210> SEQ ID NO 9
<211> LENGTH: 20
<212> TYPE: DNA
<213> ORGANISM: Artificial Sequence
<220> FEATURE:
<223> OTHER INFORMATION: Chemically synthesized - pmi TAQMAN probe

<400> SEQUENCE: 9
tgccgccaac gaatcaccgg                                                20

<210> SEQ ID NO 10
<211> LENGTH: 21
<212> TYPE: DNA
<213> ORGANISM: Artificial Sequence
<220> FEATURE:
<223> OTHER INFORMATION: Chemically synthesized - ZmADH-267 TAQMAN
      primer for

<400> SEQUENCE: 10
```

```
gaacgtgtgt tgggtttgca t                                              21
```

<210> SEQ ID NO 11
<211> LENGTH: 20
<212> TYPE: DNA
<213> ORGANISM: Artificial Sequence
<220> FEATURE:
<223> OTHER INFORMATION: Chemically synthesized - ZmADH-267 TAQMAN
      primer rev

<400> SEQUENCE: 11

```
tccagcaatc cttgcacctt                                                20
```

<210> SEQ ID NO 12
<211> LENGTH: 24
<212> TYPE: DNA
<213> ORGANISM: Artificial Sequence
<220> FEATURE:
<223> OTHER INFORMATION: Chemically synthesized -ZmADH-267 TAQMAN probe

<400> SEQUENCE: 12

```
tgcagcctaa ccatgcgcag ggta                                           24
```

<210> SEQ ID NO 13
<211> LENGTH: 2370
<212> TYPE: DNA
<213> ORGANISM: Artificial Sequence
<220> FEATURE:
<223> OTHER INFORMATION: Chemically synthesized - vip3Aa20 probe

<400> SEQUENCE: 13

```
atgaacaaga caacaccaa gctgagcacc cgcgccctgc cgagcttcat cgactacttc     60
aacggcatct acggcttcgc caccggcatc aaggacatca tgaacatgat cttcaagacc    120
gacaccggcg cgacctgac cctggacgag atcctgaaga accagcagct gctgaacgac    180
atcagcggca gctggacgg cgtgaacggc gccctgaacg acctgatcgc ccagggcaac    240
ctgaacaccg agctgagcaa ggagatcctt aagatcgcca cgagcagaa ccaggtgctg    300
aacgacgtga caacaagct ggacgccatc aacaccatgc tgcgcgtgta cctgccgaag    360
atcaccagca tgctgagcga cgtgatgaag cagaactacg ccctgagcct gcagatcgag    420
tacctgagca gcagctgca ggagatcagc gacaagctgg acatcatcaa cgtgaacgtc    480
ctgatcaaca gcaccctgac cgagatcacc ccggcctacc agcgcatcaa gtacgtgaac    540
gagaagttcg aagagctgac cttcgccacc gagaccagca gcaaggtgaa gaaggacggc    600
agcccggccg acatcctgga cgagctgacc gagctgaccg agctggcgaa gagcgtgacc    660
aagaacgacg tggacggctt cgagttctac ctgaacacct ccacgacgt gatggtgggc    720
aacaacctgt tcggccgcag cgccctgaag accgccagcg agctgatcac caaggagaac    780
gtgaagacca gcggcagcga ggtgggcaac gtgtacaact tcctgatcgt gctgaccgcc    840
ctgcaggccc aggccttcct gaccctgacc acctgtcgca gctgctgggg cctgccgac    900
atcgactaca ccagcatcat gaacgagcac ttgaacaagg agaaggagga gttccgcgtg    960
aacatcctgc cgaccctgag caacaccttc agcaacccga actacgccaa ggtgaagggc   1020
agcgacgagg acgccaagat gatcgtggag gctaagccgg ccacgcgtt gatcggcttc   1080
gagatcagca acgacagcat caccgtgctg aaggtgtacg aggccaagct gaagcagaac   1140
taccaggtgg acaaggacag cttgagcgag gtgatctacg gcgacatgga caagctgctg   1200
tgtccggacc agagcgagca aatctactac accaacaaca tcgtgttccc gaacgagtac   1260
```

| | |
|---|---|
| gtgatcacca agatcgactt caccaagaag atgaagaccc tgcgctacga ggtgaccgcc | 1320 |
| aacttctacg acagcagcac cggcgagatc gacctgaaca agaagaaggt ggagagcagc | 1380 |
| gaggccgagt accgcaccct gagcgcgaac gacgacggcg tctacatgcc actgggcgtg | 1440 |
| atcagcgaga ccttcctgac cccgatcaac ggctttggcc tgcaggccga cgagaacagc | 1500 |
| cgcctgatca ccctgacctg taagagctac ctgcgcgagc tgctgctagc caccgacctg | 1560 |
| agcaacaagg agaccaagct gatcgtgcca ccgagcggct tcatcagcaa catcgtggag | 1620 |
| aacggcagca tcgaggagga caacctggag ccgtggaagg ccaacaacaa gaacgcctac | 1680 |
| gtggaccaca ccggcggcgt gaacggcacc aaggccctgt acgtgcacaa ggacggcggc | 1740 |
| atcagccagt tcatcggcga caagctgaag ccgaagaccg agtacgtgat ccagtacacc | 1800 |
| gtgaagggca agccatcgat tcacctgaag gacgagaaca ccggctacat ccactacgag | 1860 |
| gacaccaaca acaacctgga ggactaccag accatcaaca agcgcttcac caccggcacc | 1920 |
| gacctgaagg gcgtgtacct gatcctgaag agccagaacg cgacgaggc ctggggcgac | 1980 |
| aacttcatca tcctggagat cagcccgagc gagaagctgc tgagcccgga gctgatcaac | 2040 |
| accaacaact ggaccagcac cggcagcacc aacatcagcg gcaacaccct gaccctgtac | 2100 |
| cagggcggcc gcggcatcct gaagcagaac ctgcagctgg acagcttcag cacctaccgc | 2160 |
| gtgtacttca gcgtgagcgg cgacgccaac gtgcgcatcc gcaactcccg cgaggtgctg | 2220 |
| ttcgagaaga ggtacatgag cggcgccaag gacgtgagcg agatgttcac caccaagttc | 2280 |
| gagaaggaca acttctacat cgagctgagc cagggcaaca acctgtacgg cggcccgatc | 2340 |
| gtgcacttct acgacgtgag catcaagtag | 2370 |

<210> SEQ ID NO 14
<211> LENGTH: 1176
<212> TYPE: DNA
<213> ORGANISM: Artificial Sequence
<220> FEATURE:
<223> OTHER INFORMATION: Chemically synthesized - pmi probe

<400> SEQUENCE: 14

| | |
|---|---|
| atgcaaaaac tcattaactc agtgcaaaac tatgcctggg gcagcaaaac ggcgttgact | 60 |
| gaactttatg gtatggaaaa tccgtccagc cagccgatgg ccgagctgtg gatgggcgca | 120 |
| catccgaaaa gcagttcacg agtgcagaat gccgccggag atatcgtttc actgcgtgat | 180 |
| gtgattgaga gtgataaatc gactctgctc ggagaggccg ttgccaaacg ctttggcgaa | 240 |
| ctgcctttcc tgttcaaagt attatgcgca gcacagccac tctccattca ggttcatcca | 300 |
| aacaaacaca attctgaaat cggttttgcc aaagaaaatg ccgcaggtat cccgatggat | 360 |
| gccgccgagc gtaactataa agatcctaac cacaagccgg agctggtttt tgcgctgacg | 420 |
| cctttccttg cgatgaacgc gtttcgtgaa ttttccgaga ttgtctccct actccagccg | 480 |
| gtcgcaggtg cacatccggc gattgctcac tttttacaac agcctgatgc cgaacgttta | 540 |
| agcgaactgt tcgccagcct gttgaatatg cagggtgaag aaaaatcccg cgcgctggcg | 600 |
| attttaaaat cggccctcga tagccagcag ggtgaaccgt ggcaaacgat tcgtttaatt | 660 |
| tctgaatttt acccggaaga cagcggtctg ttctccccgc tattgctgaa tgtggtgaaa | 720 |
| ttgaaccctg gcgaagcgat gttcctgttc gctgaaacac cgcacgctta cctgcaaggc | 780 |
| gtggcgctgg aagtgatggc aaactccgat aacgtgctgc gtgcgggtct gacgcctaaa | 840 |
| tacattgata ttccggaact ggttgccaat gtgaaattcg aagccaaacc ggctaaccag | 900 |
| ttgttgaccc agccggtgaa acaaggtgca gaactggact ccccgattcc agtggatgat | 960 |

```
tttgccttct cgctgcatga ccttagtgat aaagaaacca ccattagcca gcagagtgcc   1020 gccatttttgt tctgcgtcga aggcgatgca acgttgtgga aaggttctca gcagttacag   1080
cttaaaccgg gtgaatcagc gtttattgcc gccaacgaat caccggtgac tgtcaaaggc   1140
cacggccgtt tagcgcgtgt ttacaacaag ctgtaa                              1176
```

```
<210> SEQ ID NO 15
<211> LENGTH: 20
<212> TYPE: DNA
<213> ORGANISM: Artificial Sequence
<220> FEATURE:
<223> OTHER INFORMATION: Chemically synthesized - MOV3Aa-01-5' primer

<400> SEQUENCE: 15
atgaacaaga acaacaccaa                                                 20

<210> SEQ ID NO 16
<211> LENGTH: 22
<212> TYPE: DNA
<213> ORGANISM: Artificial Sequence
<220> FEATURE:
<223> OTHER INFORMATION: Chemically synthesized - MOV3Aa-01-3' primer

<400> SEQUENCE: 16
ctacttgatg ctcacgtcgt ag                                              22

<210> SEQ ID NO 17
<211> LENGTH: 18
<212> TYPE: DNA
<213> ORGANISM: Artificial Sequence
<220> FEATURE:
<223> OTHER INFORMATION: Chemically synthesized

<400> SEQUENCE: 17
acgagcagaa ccaggtgc                                                   18

<210> SEQ ID NO 18
<211> LENGTH: 18
<212> TYPE: DNA
<213> ORGANISM: Artificial Sequence
<220> FEATURE:
<223> OTHER INFORMATION: Chemically synthesized

<400> SEQUENCE: 18
ggtgaagaag gacggcag                                                   18

<210> SEQ ID NO 19
<211> LENGTH: 20
<212> TYPE: DNA
<213> ORGANISM: Artificial Sequence
<220> FEATURE:
<223> OTHER INFORMATION: Chemically synthesized

<400> SEQUENCE: 19
acctgtcgca agctgctggg                                                 20

<210> SEQ ID NO 20
<211> LENGTH: 18
<212> TYPE: DNA
<213> ORGANISM: Artificial Sequence
<220> FEATURE:
<223> OTHER INFORMATION: Chemically synthesized

<400> SEQUENCE: 20
```

-continued

```
tggacaagct gctgtgtc                                              18
```

<210> SEQ ID NO 21
<211> LENGTH: 19
<212> TYPE: DNA
<213> ORGANISM: Artificial Sequence
<220> FEATURE:
<223> OTHER INFORMATION: Chemically synthesized

<400> SEQUENCE: 21

```
tgcaggccga cgagaacag                                             19
```

<210> SEQ ID NO 22
<211> LENGTH: 19
<212> TYPE: DNA
<213> ORGANISM: Artificial Sequence
<220> FEATURE:
<223> OTHER INFORMATION: Chemically synthesized

<400> SEQUENCE: 22

```
tgatccagta caccgtgaa                                             19
```

<210> SEQ ID NO 23
<211> LENGTH: 18
<212> TYPE: DNA
<213> ORGANISM: Artificial Sequence
<220> FEATURE:
<223> OTHER INFORMATION: Chemically synthesized

<400> SEQUENCE: 23

```
accctgaccc tgtaccag                                              18
```

<210> SEQ ID NO 24
<211> LENGTH: 18
<212> TYPE: DNA
<213> ORGANISM: Artificial Sequence
<220> FEATURE:
<223> OTHER INFORMATION: Chemically synthesized

<400> SEQUENCE: 24

```
gtgttgccgc tgatgttg                                              18
```

<210> SEQ ID NO 25
<211> LENGTH: 18
<212> TYPE: DNA
<213> ORGANISM: Artificial Sequence
<220> FEATURE:
<223> OTHER INFORMATION: Chemically synthesized

<400> SEQUENCE: 25

```
cgtactcggt cttcggct                                              18
```

<210> SEQ ID NO 26
<211> LENGTH: 18
<212> TYPE: DNA
<213> ORGANISM: Artificial Sequence
<220> FEATURE:
<223> OTHER INFORMATION: Chemically synthesized

<400> SEQUENCE: 26

```
ctgcaggcca aagccgtt                                              18
```

<210> SEQ ID NO 27
<211> LENGTH: 18
<212> TYPE: DNA
<213> ORGANISM: Artificial Sequence -continued
<220> FEATURE:
<223> OTHER INFORMATION: Chemically synthesized

<400> SEQUENCE: 27
tcgccgtaga tcacctcg                                                 18

<210> SEQ ID NO 28
<211> LENGTH: 18
<212> TYPE: DNA
<213> ORGANISM: Artificial Sequence
<220> FEATURE:
<223> OTHER INFORMATION: Chemcially synthesized

<400> SEQUENCE: 28
gcttgcgaca ggtggtca                                                 18

<210> SEQ ID NO 29
<211> LENGTH: 19
<212> TYPE: DNA
<213> ORGANISM: Artificial Sequence
<220> FEATURE:
<223> OTHER INFORMATION: Chemically synthesized

<400> SEQUENCE: 29
ttgctgctgg tctcggtgg                                                19

<210> SEQ ID NO 30
<211> LENGTH: 19
<212> TYPE: DNA
<213> ORGANISM: Artificial Sequence
<220> FEATURE:
<223> OTHER INFORMATION: Chemically synthesized

<400> SEQUENCE: 30
cgttggcgat cttaaggat                                                19

<210> SEQ ID NO 31
<211> LENGTH: 17
<212> TYPE: DNA
<213> ORGANISM: Artificial Sequence
<220> FEATURE:
<223> OTHER INFORMATION: Chemically synthesized

<400> SEQUENCE: 31
gcaagccatc gattcac                                                  17

<210> SEQ ID NO 32
<211> LENGTH: 17
<212> TYPE: DNA
<213> ORGANISM: Artificial Sequence
<220> FEATURE:
<223> OTHER INFORMATION: Chemically synthesized

<400> SEQUENCE: 32
gcaacaccct gaccctg                                                  17

<210> SEQ ID NO 33
<211> LENGTH: 20
<212> TYPE: DNA
<213> ORGANISM: Artificial Sequence
<220> FEATURE:
<223> OTHER INFORMATION: Chemically synthesized

<400> SEQUENCE: 33
tctacgacgt gagcatcaag                                               20

<210> SEQ ID NO 34
<211> LENGTH: 19
<212> TYPE: DNA
<213> ORGANISM: Artificial Sequence
<220> FEATURE:
<223> OTHER INFORMATION: Chemically synthesized

<400> SEQUENCE: 34
gtagaagtgc acgatcggg					19

<210> SEQ ID NO 35
<211> LENGTH: 17
<212> TYPE: DNA
<213> ORGANISM: Artificial Sequence
<220> FEATURE:
<223> OTHER INFORMATION: Chemcially synthesized

<400> SEQUENCE: 35
cggtgctggt ccagttg					17

<210> SEQ ID NO 36
<211> LENGTH: 21
<212> TYPE: DNA
<213> ORGANISM: Artificial Sequence
<220> FEATURE:
<223> OTHER INFORMATION: Chemcially synthesized - 162INSERT-F2 primer

<400> SEQUENCE: 36
acaccaatga tgcaaatagg c					21

<210> SEQ ID NO 37
<211> LENGTH: 25
<212> TYPE: DNA
<213> ORGANISM: Artificial Sequence
<220> FEATURE:
<223> OTHER INFORMATION: Chemically synthesized - VIP_R4 primer

<400> SEQUENCE: 37
gaaggtgttc aggtagaact cgaag				25

<210> SEQ ID NO 38
<211> LENGTH: 2946
<212> TYPE: DNA
<213> ORGANISM: Artificial Sequence
<220> FEATURE:
<223> OTHER INFORMATION: Chemcially synthesized - vip3Aa20 5' amplicon

<400> SEQUENCE: 38
acaccaatga tgcaaatagg ctgggaatag tctgtctaat agtttgagtg aatcatgtca		60 ctgatagttt aaactgaagg cgggaaacga caatctgatc atgagcggag aattaaggga		120 gtcacgttat gacccccgcc gatgacgcgg gacaagccgt tttacgtttg gaactgacag		180 aaccgcaacg ttgaaggagc cactcagcaa gctggtacaa gcttgcatgc ctgcagtgca		240 gcgtgacccg gtcgtgcccc tctctagaga taatgagcat tgcatgtcta agttataaaa		300 aattaccaca tatttttttt gtcacacttg tttgaagtgc agtttatcta tctttataca		360 tatatttaaa ctttactcta cgaataatat aatctatagt actacaataa tatcagtgtt		420 ttagagaatc atataaatga acagttagac atggtctaaa ggacaattga gtattttgac		480 aacaggactc tacagtttta tcttttagt gtgcatgtgt tctccttttt ttttgcaaat		540 agcttcacct atataatact tcatccattt tattagtaca tccatttagg gtttagggtt		600 aatggttttt atagactaat ttttttagta catctatttt attctatttt agcctctaaa		660

```
ttaagaaaac taaaactcta ttttagtttt tttatttaat aatttagata taaaatagaa    720
taaaataaag tgactaaaaa ttaaacaaat accctttaag aaattaaaaa aactaaggaa    780
acatttttct tgtttcgagt agataatgcc agcctgttaa acgccgtcga cgagtctaac    840
ggacaccaac cagcgaacca gcagcgtcgc gtcgggccaa gcgaagcaga cggcacggca    900
tctctgtcgc tgcctctgga cccctctcga gagttccgct ccaccgttgg acttgctccg    960
ctgtcggcat ccagaaattg cgtggcgagc ggcagacgt gagccggcac ggcaggcggc     1020
ctcctcctcc tctcacggca ccggcagcta cgggggattc ctttcccacc gctccttcgc   1080
tttcccttcc tcgcccgccg taataaatag acacccctc cacaccctct ttccccaacc    1140
tcgtgttgtt cggagcgcac acacacacaa ccagatctcc cccaaatcca cccgtcggca   1200
cctccgcttc aaggtacgcc gctcgtcctc ccccccccc cctctctacc ttctctagat    1260
cggcgttccg gtccatggtt agggcccggt agttctactt ctgttcatgt ttgtgttaga   1320
tccgtgtttg tgttagatcc gtgctgctag cgttcgtaca cggatgcgac ctgtacgtca   1380
gacacgttct gattgctaac ttgccagtgt ttctctttgg ggaatcctgg gatggctcta   1440
gccgttccgc agacgggatc gatttcatga ttttttttgt ttcgttgcat agggtttggt   1500
ttgccctttt cctttatttc aatatatgcc gtgcacttgt ttgtcgggtc atcttttcat   1560 gcttttttt gtcttggttg tgatgatgtg gtctggttgg gcggtcgttc tagatcggag    1620
tagaattctg tttcaaacta cctggtggat ttattaattt tggatctgta tgtgtgtgcc   1680
atacatattc atagttacga attgaagatg atggatggaa atatcgatct aggataggta   1740
tacatgttga tgcgggtttt actgatgcat atacagagat gctttttgtt cgcttggttg   1800
tgatgatgtg gtgtggttgg gcggtcgttc attcgttcta gatcggagta gaatactgtt   1860
tcaaactacc tggtgtattt attaattttg gaactgtatg tgtgtgtcat acatcttcat   1920
agttacgagt ttaagatgga tggaaatatc gatctaggat aggtatacat gttgatgtgg   1980
gttttactga tgcatataca tgatggcata tgcagcatct attcatatgc tctaaccttg   2040
agtacctatc tattataata aacaagtatg ttttataatt attttgatct tgatatactt   2100
ggatgatggc atatgcagca gctatatgtg gattttttta gccctgcctt catacgctat   2160
ttatttgctt ggtactgttt cttttgtcga tgctcaccct gttgtttggt gttacttctg   2220
caggtcgact ctagaggatc caccatgaac aagaacaaca ccaagctgag cacccgcgcc   2280
ctgccgagct tcatcgacta cttcaacggc atctacggct tcgccaccgg catcaaggac   2340
atcatgaaca tgatcttcaa gaccgacacc ggcggcgacc tgaccctgga cgagatcctg   2400
aagaaccagc agctgctgaa cgacatcagc ggcaagctgg acggcgtgaa cggcagcctg   2460
aacgacctga tcgcccaggg caacctgaac accgagctga gcaaggagat ccttaagatc   2520
gccaacgagc agaaccaggt gctgaacgac gtgaacaaca agctggacgc catcaacacc   2580
atgctgcgcg tgtacctgcc gaagatcacc agcatgctga gcgacgtgat taagcagaac   2640
tacgccctga gcctgcagat cgagtacctg agcaagcagc tgcaggagat cagcgacaag   2700
ctggacatca tcaacgtgaa cgtcctgatc aacagcaccc tgaccgagat caccccggcc   2760
taccagcgca tcaagtacgt gaacgagaag ttcgaagagc tgaccttcgc caccgagacc   2820
agcagcaagg tgaagaagga cggcagcccg gccgacatcc tggacgagct gaccgagctg   2880
accgagctgg cgaagagcgt gaccaagaac gacgtggacg gcttcgagtt ctacctgaac   2940
accttc                                                               2946
```

<210> SEQ ID NO 39
<211> LENGTH: 23
<212> TYPE: DNA
<213> ORGANISM: Artificial Sequence
<220> FEATURE:
<223> OTHER INFORMATION: Chemically synthesized - CJB179 Primer

<400> SEQUENCE: 39
atgcaaatag gctgggaata gtc                                          23

<210> SEQ ID NO 40
<211> LENGTH: 21
<212> TYPE: DNA
<213> ORGANISM: Artificial Sequence
<220> FEATURE:
<223> OTHER INFORMATION: Chemically synthesized - CTRB3116 Reverse
      Primer

<400> SEQUENCE: 40
gtaccagctt gctgagtggc t                                            21

<210> SEQ ID NO 41
<211> LENGTH: 209
<212> TYPE: DNA
<213> ORGANISM: Artificial Sequence
<220> FEATURE:
<223> OTHER INFORMATION: Chemically synthesized - CJB134/179 5' amplicon

<400> SEQUENCE: 41
atgcaaatag gctgggaata gtctgtctaa tagtttgagt gaatcatgtc actgatagtt    60
taaactgaag gcgggaaacg acaatctgat catgagcgga gaattaaggg agtcacgtta   120 tgaccccgc cgatgacgcg ggacaagccg ttttacgttt ggaactgaca gaaccgcaac   180
gttgaaggag ccactcagca agctggtac                                    209

<210> SEQ ID NO 42
<211> LENGTH: 20
<212> TYPE: DNA
<213> ORGANISM: Artificial Sequence
<220> FEATURE:
<223> OTHER INFORMATION: Chemcially synthesized - VIP-F3 primer

<400> SEQUENCE: 42
ggtgctgttc gagaagaggt                                              20

<210> SEQ ID NO 43
<211> LENGTH: 23
<212> TYPE: DNA
<213> ORGANISM: Artificial Sequence
<220> FEATURE:
<223> OTHER INFORMATION: Chemically synthesized - PMI_REV1 primer

<400> SEQUENCE: 43
cgatttatca ctctcaatca cat                                          23

<210> SEQ ID NO 44
<211> LENGTH: 2577
<212> TYPE: DNA
<213> ORGANISM: Artificial Sequence
<220> FEATURE:
<223> OTHER INFORMATION: Chemcially synthesized - vip3Aa20 3' amplicon

<400> SEQUENCE: 44
ggtgctgttc gagaagaggt acatgagcgg cgccaaggac gtgagcgaga tgttcaccac    60

```
caagttcgag aaggacaact tctacatcga gctgagccag ggcaacaacc tgtacggcgg    120
cccgatcgtg cacttctacg acgtgagcat caagtaggag ctctagatct gttctgcaca    180
aagtggagta gtcagtcatc gatcaggaac cagacaccag acttttattc atacagtgaa    240
gtgaagtgaa gtgcagtgca gtgagttgct ggttttttgta caacttagta tgtatttgta    300
tttgtaaaat acttctatca ataaaatttc taattcctaa aaccaaaatc caggggtacc    360
agcttgcatg cctgcagtgc agcgtgaccc ggtcgtgccc ctctctagag ataatgagca    420
ttgcatgtct aagttataaa aaattaccac atatttttt tgtcacactt gtttgaagtg    480
cagtttatct atctttatac atatatttaa actttactct acgaataata taatctatag    540
tactacaata atatcagtgt tttagagaat catataaatg aacagttaga catggtctaa    600
aggacaattg agtattttga caacaggact ctacagtttt atcttttag tgtgcatgtg    660 ttctcctttt tttttgcaaa tagcttcacc tatataatac ttcatccatt ttattagtac    720
atccatttag ggtttagggt taatggtttt tatagactaa ttttttagt acatctattt    780 tattctattt tagcctctaa attaagaaaa ctaaaactct attttagttt ttttatttaa    840
taatttagat ataaaataga ataaaataaa gtgactaaaa attaaacaaa tacccttttaa   900 gaaattaaaa aaactaagga aacattttc ttgtttcgag tagataatgc cagcctgtta    960
aacgccgtcg acgagtctaa cggacaccaa ccagcgaacc agcagcgtcg cgtcgggcca   1020
agcgaagcag acggcacggc atctctgtcg ctgcctctgg accctctcg agagttccgc    1080 tccaccgttg gacttgctcc gctgtcggca tccagaaatt gcgtggcgga gcggcagacg   1140
tgagccggca cggcaggcgg cctcctcctc ctctcacggc accggcagct acgggggatt   1200
cctttcccac cgctccttcg ctttcccttc ctcgcccgcc gtaataaata gacaccccct   1260 ccacacccctc tttccccaac ctcgtgttgt tcggagcgca cacacacaca accagatctc   1320
ccccaaatcc acccgtcggc acctccgctt caaggtacgc cgctcgtcct cccccccccc   1380
ccctctctac cttctctaga tcggcgttcc ggtccatggt tagggcccgg tagttctact   1440
tctgttcatg tttgtgttag atccgtgttt gtgttagatc cgtgctgcta gcgttcgtac   1500
acggatgcga cctgtacgtc agacacgttc tgattgctaa cttgccagtg tttctctttg   1560
gggaatcctg ggatggctct agccgttccg cagacgggat cgatttcatg attttttttg   1620
tttcgttgca tagggtttgg tttgcccttt tcctttattt caatatatgc cgtgcacttg   1680
tttgtcgggt catcttttca tgctttttttt tgtcttggtt gtgatgatgt ggtctggttg   1740
ggcggtcgtt ctagatcgga gtagaattct gtttcaaact acctggtgga tttattaatt   1800
ttggatctgt atgtgtgtgc catacatatt catagttacg aattgaagat gatggatgga   1860
aatatcgatc taggataggt atacatgttg atgcgggttt tactgatgca tatacagaga   1920 tgcttttttgt tcgcttggtt gtgatgatgt ggtgtggttg ggcggtcgtt cattcgttct   1980
agatcggagt agaatactgt tcaaactac ctggtgtatt tattaattttt ggaactgtat   2040 gtgtgtgtca tacatcttca tagttacgag tttaagatgg atggaaatat cgatctagga   2100
taggtataca tgttgatgtg ggttttactg atgcatatac atgatggcat atgcagcatc   2160
tattcatatg ctctaacctt gagtacctat ctattataat aaacaagtat gttttataat   2220
tattttgatc ttgatatact tggatgatgg catatgcagc agctatatgt ggattttttt   2280
agccctgcct tcatacgcta tttatttgct tggtactgtt tcttttgtcg atgctcaccc   2340
tgttgtttgg tgttacttct gcagggatcc ccgatcatga aaaaactcat taactcagtg   2400
caaaactatg cctggggcag caaaacggcg ttgactgaac tttatggtat ggaaaatccg   2460
```

```
tccagccagc cgatggccga gctgtggatg ggcgcacatc cgaaaagcag ttcacgagtg    2520
cagaatgccg ccggagatat cgtttcactg cgtgatgtga ttgagagtga taaatcg      2577

<210> SEQ ID NO 45
<211> LENGTH: 20
<212> TYPE: DNA
<213> ORGANISM: Artificial Sequence
<220> FEATURE:
<223> OTHER INFORMATION: 5' junction sequence between corn genome and
      insert DNA

<400> SEQUENCE: 45
tgaatcatgt cactgatagt                                                 20

<210> SEQ ID NO 46
<211> LENGTH: 1088
<212> TYPE: DNA
<213> ORGANISM: Artificial Sequence
<220> FEATURE:
<223> OTHER INFORMATION: 5' flanking sequence
<220> FEATURE:
<221> NAME/KEY: misc_feature
<222> LOCATION: (1)..(236)
<223> OTHER INFORMATION: 5' flanking sequence

<400> SEQUENCE: 46
tcctgtgttg ttggaacaga cttctgtctc ttctggtgat cataaatatt taaatgaacc     60
agttgtgttg gaaaatgttg ttttcttttg tctctagact ggaaagcgga gttctcgtca    120
acacggttct ttcaactagg gatgaaagtg gtaatccgaa ttgttagtac aaatttaata    180
ttttaaaata gatatgtata aaattttatg ttgatctttt ttatgttatc aagcacatta    240
gtataaatta gtaaaatat gaataaaata ttacataaaa tgttttatgt attatttggt    300
ccctacaaca taaatagttg aaaaaattac taaatttgtt ttcgaatcta tatcgaagtt    360
tatatctatt atttaagaaa aatataggat gaaaaggttt atcttttatg aatctttaca    420
agctggatct tataaacaag aaaataaatt tatattgtag attttatatc ctatttattc    480
gcaatcaaag aaaagcgact aaaaaactga ttaccgagta aatactgttt ccaaccgttt    540
tcgtccctac tatcaacgcc ttctcccaac cgcagtcgat ctgtccgtct gtatcaggcg    600
cagcggcacc cctgctgttc gactatctag accatagaat attttaggta tacaataatt    660
ttagttccac gctagaacat tttagttaga ataataacaa gatttgctat tgatgtagga    720
ctcgcccgtc actgtctaaa aaagcattct gtcggtctta ttcttaggc atcagcgggt     780 gtactatctc attttttccta tcatattcct cagtactctg ttaagtataa atggtctatt    840
ttacatgatg aactaataaa actaattaag gatcctaact ttttgtgaag gtaatttgga    900
tcattatgca ttaccatcct acgtatacct gctgcagcag catctgcgta agcacagcct    960
agatatatgc ttctgtgtgg actgaaagga gactttgttt atcaattagt atactcccaa   1020
aaaactgatg acaccaatga tgcaaatagg ctgggaatag tctgtctaat agtttgagtg   1080
aatcatgt                                                            1088

<210> SEQ ID NO 47
<211> LENGTH: 20
<212> TYPE: DNA
<213> ORGANISM: Artificial Sequence
<220> FEATURE:
<223> OTHER INFORMATION: 3' junction sequence between insert DNA and
      corn genome
```

```
<400> SEQUENCE: 47
aaacgtccgc catggtctga                                                     20

<210> SEQ ID NO 48
<211> LENGTH: 1189
<212> TYPE: DNA
<213> ORGANISM: Artificial Sequence
<220> FEATURE:
<223> OTHER INFORMATION: 3' flanking sequence

<400> SEQUENCE: 48
catggtctga aggcaacaga taaggcatac tgggccttgt ggtagttgtt ttactgggcc         60
tttttgtatg atctataaaa ttcactggga tcaacccgga gaggaatggc agcagatgca        120
gtccccaggg tcctccgtcg ccgcctgagc acccggcacc cgcgctgaac cggagaggga        180
cgcgcggacg ccgtgcagct ggtgcggagg gggctgtggc agatgaggat gagacgcgta        240
cgtggctggg aaggccagca ggccaccggg tcttcgtcca gcccggcgcg agtggacagg        300
actagagatg gcaacggtta caaacccgct gggttttacc gtcccaaacc cgtacccgtg        360
aaaaatatct atgcccatta aaaaacccgt acccatgacg ggtttgagat tttgcccaaa        420
cccgtaccca tcgggttaac gggtacccat gggttacccg cgggtttcat ctccaatata        480
cctgttcttc tcataatcaa taagtatcgt aatgattaat gatatcatga tccaaaatct        540
atgtaatgaa caacgagttc atgatttggt ataaaaatta ttagtagaga gaatgaaata        600
caaataataa gttgtataat taagtgacct tgcactaagt tatccatcca tcacatatat        660
aacgctagta aaaactataa tatcaagcaa gcaacactct caccgactac tgatacattc        720
accaattgat aaaaaatatg aagtaaataa ggaataacaa gtttgttgtt cgtttataaa        780
ataaaatgac aatatgcact aggtttggtc gggtttaaaa acccacggg ttcacggggtt       840 tgggtactat aggaacaaac ccgtacccat aaacccattg ggtacagatt tatgcccgtt        900
aacaaaccca tgggtatgaa aattgaccca aacctatacc ctaatggggt aaaaacccat        960
cgggtttcgg atttcgggta cccattgcca tctctagaca ggacaacctc ggccggtcct      1020
gtatgtaggc caccagcatc ggccagttgg tacatccagc cggggtcagg tcacttttac      1080
tcgtctcaat cagacaatca ccgtccacca acgaacgcca acgttgtcac ttgtcaggtc      1140
ggttgagact tgtatttttt tttgtcctcc gtaaaaatcg gttcaccag                  1189

<210> SEQ ID NO 49
<211> LENGTH: 10579
<212> TYPE: DNA
<213> ORGANISM: Artificial Sequence
<220> FEATURE:
<223> OTHER INFORMATION: Vip3Aa20 Event MIR162 insert and flanking
      sequences
<220> FEATURE:
<221> NAME/KEY: misc_feature
<222> LOCATION: (1)..(1088)
<223> OTHER INFORMATION: 5' flanking sequence of event MIR162

<400> SEQUENCE: 49
tcctgtgttg ttggaacaga cttctgtctc ttctggtgat cataaatatt taaatgaacc         60
agttgtgttg gaaaatgttg tttctttttg tctctagact ggaaagcgga gttctcgtca        120
acacggttct ttcaactagg gatgaaagtg gtaatccgaa ttgttagtac aaatttaata        180
ttttaaaata gatatgtata aaattttatg ttgatctttt ttatgttatc aagcacatta        240
gtataaatta gtataaatat gaataaaata ttacataaaa tgttttatgt attatttggt        300
```

| | | |
|---|---|---|
| ccctacaaca taaatagttg aaaaaattac taaatttgtt ttcgaatcta tatcgaagtt | 360 |
| tatatctatt atttaagaaa aatataggat gaaaaggttt atcttttatg aatctttaca | 420 |
| agctggatct tataaacaag aaaataaatt tatattgtag attttatatc ctatttattc | 480 |
| gcaatcaaag aaaagcgact aaaaaactga ttaccgagta aatactgttt ccaaccgttt | 540 |
| tcgtccctac tatcaacgcc ttctcccaac cgcagtcgat ctgtccgtct gtatcaggcg | 600 |
| cagcggcacc cctgctgttc gactatctag accatagaat attttaggta tacaataatt | 660 |
| ttagttccac gctagaacat tttagttaga ataataacaa gatttgctat tgatgtagga | 720 |
| ctcgcccgtc actgtctaaa aaagcattct gtcggtctta ttctttaggc atcagcgggt | 780 |
| gtactatctc attttttccta tcatattcct cagtactctg ttaagtataa atggtctatt | 840 |
| ttacatgatg aactaataaa actaattaag gatcctaact ttttgtgaag gtaatttgga | 900 |
| tcattatgca ttaccatcct acgtatacct gctgcagcag catctgcgta agcacagcct | 960 |
| agatatatgc ttctgtgtgg actgaaagga gactttgttt atcaattagt atactcccaa | 1020 |
| aaaactgatg acaccaatga tgcaaatagg ctgggaatag tctgtctaat agtttgagtg | 1080 |
| aatcatgtca ctgatagttt aaactgaagg cgggaaacga caatctgatc atgagcggag | 1140 |
| aattaaggga gtcacgttat gacccccgcc gatgacgcgg gacaagccgt tttacgtttg | 1200 |
| gaactgacag aaccgcaacg ttgaaggagc cactcagcaa gctggtacaa gcttgcatgc | 1260 |
| ctgcagtgca gcgtgacccg gtcgtgcccc tctctagaga taatgagcat tgcatgtcta | 1320 |
| agttataaaa aattaccaca tattttttt gtcacacttg tttgaagtgc agtttatcta | 1380 |
| tctttataca tatatttaaa ctttactcta cgaataatat aatctatagt actacaataa | 1440 |
| tatcagtgtt ttagagaatc atataaatga acagttagac atggtctaaa ggacaattga | 1500 |
| gtattttgac aacaggactc tacagtttta tcttttttagt gtgcatgtgt tctccttttt | 1560 |
| ttttgcaaat agcttcacct atataatact tcatccattt tattagtaca tccatttagg | 1620 |
| gtttagggtt aatggttttt atagactaat ttttttagta catctatttt attctatttt | 1680 |
| agcctctaaa ttaagaaaac taaaactcta ttttagtttt tttatttaat aatttagata | 1740 |
| taaaatagaa taaaataaag tgactaaaaa ttaaacaaat acccttaag aaattaaaaa | 1800 |
| aactaaggaa acatttttct tgtttcgagt agataatgcc agcctgttaa acgccgtcga | 1860 |
| cgagtctaac ggacaccaac cagcgaacca gcagcgtcgc gtcgggccaa gcgaagcaga | 1920 |
| cggcacggca tctctgtcgc tgcctctgga cccctctcga gagttccgct ccaccgttgg | 1980 |
| acttgctccg ctgtcggcat ccagaaattg cgtggcggag cggcagacgt gagccggcac | 2040 |
| ggcaggcggc ctcctcctcc tctcacgca ccggcagcta cgggggattc ctttcccacc | 2100 |
| gctccttcgc tttcccttcc tcgcccgccg taataaatag acaccccctc cacaccctct | 2160 |
| ttccccaacc tcgtgttgtt cggagcgcac acacacacaa ccagatctcc cccaaatcca | 2220 |
| cccgtcggca cctccgcttc aaggtacgcc gctcgtcctc cccccccccc cctctctacc | 2280 |
| ttctctagat cggcgttccg gtccatggtt agggcccggt agttctactt ctgttcatgt | 2340 |
| ttgtgttaga tccgtgtttg tgttagatcc gtgctgctag cgttcgtaca cggatgcgac | 2400 |
| ctgtacgtca gacacgttct gattgctaac ttgccagtgt ttctctttgg ggaatcctgg | 2460 |
| gatggctcta gccgttccgc agacgggatc gatttcatga tttttttttgt ttcgttgcat | 2520 |
| agggtttggt ttgcccttt cctttatttc aatatatgcc gtgcacttgt ttgtcgggtc | 2580 |
| atcttttcat gctttttttt gtcttggttg tgatgatgtg gtctggttgg gcggtcgttc | 2640 |
| tagatcggag tagaattctg tttcaaacta cctggtggat ttattaattt tggatctgta | 2700 |

```
tgtgtgtgcc atacatattc atagttacga attgaagatg atggatggaa atatcgatct    2760
aggataggta tacatgttga tgcgggtttt actgatgcat atacagagat gcttttttgtt   2820 cgcttggttg tgatgatgtg gtgtggttgg gcggtcgttc attcgttcta gatcggagta    2880
gaatactgtt tcaaactacc tggtgtattt attaattttg aactgtatg tgtgtgtcat     2940 acatcttcat agttacgagt ttaagatgga tggaaatatc gatctaggat aggtatacat    3000
gttgatgtgg gttttactga tgcatataca tgatggcata tgcagcatct attcatatgc   3060
tctaaccttg agtacctatc tattataata aacaagtatg ttttataatt attttgatct    3120
tgatatactt ggatgatggc atatgcagca gctatatgtg gattttttta gccctgcctt    3180
catacgctat ttatttgctt ggtactgttt cttttgtcga tgctcaccct gttgtttggt    3240
gttacttctg caggtcgact ctagaggatc caccatgaac aagaacaaca ccaagctgag    3300
cacccgcgcc ctgccgagct tcatcgacta cttcaacggc atctacggct tcgccaccgg    3360
catcaaggac atcatgaaca tgatcttcaa gaccgacacc ggcggcgacc tgaccctgga    3420
cgagatcctg aagaaccagc agctgctgaa cgacatcagc ggcaagctgg acggcgtgaa    3480
cggcagcctg aacgacctga tcgcccaggg caacctgaac accgagctga gcaaggagat    3540
ccttaagatc gccaacgagc agaaccaggt gctgaacgac gtgaacaaca agctggacgc    3600
catcaacacc atgctgcgcg tgtacctgcc gaagatcacc agcatgctga gcgacgtgat    3660
gaagcagaac tacgccctga gcctgcagat cgagtacctg agcaagcagc tgcaggagat    3720
cagcgacaag ctggacatca tcaacgtgaa cgtcctgatc aacagcaccc tgaccgagat    3780 cacccccggcc taccagcgca tcaagtacgt gaacgagaag ttcgaagagc tgaccttcgc    3840
caccgagacc agcagcaagg tgaagaagga cggcagcccg gccgacatcc tggacgagct    3900
gaccgagctg accgagctgg cgaagagcgt gaccaagaac gacgtggacg gcttcgagtt    3960
ctacctgaac accttccacg acgtgatggt gggcaacaac ctgttcggcc gcagcgccct    4020
gaagaccgcc agcgagctga tcaccaagga gaacgtgaag accagcggca gcgaggtggg   4080
caacgtgtac aacttcctga tcgtgctgac cgccctgcag gcccaggcct tcctgacccct    4140 gaccacctgt cgcaagctgc tgggcctggc cgacatcgac tacaccagca tcatgaacga    4200
gcacttgaac aaggagaagg aggagttccg cgtgaacatc ctgccgaccc tgagcaacac    4260
cttcagcaac ccgaactacg ccaaggtgaa gggcagcgac gaggacgcca agatgatcgt    4320
ggaggctaag ccgggccacg cgttgatcgg cttcgagatc agcaacgaca gcatcaccgt    4380
gctgaaggta tacgaggcca agctgaagca gaactaccag gtggacaagg acagcttgag    4440
cgaggtgatc tacggcgaca tggacaagct gctgtgtccg gaccagagcg agcaaatcta    4500
ctacaccaac aacatcgtgt tcccgaacga gtacgtgatc accaagatcg acttcaccaa    4560
gaagatgaag accctgcgct acgaggtgac cgccaacttc tacgacagca gcaccggcga    4620
gatcgacctg aacaagaaga aggtggagag cagcgaggcc gagtaccgca ccctgagcgc    4680
gaacgacgac ggcgtctaca tgccactggg cgtgatcagc gagaccttcc tgaccccgat    4740
caacggcttt ggcctgcagg ccgacgagaa cagccgcctg atcaccctga cctgtaagag    4800
ctacctgcgc gagctgctgc tagccaccga cctgagcaac aaggagacca agctgatcgt    4860
gccaccgagc ggcttcatca gcaacatcgt ggagaacggc agcatcgagg aggacaacct    4920
ggagccgtgg aaggccaaca acaagaacgc ctacgtggac cacaccggcg gcgtgaacgg    4980
caccaaggcc ctgtacgtgc acaaggacgg cggcatcagc cagttcatcg gcgacaagct    5040
```

```
gaagccgaag accgagtacg tgatccagta caccgtgaag ggcaagccat cgattcacct    5100
gaaggacgag aacaccggct acatccacta cgaggacacc aacaacaacc tggaggacta    5160
ccagaccatc aacaagcgct tcaccaccgg caccgacctg aagggcgtgt acctgatcct    5220
gaagagccag aacggcgacg aggcctgggg cgacaacttc atcatcctgg agatcagccc    5280
gagcgagaag ctgctgagcc cggagctgat caacaccaac aactggacca gcaccggcag    5340
caccaacatc agcggcaaca ccctgaccct gtaccagggc ggccgcggca tcctgaagca    5400
gaacctgcag ctggacagct tcagcaccta ccgcgtgtac ttcagcgtga gcggcgacgc    5460
caacgtgcgc atccgcaact cccgcgaggt gctgttcgag aagaggtaca tgagcggcgc    5520
caaggacgtg agcgagatgt tcaccaccaa gttcgagaag gacaacttct acatcgagct    5580
gagccagggc aacaacctgt acggcggccc gatcgtgcac ttctacgacg tgagcatcaa    5640
gtaggagctc tagatctgtt ctgcacaaag tggagtagtc agtcatcgat caggaaccag    5700
acaccagact tttattcata cagtgaagtg aagtgaagtg cagtgcagtg agttgctggt    5760
ttttgtacaa cttagtatgt atttgtattt gtaaatact  tctatcaata aaatttctaa    5820
ttcctaaaac caaaatccag gggtaccagc ttgcatgcct gcagtgcagc gtgacccggt    5880
cgtgcccctc tctagagata tgagcattg  catgtctaag ttataaaaaa ttaccacata    5940
ttttttttgt cacacttgtt tgaagtgcag tttatctatc tttatacata tatttaaact    6000
ttactctacg aataatataa tctatagtac tacaataata tcagtgtttt agagaatcat    6060
ataaatgaac agttagacat ggtctaaagg acaattgagt attttgacaa caggactcta    6120
cagttttatc ttttttagtgt gcatgtgttc tccttttttt ttgcaaatag cttcacctat    6180
ataatacttc atccatttta ttagtacatc catttagggt ttaggttaa  tggttttat     6240 agactaattt ttttagtaca tctattttat tctattttag cctctaaatt aagaaaacta    6300
aaactctatt ttagtttttt tatttaataa tttagatata aaatagaata aaataaagtg    6360
actaaaaatt aaacaaatac cctttaagaa attaaaaaaa ctaaggaaac atttttcttg    6420
tttcgagtag ataatgccag cctgttaaac gccgtcgacg agtctaacgg acaccaacca    6480
gcgaaccagc agcgtcgcgt cgggccaagc gaagcagacg gcacggcatc tctgtcgctg    6540
cctctggacc cctctcgaga gttccgctcc accgttggac ttgctccgct gtcggcatcc    6600
agaaattgcg tggcggagcg gcagacgtga gccggcacgg caggcggcct cctcctcctc    6660
tcacggcacc ggcagctacg ggggattcct ttcccaccgc tccttcgctt tcccttcctc    6720
gcccgccgta ataaatagac accccctcca caccctcttt ccccaacctc gtgttgttcg    6780
gagcgcacac acacacaacc agatctcccc caaatccacc cgtcggcacc tccgcttcaa    6840
ggtacgccgc tcgtcctccc cccccccccc tctctacctt ctctagatcg gcgttccggt    6900
ccatggttag ggcccggtag ttctacttct gttcatgttt gtgttagatc cgtgtttgtg    6960
ttagatccgt gctgctagcg ttcgtacacg gatgcgacct gtacgtcaga cacgttctga    7020
ttgctaactt gccagtgttt ctctttgggg aatcctggga tggctctagc cgttccgcag    7080
acgggatcga tttcatgatt ttttttgttt cgttgcatag ggtttggttt gcccttttcc    7140
tttatttcaa tatatgccgt gcacttgttt gtcgggtcat cttttcatgc ttttttttgt    7200
cttggttgtg atgatgtggt ctggttgggc ggtcgttcta gatcggagta gaattctgtt    7260
tcaaactacc tggtggattt attaattttg gatctgtatg tgtgtgccat acatattcat    7320
agttacgaat tgaagatgat ggatggaaat atcgatctag gataggtata catgttgatg    7380
cgggttttac tgatgcatat acagagatgc ttttgttcg  cttggttgtg atgatgtggt    7440
```

```
gtggttgggc ggtcgttcat tcgttctaga tcggagtaga atactgtttc aaactacctg    7500
gtgtatttat taattttgga actgtatgtg tgtgtcatac atcttcatag ttacgagttt    7560
aagatggatg gaaatatcga tctaggatag gtatacatgt tgatgtgggt tttactgatg    7620
catatacatg atggcatatg cagcatctat tcatatgctc taaccttgag tacctatcta    7680
ttataataaa caagtatgtt ttataattat tttgatcttg atatacttgg atgatggcat    7740
atgcagcagc tatatgtgga ttttttagc cctgccttca tacgctattt atttgcttgg    7800
tactgtttct tttgtcgatg ctcaccctgt tgtttggtgt tacttctgca gggatccccg    7860
atcatgcaaa aactcattaa ctcagtgcaa aactatgcct ggggcagcaa aacggcgttg    7920
actgaacttt atggtatgga aaatccgtcc agccagccga tggccgagct gtggatgggc    7980
gcacatccga aaagcagttc acgagtgcag aatgccgccg gagatatcgt ttcactgcgt    8040
gatgtgattg agagtgataa atcgactctg ctcggagagg ccgttgccaa acgctttggc    8100
gaactgcctt tcctgttcaa agtattatgc gcagcacagc cactctccat tcaggttcat    8160
ccaaacaaac acaattctga atcggttttt gccaaagaaa atgccgcagg tatcccgatg    8220
gatgccgccg agcgtaacta taagatcct aaccacaagc cggagctggt ttttgcgctg    8280
acgcctttcc ttgcgatgaa cgcgtttcgt gaattttccg agattgtctc cctactccag    8340
ccggtcgcag gtgcacatcc ggcgattgct cacttttttac aacagcctga tgccgaacgt    8400
ttaagcgaac tgttcgccag cctgttgaat atgcagggtg aagaaaaatc ccgcgcgctg    8460
gcgattttaa aatcggccct cgatagccag caggtgaaac cgtggcaaac gattcgttta    8520
atttctgaat tttacccgga agacagcggt ctgttctccc cgctattgct gaatgtggtg    8580
aaattgaacc ctggcgaagc gatgttcctg ttcgctgaaa caccgcacgc ttacctgcaa    8640
ggcgtggcgc tggaagtgat ggcaaactcc gataacgtgc tgcgtgcggg tctgacgcct    8700
aaatacattg atattccgga actggttgcc aatgtgaaat cgaagccaa accggctaac    8760 cagttgttga cccagccggt gaaacaaggt gcagaactgg acttcccgat tccagtggat    8820
gattttgcct tctcgctgca tgaccttagt gataaagaaa ccaccattag ccagcagagt    8880
gccgccattt tgttctgcgt cgaaggcgat gcaacgttgt ggaaaggttc tcagcagtta    8940
cagcttaaac cgggtgaatc agcgtttatt gccgccaacg aatcaccggt gactgtcaaa    9000
ggccacggcc gtttagcgcg tgtttacaac aagctgtaag agcttactga aaaaattaac    9060
atctcttgct aagctgggag ctcgatccgt cgacctgcag atcgttcaaa catttggcaa    9120
taaagtttct taagattgaa tcctgttgcc ggtcttgcga tgattatcat ataatttctg    9180
ttgaattacg ttaagcatgt aataattaac atgtaatgca tgacgttatt tatgagatgg    9240
gtttttatga ttagagtccc gcaattatac atttaatacg cgatagaaaa caaaatatag    9300
cgcgcaaact aggataaatt atcgcgcgcg gtgtcatcta tgttactaga tccccgggtc    9360
tagacaattc agtacattaa aaacgtccgc catggtctga aggcaacaga taaggcatac    9420
tgggccttgt ggtagttgtt ttactgggcc tttttgtatg atctataaaa ttcactggga    9480
tcaacccgga gaggaatggc agcagatgca gtccccaggg tcctccgtcg ccgcctgagc    9540
acccggcacc cgcgctgaac cggagaggga cgcgcggacg ccgtgcagct ggtgcggagg    9600
gggctgtggc agatgaggat gagacgcgta cgtggctggg aaggccagca ggccaccggg    9660
tcttcgtcca gcccggcgcg agtggacagg actagagatg gcaacggtta caaacccgct    9720
gggttttacc gtcccaaacc cgtacccgtg aaaaatatct atgcccatta aaaaacccgt    9780
```

```
acccatgacg ggtttgagat tttgcccaaa cccgtaccca tcgggttaac gggtacccat    9840
gggttacccg cgggtttcat ctccaatata cctgttcttc tcataatcaa taagtatcgt    9900
aatgattaat gatatcatga tccaaaatct atgtaatgaa caacgagttc atgatttggt    9960
ataaaaatta ttagtagaga gaatgaaata caaataataa gttgtataat taagtgacct   10020
tgcactaagt tatccatcca tcacatatat aacgctagta aaactataa tatcaagcaa    10080 gcaacactct caccgactac tgatacattc accaattgat aaaaaatatg aagtaaataa   10140
ggaataacaa gtttgttgtt cgtttataaa ataaaatgac aatatgcact aggtttggtc   10200
gggtttaaaa aacccacggg ttcacgggtt tgggtactat aggaacaaac ccgtaccct    10260 aaacccattg ggtacagatt tatgcccgtt aacaaaccca tgggtatgaa aattgaccca   10320
aacctatacc ctaatggggt aaaaaccccat cgggtttcgg atttcgggta cccattgcca   10380
tctctagaca ggacaacctc ggccggtcct gtatgtaggc caccagcatc ggccagttgg   10440
tacatccagc cggggtcagg tcacttttac tcgtctcaat cagacaatca ccgtccacca   10500
acgaacgcca acgttgtcac ttgtcaggtc ggttgagact tgtattttt tttgtcctcc    10560 gtaaaaatcg gttcaccag                                                10579

<210> SEQ ID NO 50
<211> LENGTH: 23
<212> TYPE: DNA
<213> ORGANISM: Artificial Sequence
<220> FEATURE:
<223> OTHER INFORMATION: Chemically synthesized - FE1002 primer

<400> SEQUENCE: 50
cgtgactccc ttaattctcc gct                                              23

<210> SEQ ID NO 51
<211> LENGTH: 24
<212> TYPE: DNA
<213> ORGANISM: Artificial Sequence
<220> FEATURE:
<223> OTHER INFORMATION: Chemically synthesized - FE1003 primer

<400> SEQUENCE: 51
gatcagattg tcgtttcccg cctt                                             24

<210> SEQ ID NO 52
<211> LENGTH: 24
<212> TYPE: DNA
<213> ORGANISM: Artificial Sequence
<220> FEATURE:
<223> OTHER INFORMATION: Chemically synthesized - FE1004 primer

<400> SEQUENCE: 52
gattgtcgtt tcccgccttc agtt                                             24

<210> SEQ ID NO 53
<211> LENGTH: 27
<212> TYPE: DNA
<213> ORGANISM: Artificial Sequence
<220> FEATURE:
<223> OTHER INFORMATION: Chemically synthesized - 162_DW_Conf3 primer

<400> SEQUENCE: 53
cctgtgttgt tggaacagac ttctgtc                                          27

<210> SEQ ID NO 54
<211> LENGTH: 26
```

```
<212> TYPE: DNA
<213> ORGANISM: Artificial Sequence
<220> FEATURE:
<223> OTHER INFORMATION: Chemically synthesized - FE0900 primer

<400> SEQUENCE: 54
ggctccttca acgttgcggt tctgtc                                          26

<210> SEQ ID NO 55
<211> LENGTH: 1230
<212> TYPE: DNA
<213> ORGANISM: Artificial Sequence
<220> FEATURE:
<223> OTHER INFORMATION: Chemically synthesized - 5' PCR amplicon

<400> SEQUENCE: 55
cctgtgttgt tggaacagac ttctgtctct tctggtgatc ataaatattt aaatgaacca      60
gttgtgttgg aaaatgttgt tttcttttgt ctctagactg gaaagcggag ttctcgtcaa     120
cacggttctt tcaactaggg atgaaagtgg taatccgaat tgttagtaca aatttaatat     180
tttaaaatag atatgtataa aattttatgt tgatcttttt tatgttatca agcacattag     240
tataaattag tataaatatg aataaaatat tacataaaat gttttatgta ttatttggtc     300
cctacaacat aaatagttga aaaaattact aaatttgttt tcgaatctat atcgaagttt     360
atatctatta tttaagaaaa atataggatg aaaaggttta tcttttatga atctttacaa     420
gctggatctt ataaacaaga aaataaattt atattgtaga ttttatatcc tatttattcg     480
caatcaaaga aaagcgacta aaaaactgat taccgagtaa atactgtttc caaccgtttt     540
cgtccctact atcaacgcct tctcccaacc gcagtcgatc tgtccgtctg tatcaggcgc     600
agcggcaccc ctgctgttcg actatctaga ccatagaata ttttaggtat acaataattt     660
tagttccacg ctagaacatt ttagttagaa taataacaag atttgctatt gatgtaggac     720
tcgcccgtca ctgtctaaaa aagcattctg tcggtcttat tctttaggca tcagcgggtg     780
tactatctca ttttttcctat catattcctc agtactctgt taagtataaa tggtctattt     840
tacatgatga actaataaaa ctaattaagg atcctaactt tttgtgaagg taatttggat     900
cattatgcat taccatccta cgtatacctg ctgcagcagc atctgcgtaa gcacagccta     960
gatatatgct tctgtgtgga ctgaaaggag actttgttta tcaattagta tactcccaaa    1020
aaactgatga caccaatgat gcaaataggc tgggaatagt ctgtctaata gtttgagtga    1080
atcatgtcac tgatagttta aactgaaggc gggaaacgac aatctgatca tgagcggaga    1140
attaagggag tcacgttatg accccgccg atgacgcggg acaagccgtt ttacgtttgg     1200
aactgacaga accgcaacgt tgaaggagcc                                     1230

<210> SEQ ID NO 56
<211> LENGTH: 28
<212> TYPE: DNA
<213> ORGANISM: Artificial Sequence
<220> FEATURE:
<223> OTHER INFORMATION: Chemically synthesized - 162_GW_3_F1 primer

<400> SEQUENCE: 56
tctcttgcta agctgggagc tcgatccg                                        28

<210> SEQ ID NO 57
<211> LENGTH: 28
<212> TYPE: DNA
<213> ORGANISM: Artificial Sequence
<220> FEATURE:
```

<223> OTHER INFORMATION: Chemically synthesized - 162_GW_3_F2 primer

<400> SEQUENCE: 57
aagattgaat cctgttgccg gtcttgcg                                              28

<210> SEQ ID NO 58
<211> LENGTH: 24
<212> TYPE: DNA
<213> ORGANISM: Artificial Sequence
<220> FEATURE:
<223> OTHER INFORMATION: Chemically synthesized162_3'GW_R1 primer

<400> SEQUENCE: 58
ctggtgaacc gatttttacg gagg                                                  24

<210> SEQ ID NO 59
<211> LENGTH: 1518
<212> TYPE: DNA
<213> ORGANISM: Artificial Sequence
<220> FEATURE:
<223> OTHER INFORMATION: Chemically synthesized - 3' PCR amplicon

<400> SEQUENCE: 59
tctcttgcta agctgggagc tcgatccgtc gacctgcaga tcgttcaaac atttggcaat        60
aaagtttctt aagattgaat cctgttgccg gtcttgcgat gattatcata taatttctgt       120
tgaattacgt taagcatgta ataattaaca tgtaatgcat gacgttattt atgagatggg       180 ttttttatgat tagagtcccg caattataca tttaatacgc gatagaaaac aaaatatagc      240
gcgcaaacta ggataaatta tcgcgcgcgg tgtcatctat gttactagat ccccgggtct       300
agacaattca gtacattaaa aacgtccgcc atggtctgaa ggcaacagat aaggcatact       360
gggccttgtg gtagttgttt tactgggcct ttttgtatga tctataaaat tcactgggat       420
caacccggag aggaatggca gcagatgcag tccccagggt cctccgtcgc cgcctgagca       480
cccggcaccc gcgctgaacc ggagagggac gcgcggacgc cgtgcagctg gtgcggaggg       540
ggctgtggca gatgaggatg agacgcgtac gtggctggga aggccagcag gccaccgggt       600
cttcgtccag cccggcgcga gtggacagga ctagagatgg caacggttac aaacccgctg       660
ggttttaccg tcccaaaccc gtacccgtga aaaatatcta tgcccattaa aaaacccgta       720
cccatgacgg gtttgagatt tgcccaaac ccgtacccat cgggttaacg ggtacccatg        780
ggttacccgc gggtttcatc tccaatatac ctgttcttct cataatcaat aagtatcgta       840
atgattaatg atatcatgat ccaaaatcta tgtaatgaac aacgagttca tgatttggta       900
taaaaattat tagtagagag aatgaaatac aaataataag ttgtataatt aagtgacctt       960
gcactaagtt atccatccat cacatatata acgctagtaa aaactataat atcaagcaag      1020
caacactctc accgactact gatacattca ccaattgata aaaatatga agtaaataag       1080 gaataacaag tttgttgttc gtttataaaa taaatgaca atatgcacta ggtttggtcg       1140
ggtttaaaaa acccacgggt tcacgggttt gggtactata ggaacaaacc cgtacccata      1200
aacccattgg gtacagattt atgcccgtta acaaacccat gggtatgaaa attgacccaa      1260
acctataccc taatggggta aaaacccatc gggtttcgga tttcgggtac ccattgccat      1320
ctctagacag gacaacctcg gccggtcctg tatgtaggcc accagcatcg gccagttggt      1380
acatccagcc ggggtcaggt cacttttact cgtctcaatc agacaatcac cgtccaccaa      1440
cgaacgccaa cgttgtcact tgtcaggtcg gttgagactt gtatttttt ttgtcctccg       1500 taaaaatcgg ttcaccag                                                    1518

<210> SEQ ID NO 60
<211> LENGTH: 20
<212> TYPE: DNA
<213> ORGANISM: Artificial Sequence
<220> FEATURE:
<223> OTHER INFORMATION: Chemically synthesized

<400> SEQUENCE: 60
ttcacgggag actttatctg                                          20

<210> SEQ ID NO 61
<211> LENGTH: 17
<212> TYPE: DNA
<213> ORGANISM: Artificial Sequence
<220> FEATURE:
<223> OTHER INFORMATION: Chemically synthesized

<400> SEQUENCE: 61
ccgattcatt aatgcag                                             17

<210> SEQ ID NO 62
<211> LENGTH: 17
<212> TYPE: DNA
<213> ORGANISM: Artificial Sequence
<220> FEATURE:
<223> OTHER INFORMATION: Chemically synthesized

<400> SEQUENCE: 62
acgtaaaacg gcttgtc                                             17

<210> SEQ ID NO 63
<211> LENGTH: 17
<212> TYPE: DNA
<213> ORGANISM: Artificial Sequence
<220> FEATURE:
<223> OTHER INFORMATION: Chemically synthesized

<400> SEQUENCE: 63
gtttaaactg aaggcgg                                             17

<210> SEQ ID NO 64
<211> LENGTH: 22
<212> TYPE: DNA
<213> ORGANISM: Artificial Sequence
<220> FEATURE:
<223> OTHER INFORMATION: Chemically synthesized

<400> SEQUENCE: 64
aataatatca ctctgtacat cc                                       22

<210> SEQ ID NO 65
<211> LENGTH: 15
<212> TYPE: DNA
<213> ORGANISM: Artificial Sequence
<220> FEATURE:
<223> OTHER INFORMATION: Chemically synthesized

<400> SEQUENCE: 65
gttgtaaaac gacgg                                               15

<210> SEQ ID NO 66
<211> LENGTH: 18
<212> TYPE: DNA
<213> ORGANISM: Artificial Sequence
<220> FEATURE:

<223> OTHER INFORMATION: Chemically synthesized

<400> SEQUENCE: 66
taggcacccc aggcttta                                          18

<210> SEQ ID NO 67
<211> LENGTH: 18
<212> TYPE: DNA
<213> ORGANISM: Artificial Sequence
<220> FEATURE:
<223> OTHER INFORMATION: Chemically synthesized

<400> SEQUENCE: 67
aattgaattt agcggccg                                          18

<210> SEQ ID NO 68
<211> LENGTH: 20
<212> TYPE: DNA
<213> ORGANISM: Artificial Sequence
<220> FEATURE:
<223> OTHER INFORMATION: Chemically synthesized

<400> SEQUENCE: 68
ggtccctaca acataaatag                                        20

<210> SEQ ID NO 69
<211> LENGTH: 20
<212> TYPE: DNA
<213> ORGANISM: Artificial Sequence
<220> FEATURE:
<223> OTHER INFORMATION: Chemically synthesized

<400> SEQUENCE: 69
ttcgtcccta ctatcaacgc                                        20

<210> SEQ ID NO 70
<211> LENGTH: 18
<212> TYPE: DNA
<213> ORGANISM: Artificial Sequence
<220> FEATURE:
<223> OTHER INFORMATION: Chemically synthesized

<400> SEQUENCE: 70
ctttaggcat cagcgggt                                          18

<210> SEQ ID NO 71
<211> LENGTH: 18
<212> TYPE: DNA
<213> ORGANISM: Artificial Sequence
<220> FEATURE:
<223> OTHER INFORMATION: Chemically synthesized

<400> SEQUENCE: 71
agcatctgcg taagcaca                                          18

<210> SEQ ID NO 72
<211> LENGTH: 19
<212> TYPE: DNA
<213> ORGANISM: Artificial Sequence
<220> FEATURE:
<223> OTHER INFORMATION: Chemically synthesized

<400> SEQUENCE: 72
ctgatgacac caatgatgc                                         19

```
<210> SEQ ID NO 73
<211> LENGTH: 19
<212> TYPE: DNA
<213> ORGANISM: Artificial Sequence
<220> FEATURE:
<223> OTHER INFORMATION: Chemically synthesized

<400> SEQUENCE: 73
gatcagattg tcgtttccc                                              19

<210> SEQ ID NO 74
<211> LENGTH: 19
<212> TYPE: DNA
<213> ORGANISM: Artificial Sequence
<220> FEATURE:
<223> OTHER INFORMATION: Chemically synthesized

<400> SEQUENCE: 74
gcatcattgg tgtcatcag                                              19

<210> SEQ ID NO 75
<211> LENGTH: 18
<212> TYPE: DNA
<213> ORGANISM: Artificial Sequence
<220> FEATURE:
<223> OTHER INFORMATION: Chemically synthesized

<400> SEQUENCE: 75
tgtgcttacg cagatgct                                               18

<210> SEQ ID NO 76
<211> LENGTH: 18
<212> TYPE: DNA
<213> ORGANISM: Artificial Sequence
<220> FEATURE:
<223> OTHER INFORMATION: Chemically synthesized

<400> SEQUENCE: 76
acccgctgat gcctaaag                                               18

<210> SEQ ID NO 77
<211> LENGTH: 20
<212> TYPE: DNA
<213> ORGANISM: Artificial Sequence
<220> FEATURE:
<223> OTHER INFORMATION: Chemically synthesized

<400> SEQUENCE: 77
gcgttgatag tagggacgaa                                             20

<210> SEQ ID NO 78
<211> LENGTH: 20
<212> TYPE: DNA
<213> ORGANISM: Artificial Sequence
<220> FEATURE:
<223> OTHER INFORMATION: Chemically synthesized

<400> SEQUENCE: 78
ctatttatgt tgtagggacc                                             20

<210> SEQ ID NO 79
<211> LENGTH: 18
<212> TYPE: DNA
<213> ORGANISM: Artificial Sequence
<220> FEATURE:
<223> OTHER INFORMATION: Chemically synthesized
```

```
<400> SEQUENCE: 79
ctagactgga aagcggag                                                 18

<210> SEQ ID NO 80
<211> LENGTH: 19
<212> TYPE: DNA
<213> ORGANISM: Artificial Sequence
<220> FEATURE:
<223> OTHER INFORMATION: Chemically synthesized

<400> SEQUENCE: 80
ccactttcat ccctagttg                                                19

<210> SEQ ID NO 81
<211> LENGTH: 17
<212> TYPE: DNA
<213> ORGANISM: Artificial Sequence
<220> FEATURE:
<223> OTHER INFORMATION: Chemically synthesized

<400> SEQUENCE: 81
gattgaatcc tgttgcc                                                  17

<210> SEQ ID NO 82
<211> LENGTH: 20
<212> TYPE: DNA
<213> ORGANISM: Artificial Sequence
<220> FEATURE:
<223> OTHER INFORMATION: Chemically synthesized

<400> SEQUENCE: 82
tctcataaat aacgtcatgc                                               20

<210> SEQ ID NO 83
<211> LENGTH: 20
<212> TYPE: DNA
<213> ORGANISM: Artificial Sequence
<220> FEATURE:
<223> OTHER INFORMATION: Chemically synthesized

<400> SEQUENCE: 83
tctgtggata accgtattac                                               20

<210> SEQ ID NO 84
<211> LENGTH: 20
<212> TYPE: DNA
<213> ORGANISM: Artificial Sequence
<220> FEATURE:
<223> OTHER INFORMATION: Chemically synthesized

<400> SEQUENCE: 84
agtaacatag atgacaccgc                                               20

<210> SEQ ID NO 85
<211> LENGTH: 18
<212> TYPE: DNA
<213> ORGANISM: Artificial Sequence
<220> FEATURE:
<223> OTHER INFORMATION: Chemically synthesized

<400> SEQUENCE: 85
ccagtgtgct ggaattcg                                                 18

<210> SEQ ID NO 86
<211> LENGTH: 20
```

-continued

```
<212> TYPE: DNA
<213> ORGANISM: Artificial Sequence
<220> FEATURE:
<223> OTHER INFORMATION: Chemically synthesized

<400> SEQUENCE: 86
ccagtgtgat ggatatctgc                                          20

<210> SEQ ID NO 87
<211> LENGTH: 18
<212> TYPE: DNA
<213> ORGANISM: Artificial Sequence
<220> FEATURE:
<223> OTHER INFORMATION: Chemically synthesized

<400> SEQUENCE: 87
ccagtgtgct ggaattcg                                            18

<210> SEQ ID NO 88
<211> LENGTH: 20
<212> TYPE: DNA
<213> ORGANISM: Artificial Sequence
<220> FEATURE:
<223> OTHER INFORMATION: Chemically synthesized

<400> SEQUENCE: 88
ccagtgtgat ggatatctgc                                          20

<210> SEQ ID NO 89
<211> LENGTH: 20
<212> TYPE: DNA
<213> ORGANISM: Artificial Sequence
<220> FEATURE:
<223> OTHER INFORMATION: Chemically synthesized

<400> SEQUENCE: 89
gtgtgctgga attcgcccctt                                         20

<210> SEQ ID NO 90
<211> LENGTH: 20
<212> TYPE: DNA
<213> ORGANISM: Artificial Sequence
<220> FEATURE:
<223> OTHER INFORMATION: Chemically synthesized

<400> SEQUENCE: 90
tatctgcaga attcgcccctt                                         20

<210> SEQ ID NO 91
<211> LENGTH: 20
<212> TYPE: DNA
<213> ORGANISM: Artificial Sequence
<220> FEATURE:
<223> OTHER INFORMATION: Chemically synthesized

<400> SEQUENCE: 91
gtgtgctgga attcgcccctt                                         20

<210> SEQ ID NO 92
<211> LENGTH: 20
<212> TYPE: DNA
<213> ORGANISM: Artificial Sequence
<220> FEATURE:
<223> OTHER INFORMATION: Chemically synthesized

<400> SEQUENCE: 92
```

```
tatctgcaga attcgccctt                                         20

<210> SEQ ID NO 93
<211> LENGTH: 20
<212> TYPE: DNA
<213> ORGANISM: Artificial Sequence
<220> FEATURE:
<223> OTHER INFORMATION: Chemically synthesized

<400> SEQUENCE: 93
gtgtgctgga attcgccctt                                         20

<210> SEQ ID NO 94
<211> LENGTH: 20
<212> TYPE: DNA
<213> ORGANISM: Artificial Sequence
<220> FEATURE:
<223> OTHER INFORMATION: Chemically synthesized

<400> SEQUENCE: 94
tatctgcaga attcgccctt                                         20

<210> SEQ ID NO 95
<211> LENGTH: 20
<212> TYPE: DNA
<213> ORGANISM: Artificial Sequence
<220> FEATURE:
<223> OTHER INFORMATION: Chemically synthesized

<400> SEQUENCE: 95
gtgtgctgga attcgccctt                                         20

<210> SEQ ID NO 96
<211> LENGTH: 18
<212> TYPE: DNA
<213> ORGANISM: Artificial Sequence
<220> FEATURE:
<223> OTHER INFORMATION: Chemically synthesized

<400> SEQUENCE: 96
ggtcttgcga tgattatc                                           18

<210> SEQ ID NO 97
<211> LENGTH: 18
<212> TYPE: DNA
<213> ORGANISM: Artificial Sequence
<220> FEATURE:
<223> OTHER INFORMATION: Chemically synthesized

<400> SEQUENCE: 97
gagaggaatg gcagcaga                                           18

<210> SEQ ID NO 98
<211> LENGTH: 18
<212> TYPE: DNA
<213> ORGANISM: Artificial Sequence
<220> FEATURE:
<223> OTHER INFORMATION: Chemically synthesized

<400> SEQUENCE: 98
catgacgggt ttgagatt                                           18

<210> SEQ ID NO 99
<211> LENGTH: 18
<212> TYPE: DNA
<213> ORGANISM: Artificial Sequence
```

<220> FEATURE:
<223> OTHER INFORMATION: Chemically synthesized

<400> SEQUENCE: 99
aatctcaaac ccgtcatg                                                18

<210> SEQ ID NO 100
<211> LENGTH: 18
<212> TYPE: DNA
<213> ORGANISM: Artificial Sequence
<220> FEATURE:
<223> OTHER INFORMATION: Chemically synthesized

<400> SEQUENCE: 100
tctgctgcca ttcctctc                                                18

<210> SEQ ID NO 101
<211> LENGTH: 19
<212> TYPE: DNA
<213> ORGANISM: Artificial Sequence
<220> FEATURE:
<223> OTHER INFORMATION: Chemically synthesized

<400> SEQUENCE: 101
gatcaacccg gagaggaat                                               19

<210> SEQ ID NO 102
<211> LENGTH: 18
<212> TYPE: DNA
<213> ORGANISM: Artificial Sequence
<220> FEATURE:
<223> OTHER INFORMATION: Chemically synthesized - b05104h sequencing
      primer

<400> SEQUENCE: 102
ccatgacggg tttgagat                                                18

<210> SEQ ID NO 103
<211> LENGTH: 20
<212> TYPE: DNA
<213> ORGANISM: Artificial Sequence
<220> FEATURE:
<223> OTHER INFORMATION: Chemically synthesized - b05105c sequencing
      primer

<400> SEQUENCE: 103
caaccgacct gacaagtgac                                              20

<210> SEQ ID NO 104
<211> LENGTH: 18
<212> TYPE: DNA
<213> ORGANISM: Artificial Sequence
<220> FEATURE:
<223> OTHER INFORMATION: Chemically synthesized - b05105e sequencing
      primer

<400> SEQUENCE: 104
atctcaaacc cgtcatgg                                                18

<210> SEQ ID NO 105
<211> LENGTH: 19
<212> TYPE: DNA
<213> ORGANISM: Artificial Sequence
<220> FEATURE:
<223> OTHER INFORMATION: Chemically synthesized - b05105f sequencing
      primer -continued

```
<400> SEQUENCE: 105
attcctctcc gggttgatc                                                  19

<210> SEQ ID NO 106
<211> LENGTH: 51328
<212> TYPE: DNA
<213> ORGANISM: Zea mays
<220> FEATURE:
<221> NAME/KEY: misc_feature
<222> LOCATION: (1680)..(3338)
<223> OTHER INFORMATION: opie2 marker
<220> FEATURE:
<221> NAME/KEY: misc_feature
<222> LOCATION: (25455)..(25512)
<223> OTHER INFORMATION: Maize genomic sequence displaced by MIR162
      heterologous DNA.
<220> FEATURE:
<221> NAME/KEY: misc_feature
<222> LOCATION: (43275)..(45086)
<223> OTHER INFORMATION: gag marker

<400> SEQUENCE: 106
agatctagag attcgtcatt tgtagaaagg atagaaaggt gattgctagg aagttagggg      60
caaaatgcaa gggtgataaa acttgcattt ggatccctaa ggaaattgtg actaaccttg     120
taggacccaa caagagttgg gtacctaagt cccaagccta aatttgcctt gcaggtttat     180
gcatccgggg gttcaagctg gattattgat agcggatgca caaccatat gacggggag      240 aagaagatgt tcacctccta tgtcaagaat aaggattccc aagattcaat tatattcggt     300
gatgggaatc aaggcaaggt aaagggtta ggtaaaattg caatttctaa tgagcactcc      360
atatctaatg tgttttagt agagtctctc agatataatt tgctatctgt tagtcaatta     420
tgcaacatgg ggtataactg tctatttacc aatgtagatg tgtctgtctt tagaagaagt     480
gatggttcac tagcttttaa gggtgtatta gacggcaaac tttatttagt tgatttttgca    540 aaagaagagg ccggtctaga tgcatgctta atagctaaga ctagcatggg ctggctgtgg     600
catcgccgct tagcacatgt ggggatgaag aaccttcaca agcttctaaa gggagaacac     660
gtgataggtt tgactaatgt gcaattcgaa aaagatagac cttgtgcagc ttgtcaagca     720
gggaaacagg tgggaagcgc tcatcacacc aaaaatgtga tgacaacatc aagacccctg     780
gagctgctac atatggacct cttcggaccc gtcgcctatc tgagcatagg aggaagtaag     840
tatggtctag ttatcgttga tgacttttcc cgcttcactt gggtgttctt tttgcaggat     900
aaatctgaaa cccaagggac cctcaagcgc ttcctcagga gatctcaaaa tgagtttgag     960
ctcaaggtga agaagataag gagcgacaac gggtccgagt tcaagaacct tcaagtggag    1020
gagttccttg aggaggaagg gatcaagcac gagttctccg ctccctacac accacagcaa    1080
aatggtgtgg tagagaggaa gaacatgacg ctaatcgata tggcgagaac gatgcttgga    1140
gaattcaaga cccccgagtg tttctggtcg gaagccgtga acacggcttg ccacgccatc    1200
aacagggtct accttcaccg cctcctcaag aagacgtcgt atgagcttct aaccggtaac    1260
aaacccaatg tatcttactt tcgtgtattt gggagcaaat gctacattct agtgaagaag    1320
ggtagaaatt ctaagtttgc tcccaaagct gtagaagggt ttttgttagg ttatgactca    1380
aatacaaagg cgtatagagt cttcaacaaa tcatcgggtt tggttgaaat ctctagcgac    1440
gttgtatttg atgagactaa tggctctcca agagagcaag ttgttgattg tgatgatgta    1500
gatgaagaag atgttccaac ggctgctata cgaaccatgg cgattggaga agtgcggcca    1560
caggaacaag atgaacgaga tcaaccttct tcctcaacaa cggtgcatcc cccaactcaa    1620
```

-continued

```
gacgatgaac aggttcatca acaggaggca tgtgatcaag gggagcacaa gatgatcatg    1680
tgatggagga agaagcgcaa ccggcacctc aacccaagt tcgagcgatg attcaaagga    1740
atcatcccgt cgatcaaatt ctgggtgata ttagcaaggg agtaactact cgatctcgat    1800 tagttaatt ttgtgagcat tactccttg tctcttctat tgagcctttc agggtagaag     1860
aggccttgct agatccggac tgggtgttag ccatgcagga ggaactcaac aacttcaagc    1920
gcaatgaagt ttggacactg gtgcctcgtc ccaagcaaaa tgttgtggga ccaagtggg    1980 tgttccgcaa caaacaggac gagcacgggg tggtgacgag gaacaaggct cgacttgtgg    2040
caaaaggtta tgcccaagtc gcaggtttgg actttgagga gacgtttgct cctgtggcta    2100
ggctagagtc aattcgcatc ttgctagcat atgccgctca ccactctttc aggttgtacc    2160
aaatggatgt gaagagcgct ttcctcaacg ggccgatcaa ggaagaggtg tacgtggagc    2220
aaccccctgg cttcgaggat gaacggtacc ccgaccacgt gtgtaagctc tctaaggcgc    2280
tctatggact taagcaagcc ccaagagcat ggtatgaatg ccttagagac tttttacttg    2340
ctaatgcttt caaggttggg aaagccgatc caactctgtt cactaagaca tgtgatggtg    2400
atttgtttgt gtgccaaatt tatgtcgacg acataatatt tggttctact aaccaaaagt    2460
cttgtgaaga gtttagcagg gtaatggcgc agaaattcga gatgtcaatg atgggcgagt    2520
tgaactactt ccttgggttc caagtgaagc aactcaagga tggcaccttc atctcccaaa    2580
cgaagtacac gcaagatcta ctaaagcggt ttgggatgaa ggacgccaag cccgcaaaga    2640
ctccgatggg gaccgacgga cacaccgacc tcaacaaagg aggtaagtcc gttgatcaaa    2700
aagcataccg gtcaatgata ggttctttac tttacttatg tgctagtaga ccggatatta    2760
tgcttagcgt atgcatgtgt gctagatttc aatccgatcc taaggagtgt cacttagtgg    2820
cggtgaagcg aattattaga tatttggttg ctacgccttg cttcgggctc tggtatccaa    2880 agggtctac cttttgacctg gttggatact cagattccga ctatgttgga tgtaaggtcg    2940
ataggaagag tacatcgggg acgtgccaat tcttaggaag gtcctgtgtg tcgtggaact    3000
ctaagaaaca aacctccgtt gcctatcca ccgctgaggc cgagtatgtt gccgcaggac     3060
agtgttgcgc gcaactactt tggatgaggc aaaccctccg ggactttggc tacaatctga    3120
gcaaagtccc actcctatgt gacaatgaga gtgctatccg catggcggaa aatcctgttg    3180
aacacagccg cacaaagcac atagacatcc ggcatcactt tttgagagac caccagcaaa    3240
agggagatat cgaagtgttt catgttagca ccgagaacca gctagctgat atcgaagtgt    3300
ttcatgttag caccgagaac cttttgcagg ctgcgtagta agctaaatgt cttagattcg    3360
cggaacttgg attgaattgt agcatacatg tgtttatgcc tttgatcatg ttcattctgc    3420
attttgttgc ttattgtggt gctcaagttg tacaaacact ccctggatct cacaagtccg    3480
ttgcaaagtg atgctgagag cacctagagg gggggtgaat aggtgatcct gtaaaaactt    3540
aacttatagc cacaaaaact tgttaaaggt tagcacaata attgccaagt ggctaaagag    3600
gagatcttgc acaatacgat tatcacagag aattcaacac agaggagaca tagtgattta    3660
tcccgtggtt cggccaagta caaaacttgc ctacttccac gttgtggcgt cccaacggac    3720
gagggttgca atcaacccct tctcaagcggt ccaaagaccc acttgaatac cacggtgttt    3780
ttgccttgct tatctttatc ccacttacga ggaatctcca cagattggag tctctcgccc    3840
ttacacttaa gattcacaaa gaagcacgga gtaaggagg gaagcaacac acacaaatcc     3900
acagcgaaat gcgcacacac acggccaaga atcgagctca aagactatct cacagtttct    3960
cacaagaaca gagctcgaat cacttagaat cacaaacgga tgcgcaaaga ctgagtgtgg    4020
```

```
atgatcaaga atgctcaaag gttgcttggt gtctccctcc atgcgtctag gggtcccttt    4080
tatagcccca aggcagctag gagccgttga gaacaaatct ggaaggccat ctttgccttc    4140
tgtcgtcggg cgcaccggac agtccggtgc ccgattcctt tccttaattg gcgaagccga    4200
ccgttgcaga tgcgggagcc gttggcgcac cggacatgtc cggtgcacac cggacagtcc    4260
ggtgccccct tccgaccgtt ggctcggcca cgtgtcccgc gcagatcgcg cggtcgaccg    4320
ttggctcagc cgaccgttgg ctcaccggac agtccggtgc acaccggaca gtccggtgca    4380
caccggacag tccggtgaat tttagccgta cgccgtcagc aaattcccga gagcggcctc    4440
ttcggccaag gcagcctggc gcaccggaca ctgtccggtg caccaccgga cagtccggtg    4500
ccccagaccg aaacagcctc ttggctgtac acagccaagt cttctcttct cttcttcttt    4560
ctgtttctaa cacttagaca aatatattag tacacaaaac caatgtacta aggcttagaa    4620
acatacctt t gctctagatt ttcactttgt tcatccatgg gcattgattc acatttaagc    4680
acttgtgttg acactcaatc accaaaatac ttagaaatgg cccaagggca catttccctt    4740
tcagatgcac agtttgaggg ggagatgtgt tacaacttga cccttt gaga ctaaccgtat    4800
gcttgagttt gcttgtttta gtctcaaagg agaattaaaa gggaaaaggt ggacttggac    4860
catgaaagac ttccactgca ctccgatgag agggtagctt attccaagtt catctcatgt    4920
actcttattg cctttgtatt cttattgaag attttggtga ggcaatgggg ttcttgggcc    4980
aagattgatc ctgttttggt gcttgatgcc aaaggggag aaaataaggg ccaaagcaat    5040
aaatggatca gctaccactt gagaaatttt gaaaacagta aatagagct tttggtttgt    5100
caaatctctt ttgttgtctc ttttgtcaaa agttggcctc ttgtggggag aagtgttgat    5160
tatgggaaaa aggggagtt tttgaaatct ttcctttgga atgactctcc ttatgcttca    5220
acatgtgtgt ttgacttaga gatagagatt tgagtttgat ttgcaaaaac aaaccaagtg    5280
gtggcaaagg atgatccata tatgccaaat tgaatcaaaa taaattgag ttttatttg    5340
aagtaatatt gcacttgttc tagttgcttt atgtagtgtt ggcataaatc accaaaaagg    5400
gggagattga aagggaaatg tgcccttggg ccatttctaa gtattttggt gattgagtgc    5460
caacacaagt gcttaaatgt gaattcatgt ttatggatga ataaagtgaa atcaagagc    5520
aaaggtatgt ttctaagtct tagtacattg gttttgtgta ctaatatact tgtctaagta    5580
ttggaaacag gaagaaaaag aaaagaaaag agttggctgt gtacagccaa gaggctgttt    5640
cggtctgggg caccggactg tccggtggtg caccggacag tgtccggtgg tgcaccggac    5700
agtgtccggt gcgccaggct gcctcggccg aagtagccgc tctcgggaat tcgctgacgg    5760
cgtacgacta taattcaccg gactgtccgg tgtgcaccgg actgtccggt gtgcaccgga    5820
ctgtccggta agccaacggt cggccgggcc aacggtcggc cgcgcgatct gcgcgtgaca    5880
cgtggccgag ccaacggcta aaggggggca ccggactgtc cggtgtgcac cggacatgtc    5940
cggtgcgcca acggctctct ggcgggcaac gggcggctgc gccattttag gaaggaaatc    6000
gggcaccgga cagtgtccgg tgtgcaccgg actgtccggt gcgcccgacg acagaaggca    6060
aggatggcct tccagatttg ttctcaacgg ctcctagctg tcttggggct ataaagggga    6120
cccctaggcg catggaggag tacaccaagc attcctacaa cattcctaag caccaagaca    6180
tcgatctcac gcattcgttt cattgtgata gcatctagag ctcttgttga gttgcgaact    6240
ctttgagttg tgttgcgagc tcttgttgcg acttgtgtgc gtgttgttgc tctgatcttt    6300
tgaagtcttg tgtgcgttgc tcattccccc tttgctctgt gttctttgtg aacttcaatt    6360
```

```
gtaagggcga gaggctccaa gttgtggaga ttcctcgcaa acgggattga gaaaaaaagc    6420
aagcaaaaca ccgtggtatt caagtgggtc tttggaccgc ttgagagggg ttgattgcaa    6480
ccctcgtccg ttgggacgcc acaacatgga gtaggcaagc gttggtcttg gccgaaccac    6540
gggataaacc actgtgtcgt ctctgtgatt gatctcttgt ggtattgtgt tttgttgaga    6600
ctcctttcta gccacttggc atttattgtg ctaacactta acaagttttt gtggctataa    6660
gtttaagttt tacaggatca cctattcacc ccccccccct ctaggtgttc tcacctatgc    6720
acccgtagct aggcttgagt caattcgcat attattggcc tatgctactt accatggctt    6780
taagctttat caaatggacg tgaaaagtgc cttcctcaac ggaccaatca aggaagaggt    6840
ctatgttgag caacctcccg gctttgaaga cagtgagtat cctaaccatg tttataggct    6900
ctctaaggcg ctttatgggc tcaagcaagc cccaagagca tggtatgaat gccttagaga    6960
tttccttatc gctaatggct tcaaagtcgg caaggccgat cctactctat ccactaaaac    7020
tcttgacaat gatttgtttg tatgccaaat ttatgttgat gatatcatat ttgggtctac    7080
taacgaatct acttgtgagg aatttagtag gatcatgaca cagaaattcg agatgtctat    7140 gatggggag ttgaaatatt tcttaggatt tcaagtgaag caactccaag agggcacctt    7200
cattagccaa acgaagtaca ctcaagacat tctaaacaag tttggaatga aggatgccaa    7260
gcccatcaaa acaccatgg gaacaaatgg gcatctcggc ctcgacacgg gaggtaagtc    7320
cgtggatcaa aaggtatacc ggtcgatgat tggttcattg cttatttat gtgcatctcg    7380 accggacatt atgctttccg tatgcatgtg tgcaagattc caatccgacc ctaaggaatc    7440
ccaccttacg gccgtaaaac gaatcttgag atatttggct tatactccta agtttgggct    7500
ttggtaccct cggggatcca cttttgattt aattggttat tccgatgctg attgggcggg    7560
gtgtaagatt aataggaaga gcacatcggg gacttgccag ttcttgggaa gatccttggt    7620
gtcttgggct tcaaagaagc aaaattcggt tgctcttttcc accgccgaag ccgagtacat    7680
tgccgcaggt cattgttgcg cgcaattgct ttggatgagg caaaccctgc gggactatgg    7740
ttacaaatta accaaagtcc ctttgctatg tgataatgag agtgcaatca aaatggccga    7800
caatcccgtc gagcatagcc gcactaagca catagccatt cggtatcatt tcttagggat    7860
tcaccaacaa aagggagata tcgagatttc ttatattaac actaaagatc aattagccga    7920
tatctttacc aagcctcttg atgaacaaac ttttaccaaa cttaggcatg agctcaatat    7980
tcttgattcg cgcaatttttt tttgctagat tgcacacgta gctcatttat ataccttga    8040 tcatatctct ttcatatgct atgactaatg tgttttcaa gtccatttca caccaagtca    8100
taggtatatt gaaagggaat tggagttttc ggcgaagaca aaggcttcca ctccgtaact    8160
catcctttgc catcgctcca agaaaaggac cttgtctttg ggggagagag taaaagccca    8220
aagcaaaagg actggacttc gtctttggta taatcttaac tcatttactt atgaccaaag    8280
gggaagatag tacttctatg ggctctaatg attccgttt tggcgattca tgccaaaggg    8340
ggagaaagta tgagcccaaa gcaaaggac cgcaccacca ccaatttcaa aaacttagtg    8400 cttttctaaga gtatttatca attggtatcc tattgtgttc aaaaggagga gaaattagt    8460 ttttttcaaaa atgtatatca aaaccctctt gaacactaag aggtggatct cctttagggg    8520
gaattttttg ttaagtcaaa ggaaaagcat ttgaaacagg gggagaaaat ttcaaatctt    8580
gaaaatgctt tgcaaactct tattcattta ccttttgacta tttgcaaaag atcttttgaa    8640
atggatttac aaaaagaatt tgcaaaaaca aaacatgtgg tgcaaacgtg gtccaaaatg    8700
ttaaataaga aagaaacaat ccatgcatat cttgtaagta gttatattgg ctcaattcca    8760
```

```
agcaaccttt acacttacat tatgcaaact agttcaatta tgcacttcta tatttgcttt    8820
ggtttgtgtt ggcatcaatc accaaaaagg gggagattga aagggaatta ggcttacacc    8880
tagttcctaa ataattttgg tggttgaatt gaccaacaca aataattgga ctaactagtt    8940
tgcccaagtg tatagattat acaggtgtaa aaggttcaca ctcagccaat aaaaagacca    9000
agttttggat tcaacaaagg agcaaggggg caaccgaagg caccctggt ctggcgcacc     9060
ggactgtccg gtgtgccacc ggacatgtcc ggtgcaccag ggggactcag actcaaactc    9120
gccaccttcg ggaatttcca gaggcgactc ggctataatt caccggactg tccggtgtac    9180
accggacatg tccggtgctc caaggaaggt cggcctcagg aactcgccag cctcgggttt    9240
tctccctcgc cgctccgcta taattcaccg gactgtccgg tgtgcaccgg actgtccggt    9300
gcaacctcgg agcaacggct acttcgcgcc aacggctacc tgcaacggca tttaatgcgc    9360
gcgcagcacg cgcaggagtc agaatcgccc atgctggcac accggacagc aaacagtaca    9420
tgtccggtgt gcaccggaca cccagtgggg cccacaagtc agaagctcca acggtcagaa    9480
tccaacggca gtgatgacgt ggcaggggc accggactgt ccggtgtgca ccggactgtc     9540
cggtgcgcca tcgaacagac agcctcccaa cggccacttt tggtggttgg ggctataaat    9600
accccaacca ccccaccatt cattgcatcc aagttttcca cttctcaacc acttacaaga    9660
gctaggcatt caattctaga cacacccaaa gtgatcaaat cctctccaat tcaacacaaa    9720
gccctagtga ctagtgagag tgatttgccg tgttcatttg agctcttgcg cttggattgc    9780
tttctctctt tcattctttc ttgtgttcaa tactcacttg taaccaaggc aagagacacc    9840
aattgtgtgg tggtccttgc ggggaggttt ttctcccggt tgatttgaga agagaaagct    9900
cactcggtcg gagggaccgt ttgagagagg gaaagggttg aaaaagaccc ggcctttgtg    9960
gcctcctcaa cggggagtag gtttgagaga accgaacctc ggtaaaacaa atcctcgtgt   10020
ctcacttcat tatttgcttg cgatttgttt tcacgccctc tctcggactc gattatattt   10080
ctaacgctaa cccggcttgt agttgtgttt atatttgtaa atttcagttt cgccctattc   10140
accccccccc ctctaggcga ctatcaccag gcggtagtcc gcgagccaca gttccggtct   10200
cgtttccccc gaatacttcg tgatagtagt cgggggtcgg aaccgggtcg gaacgacgc    10260
ccgtcggatg gcccgactga aggcttgcgg accgggtggt tcgggcgagg gactccgatc   10320
cctccccact gtcgtagcgc ccccccacgc ctggggtggt agcctcggcg cacccttccg   10380
tcgaggtggg cccgacggtc gcgtcgatgg tgctcgttgc cgaggtggcc ggggccgca    10440
ggcgcggtgt tgcgcgtgcg tccggtatag accgaggctt cccgcataaa ttgggaagtc   10500
gcggcgtgag gttccgaggg gtatccccgc ctccgggagg cagtgctctc ggcccgtcgg   10560
gccgcagcgc cttccaggag attcttgagc tctccctgga ttcgccgacc ctcggtggtt   10620
gatggctccg gcatcgtgcg gaggagcatc gctgcggctg ccaggttctg accaaccccg   10680
ctggatgcgg gcgcgcggcct gagcctgaca tcgttggcga cgcggtgctg gagaccttgg   10740
ggcaggtgac gtatttctcc ggccgagggt tggcccgccc atacctgccc gacgtcccgg   10800
cggatcgtct caagcgcccc tgttccctcg tcgagcctgg cctgcgcccc gcggacttgc   10860
tcgagctgtg ggtcgtgacc ccccgccgga acggggacca cagctagctc ccgcgggatg   10920
tcggcgcgag ggcaccggcc taggaaaatc accgtcctcc ggcatgccaa gatggttgcc   10980
ttcgagggga tccctagct cgacgtggaa acattgcgg cttgggccgc agtcctcgtc     11040
gtcaaggctg cggcttccgt cggaacagtc ggagaggcag tagtcacatg cggtcatgaa   11100
```

```
gtcccgcatg gcactggggt tgccaagtcc agagaaaccc aacagatgc tgggatcgtc    11160 atcttcctcg gacccagagg gcccgtaggt cgagacgtcc gtcaatcggt cccaaggcga    11220
ccgcatacga aaccccagtg gggttgcact cgcctcaatg agagcgcccg ccaaagcgag    11280
gtcgcttggc gggtcgaggc cgagtcgaaa tgacgtaaga tgggagttag ttagtacctt    11340
ttggtcgacg cggagcgacg tagtcacatc ggggactggt tgcaccgtca tctcaggtac    11400
gagggcgacg tcctgcaggc tttccgcgag cgtgctggcg tcttcttctt gctcgggatc    11460
agcgtgtcgc gggggacgg cgcttgcctt cgtctcgaac gcgaggtcga cgcccggcgt    11520
gccctccgtg ggggcgctgg ggacgtcgat tcgctcgaca gccgacgaag cgcggcctcc    11580
cacttggcct tggttgcccc gcctcctcct ccgttggcgg gggagaggac ggggcgagct    11640
cgaatgttgt ttttccaccg cgcggggaag atgtcgtcgg ttccgccgcc gacgggcggg    11700
atgtcggccg ccattgtcgt tgtcgcgcgg cggtggaagg agtatcatgt cgtagctgcc    11760
gtcgaaggac atgaactcaa gactcccgaa acggagcacc gtcccgggcc ggagaggttg    11820
ctggagactg cccatctgga gcttgacggg aagctgttcg tcagcacgca gcaggcccct    11880
acctggcgca ccaactgtcg gcgtttcgag accgggggt ccccgagccg acgagtgagt    11940
gtgccgcgtg ccccagccca gatgggtcga gcgcgtgggc gagcgcgaag gggggagagg    12000
cgaggtgtcc ggagacgggc gtgagagagg tggagatccc gcggccttcg tgttcgtccc    12060
gcgcccaggt cgggtgcgct tgcagtaggg gggttacaag cgtccacgcg ggtgagggaa    12120
gcgagcggcc ccaagagagc gcctgtctcg tcctcgtccc cgcgcggcca accttctcta    12180
agaaggccct ggtccttcct tttataggcg taaggagagg atccaggtgt caatggggg    12240 tgtagcagag tgctacgtgt ctagcggagg gagagctagc gccctaagta catgccaatg    12300
tggcagccga agagatcttg gcaccctact ggcgtgatgt cgtggctgtc ggaggagcaa    12360
cggagcctgg cggagggaca gctgtcggag cggtcgagtc cttgctgacg tccccttgct    12420
tccgtaagag agctgagagc cgccgtcgtc acagagcttg tggggcgcca tcattgccca    12480
tctggtggag ctagccagag gggacaccgg tcttgttctt cgtgacccga gtcggctcgg    12540
ggtaggatga tgatggcgct tcccgttgac gtggcgggcc tgtgccctag gtcgggcgac    12600
gtgggggctc ctccgaagcc gaggtcgaat ctgtcttccg tggccgaggc cgagcccgag    12660
cccctgggtc gggcgaggcg gaggtcgttc ggtagaggcc agggcggagt ccgagccctg    12720
gggtcgggcg aagcggagtt tgtcgtcttc cgggtctcag cccgagtccg agctttgggg    12780
tcgggtggag cggagttcgt cgtcttccgg gtcttagccc gagtccgagc cctggggtcg    12840
ggcggagcgg agttcgccgt cttccgggtc ttagcccgag tccgagccct ggggtcgggc    12900
ggagcggagt tcgtcgtctt ccgaggctga gcccgagtcc gagccctggg tcgggcgag    12960 cggagcttcc tatgcgcct ttggcaaggc ctgactgcct gtcagactca ctttgtcgag    13020
tggcactgca gtcggagtgg cgcaggcggc gctgtccttc tgtcagaccg gtcagtggtg    13080
cggcggagtg acggcggtca cttcggctct gccgggggc gcgcgtcagg ataaatgtgt    13140
caggccacct ttgcgttaaa tgctcctgca actcggtcag tcggtgcggc gatttagtca    13200
gggttgcttc ttagcgaagc caaggcctcg ggcgagccgg agatgcgtcc gccgttaaaa    13260 gggggggcctc gggcgagaca gaagtccctc gaggtcggct gcccttggcc gaggctaggc    13320
tcgggcgaag cgtgatcgag tcactcgtat ggactgatcc ctgacttaat cgcacccatc    13380
aggcctctgc agctttatgc tgatgggggt taccagctga gaattaggcg tcttgagggt    13440 accctaatt atggtccccg acaactataa accccaaagg gttgttttag aagtctaggt    13500
```

```
agcttttttg tctattagag agagagtata ttagaaattt attttagtgt gtgatttctc   13560
gcaattgaga tatgttttta aagtagataa taataataaa ataaacatct atgatggagt   13620
tttgttgtgc atttggattt tgaatctcaa cttcaaaact gtattagaat ttgaaacttg   13680
aaaataaaaa ctgaaataaa aagataagga aaaaacaaaa ccactgtcgg gccactatct   13740 ccctagtcc tagccatgcc ccctcttcca tcagtcgagt gggtcagttg gccggcccaa    13800
caccgcacca gcatgatagc atctcgcacc cgcctggttg gtttcacagg cgaccatgcg   13860
ggacccacgt tcagcctctc cgcgctcgtg cctatggacg gtagtcggca gacaccaatc   13920 aatgggtcc gcgcgaccgc gcttcagttt ctcgtcgtcg tacgcatggg tcactgttag    13980
caccacggaa cacagaagac agcaagggaa agaggaaggg caacttggag cagaagaaga   14040
agaatagggt acgcaacgtg gcggatgttc tttgttatt cgttcatatc ctcagcagcc    14100
tagcacatag tctatatatg tcactcctga actggactgc cacaatacgg cttacacggt   14160
ccactgcggc ccaaccacat ttaagtttgg cttcctggtc ctcagcacgc gaggctgcat   14220
catctcctga tgtgttgccg ctgtctccag gtcttgattc ccacttgctg ccagcttctt   14280
cttgtcttcc gacgacgctt tgctgacatt ccctgtcct cgagcgccag cttggtccca    14340
gatcaacgct tttggaaacc gagcacgcag tgcctcaacg tcctcccagg tagccagatc   14400
ctcagtcatg cctgaccaga ccaccttgac ctgcgcgatt aactcaccac cacggtcaat   14460
gaagcggcat tgtagaatac atgtaggcac ctggataggg ccaacatctt ggggcagctg   14520
aggtgaggcc cgttgatcac gcccgatgac ccgtttgagc tgtgacacat gaaaaattgg   14580
gtgaatagag ctggaggccg gtaaagctag acggtaagcc acggaaccca gacgatcgta   14640
atctggaaag gaccaagaa tttgaaggac aacttgtgat tggagcgtgt agcaaccgaa    14700
gattggatat aaggttgtaa cttcaagtaa acccaatcac ccaccaaaaa cacgcgttca   14760
ctgcgctgct tgtcagcttg ccgtttcata cggtcttgag ctcgatgcag atgcaattta   14820
atgactttgg tcataagctc tcgttccttc aaccaagttt cgagctctgg ctgtggcacc   14880
acaatatcaa ccaaaattcc aaaatatcgc ggagtgtggc catataacac ttcaaagggt   14940
gtacgcccca aggttgaatg tactgtggta ttgtaccagt attcagcaac tgacagccaa   15000
gctgaccaac gtgaaggaca agtgtgcaca tagcaacgaa gaaaagtttc caagcattga   15060
ttcaagcgct ctgtttgtcc atcggattgg ggatggtaag aagaggacat ggacagattg   15120
gtacccgtga tctgaaatag ttgttgccag aatgagctag taaaaattct gtcgcgatct   15180
gaaatgatgt tgacaggtaa cccgtgtagc ttgtacacat tgtcaagaaa aacacgagcc   15240
actttagcag ctgtgaaggg atggagtaaa ggtaagaagt gtccatactt cgaaaattta   15300
tccacaacca ccaagatgca gttatagtga gctgaacggg gcaaaccttc aataaaatcc   15360
aatgaaactg tatgccacgc ttgtggtgga acttccaaag gctgcaatag gccaggatat   15420
ttagcacgat cgggcttgga ttgctggcat accgtacaag attgaacgta ctgtagcaca   15480
tcagcacaca tacctggcca atagaacatt tgtttcactt tgtgatatgt tgctggggct   15540
ccagaatgac ctccgaccgc cgtatcatgc atagcttgta ataccttctg ttgcagctgc   15600
aaattgccgc ccacccagat tctatttttg tgtcgaatga ttccttgatg caaggaaaaa   15660
ggagctttgt ctgcagaatt caaaattaat tgagccagca actgtttact agtaggatcc   15720
ttgtcatagc cttccactcc ctcctgcagc caagtaggca cactgtgaga aatagcacaa   15780
cagtgactat cttcctggac ttttcgagac agtgcatctg cagctccatt atccacccct   15840
```

```
tttctgtaga caatcttata ttgcaagcca gccaatttcg tatacatttt ctgttgccag    15900
atagtatgta aacgctgctc attcagttgt gctaaactcc tgtgatctgt atagataatg    15960
aactcagcca actgaagata ggacctccat tgagcaatgg ctaaaataat ggccatgtat    16020 tcctttcat aggtcgagag tccctgattt ttcggtccaa gagccttgct cagaaacgct     16080
aaaggatgtc cactttgcat aagcaccgca cccacaccat aataggaagc ataagtatga    16140
atataaaatg gctgggaaaa tcaggcagag ctaacactgg tgcagtgacc aatgcttgtt    16200
tcaaaacttc aaaagcttta aaatgatcca ctgtccacac aaataaagtg tgtttcttca    16260
agagatcaaa taaggtctac tgataaattc caaagtgctt gacaaatttt ctgtaaaaac    16320
cggctagacc caggaaacat cgcagttcct tagcattggt tggtactgcc caagaggata    16380
tggcttgaat tttactagga tctgtggata ccccttgctc actgatgata tggcccaagt    16440
aagcaatatt tgtttgagca aattcacact tagataattt gactttccaa ttatcagaca    16500
acaataattg caaaaccttc tgcagatgca gtagatgctc ttcaaatgac ttactgtaaa    16560
ccaagatgtc atcaaaaaaa ccagagcaca ttttctcaat actggtttca gggtttcatt    16620
cgttgcactt aagaatgtgt taggagcacc tgtcaagtca aaagccatca ctctaaactc    16680
atagtggccc acatgagttt gaaatgctgt tttatattct tcgccagatt tcaaaagaat    16740
ttggtgatat ccagctctga gatccagttt actaaaccat ttagagtggg cgagctcatc    16800
aatcaattgg tcaaacacag gaactgggta tttgctcttg agagtgaggg cattcaaata    16860
cctatagtcc acacaaaatc gccatgtcat gtctttttc ttgaccaaca ccataggga     16920 agcaaaagaa ctattgcttt tctgaataac accttgatga acatctctt gaacttgttt     16980 ttcaatttca tccttcaggg ctggaggata cctgtaaggt ctgacagaca ctggctgagc    17040
accttccacc aaaggaatag catggtcaca atccctgctt gggggcaaac cctgaggttc    17100
gtcaaagact gagctgaact gttgtagcaa tgcttgaatt gcaggatggc tgtcaggaga    17160
agagcctacg gaactgacag attccatgaa caacaactct atcatagtat cagcaggtac    17220
ccctggggtg ttgccctgca gcagcacaga agagccttga tatggtataa ttagccactt    17280
ttgagcccaa tccactctca tgggactaaa ggatttaagc caatccatgc ctaccaccat    17340
gtcgtagtag ggaaggggca ggaatgaaac gtccgaagta aaactgcagt tctgaatctg    17400
ccattgtgcc tgcaacaatt tgtaatgaca agtcaccata gccccattgg ccacttgcac    17460
ttgcagagta gatgccatag atgtcacccc ttgcaagtgt ggtctaagtt gatcattcaa    17520
aaaggtgtgt gagctgccac tatctatcag aataagtaag ggatgattct gaatgctccc    17580
atttaatttc agagtttgtc gaccagtcga ccccgtccat gcagatttgg aaatagtcac    17640
gaacaactgt tctagagcag gttcaggtgg agataagtca gattcgggta cttcttcatc    17700
caccaataat gaccaaacct cctccatagc atgaagttga gcagtggcaa cacatttgtg    17760
accgggattc cacttttctg cacacttgtc acaaagaccc tttgctcgac gaaaacgtcg    17820
caacgattcc agcttatcag aatgagatgc agattgagtt gaatccttgt ttgaagtcca    17880
tttagttgaa gcagacaact gcacaccagt cttggggcca gcatgacttg aatatggttc    17940
agaacggcgc caacgtctcg ccgttgtggc ctcctcctgc accaacgcga gagaacaggc    18000
agtgtccaaa ttcgacgggc gttgcaccat aataacagct ttaatatcat cacgcaaacc    18060
atctatgaac cgcattgtgt aatacaatgg gtcagcattt gcttcatatg cagacaagtg    18120
atcaacaagt attgaaaatt gttctacata ctcagctacg ataccggact gatgtatgtg    18180
gaaaagttga cgaattaagg attcatgctg ctctctacca aatctatcat gaagctggcg    18240
```

```
acaaaattca gaccacgaca acatacgcac cctctgacca acagactgta accatgatgc   18300
agcacgccca ataaaatgca tagtagctac acgaatccac atatatggtt ccacgtcata   18360
catatcaaag taattttcac aaagcgtctt ccacaactga ggattgtccc cgtcaaagtg   18420
agggaaatta accctcggta ggttaccgtg cccacagcga aaccctcgt gaccgccatt    18480
cagttcagtg tgacgaacag aatcatcaaa tggatcaata cgaggtgaat cgtggtacgt   18540
acccttgacc gggacatggg tttgagcatg accatgccca aacccacgcg cccggtgaca   18600
tggttcagcg tggtggccaa atgggcccgtc agcgggttgt ttcccggcag atggatgctc  18660
ggacgccaac ccggaaggag tgaagagacc tggcttggtc tgatcagcgg cgatcgtctc   18720
acgctccatg aacttggtgg cacgcttgct ctcgaggaag aggttctcca gacgcctctc   18780
cacttctggg cgccaagtat ccacctcgga atgccccatc ttgagtgaga tgaagcgtgc   18840
ctccgcttgt tgcgccatcg cgtcgatccg ttgctcaatc gcgccgcagc gattctccag   18900
cgtcgcagcc atgcgctctt ccatctgcga caaggcctct agaaccttct gcatcgcgga   18960
atccataccg gcgaccgcag tggatcgagg gcgccgaccg ggtatgggat ccagattctc   19020
taggatgaac tagtctgata ccacctgtta gcaccacgga acacagaaga cagtaaggga   19080
aggaggaagg gcaacttgga gcagaagaag aagaataggg tacgcaacgt ggcggctgtt   19140
ctttgttatt tcgttcatat cctcagcagc ctagcacata gtctatatat gtcactcctg   19200
aactggactg ccacaatacg gcttacacgg cccactgcgg cccaaccaca tttaagtttg   19260
gcttcctggt cctcagcacg cgaggttgca tcgtctcctg atgtgttgct gctatctcca   19320
ggtcttgatt cccacttgct gccagcttct tcttgtcttc cgacgacgct ctgctgacag   19380
tcaccgcccg acagacttgt gggcccgctt cgccagaacc ttcgtctccc tcccgtaacg   19440
aactagggca caacacaaac ttgtacttgt gtagccgggg tgtgtttact ggccgaccgc   19500
accogcttg gactcgtcca ctgccccctat ataaacggtc gccccccgcc ctcgatcaat   19560
cagagtttag gagcccctgc tacctgttgt cgtgtggcgc cgtcgcaatg agctcgacgc   19620
cgcacgccat cgtaattcag ccacacctac gcttttgcct tgctttcggt aggaggtttg   19680
agggtttcgc cgtcgtacgt gggagctgct ggatgtttcg ttaggtgagg gaatctactg   19740
gaggcaggca ctgcgtgccg aggatcaccg ttgcatccca agccaccgtt cgacgtcgcc   19800
gactctcgcc ctcaatttag ttaccgacga ggaccccttg actgtttcgt ttgcttctca   19860
ctcgtaccta ggcacgagta gcgctttaga tcggttttgg ggcactcgga ttgctcgccg   19920
gtgttcagag attaccacag agtcacgctg tgctgagcgc gaggctcgac gctgcatgat   19980
cattgatcag accttgtccg tgttgtcttc attgaccaca gcttcgcata ccaccatttg   20040
gattggagaa atagagcgca aggtcgtcgg ttcgcgtgtg ctagcgagct gtcagggcgg   20100
agctctattt ctgccaccat gacgcgttgg tagagaaagg agcggcatca gttgatcagg   20160
attaaatccc gcgtacccct tcagcacatt aaatcaaagc cgtcagatct aatctagacg   20220
tttgtgattc gataatagcg tgtcggttta gtatttaaat ctggaccgtt gatctctaga   20280
tgatcgcctt aggtcgtgta ccagttagtg tagttgggtg aactttatta aagagcccct   20340
ataaaattta ggaattaacc tgcaatcacg tgatatttag aaagtcatgt agctaggtca   20400
tgttcttaac atattagacc cgatggattt tagaatcgga agtacacatt aaaggtatga   20460
ttctatactt agtacattag tttttgtgta ctaacacatt tgtctaagtg ctagaatgag   20520
aaaaaagaca aaggaaaaa gagttggctg tgtacagcca actgctgttc agtctgggtg   20580
```

```
caccggactg tccggtgagc ctacagtcgg ccgcgcaatc tgcgcgtgac gcgtggccgg   20640
gccaacggtc tgatgggggc accggagtgt ccggtgtgca ccagacagtg tccggtgcgc   20700
caacggctcc aaatcttcaa cggtcggctg cgccaaaata ggaaagcaat cagcaccggg   20760
cagtgtccgg tggtgcaccg gactgtccgg tgcaccaccc gacagaaggc aaggataacc   20820
ttcctggatt gctctcaatg gctcctagct gccttgggge tataaaaggg accectaggc   20880 gcatagagga gtacaccaag catactataa gcattcttga tcattcacac tccgtctctg   20940
ctcactcgat tgactttctt agtgatttga gctccgttct tgtggcgaat cttgtgctat   21000
tcatttgagc tcaagtcttg gctgtgtgtg cgtattgctg tggatttgtg tgtgttgctt   21060
ccctccccta ctctagtgct ttcactttga tccttattgt aagagcgaga gactccaagt   21120
tgtggagtaa atgaaactga accctaaacc ctaaaccctc taaaaatgac taaaatgcaa   21180
aatagacggc gcatacataa ctaggagtaa aatgtccgaa aaaaaatcgg ctcgagtctc   21240
gagactcgag tgccctctct gcctataaat cgaaccctaa cccttttcg tacctgtttg    21300 tgtccttagg gtttagggtt ctctgctcat tcgttcgcca cctcgcccca agacgtctcg   21360
ctagggtttc gccacagccg ccgccatgcc tcgccgcaag cttaggtaac cttctcctct   21420
ggcgcctcct agggttttgt ttcgagattc ggttgttcct tgcgttgacg ggccggggct   21480
ggctcctcct ggatctgggg ctcaggcgcg taggcttggg cgttagtaga tttgattcag   21540
tcggtatgat gtcgttaatc gtttgtttta gtatgtgcaa atgatactgg ggttgtgggg   21600
ataggattgc gcatgtttgc catgtttagt tgcagaaata tccggatctg tttcttgcgt   21660
tcaatgggct gggtctcttc ctgtttagat aattgtaaga aatggacggg tgttcataat   21720
cgacagagat ccgattgctt ctcgaataac cgattgcaga tactatctgt tcgcaggcgg   21780
ttcagacagg ggcatagaac aaatctgaat ccccacgagg gaaggtttat ttccattaat   21840
cctttctcgt taggattcgt atagatttac atatatacta caggttgtct tatgaggtgt   21900
ttggtatatt cttgaaagtt aattcaccag ggtagtggac tgaatcttat gaatgttgta   21960
tgtgtgtagc tgtattgtat tgtccgttta taatgcctct ttgagtagcc attacagtcc   22020
ctgagtactg tcttggttta gttaggggggc gcaaagcact ggacatctga tgtccactca   22080
ggccttttga gggggtacct cacctgtctt accaagaagt gcccccaag cagccttaga    22140 catacatcta cataatctct gtttgtaagt gcctcttga gtagccatta cagtccctgg    22200
gtactgtctt ggtttagtta gggggcacaa agcaatgggc atctgatgtc cactcacctt   22260
ttgaggggca ccttatctgt cttacaaaga agtgcccctc aagcagccct agacatatat   22320
ctacattatc actgtttgat ctgtcctcaa tgccacgtct tttcacttag tttttggcac   22380
tcatatttgc tttattgagt tgccactgta gttgtatata caatcttggt ttagttagga   22440
ggcacatgtg atcttgaaaa aaactgacat tgtagtgtta tcatctttcc tgttgaatgg   22500
tagacatgta atgcaaaaca ttcaaaagat tgcttgtgta cttgattagt atcaaggttt   22560
cagggagcga tgacatttct taatatattt ggaggactca acttagttac taactggact   22620
acaagtaaca aataatgtgc ctcttgtctt tattcatccc ttcttagatt gattcctaca   22680
gttaactgct attttcatca ttttgctgg tggaagatgt ggttgagctt gctttacagt    22740
attttggttt tgttagcttg tgttgcatct ctctctctac atttattatg tgttgatttt   22800
tgagttaaaa ctttgtttat gataaaccat gttgctttct ttggttaatt ttttttgctt   22860
aatgcttatt cccccactgt actgtcagga aggtccgcgg ctcacgcccg gctccacatg   22920
ctgctccagt gaggaaccca ccacagcctg gtaaagtgat tcacgcagac aataagtatc   22980
```

```
tttagaactg acattggcat ggtaatcatg cctcttttga ctctgcagta ttctattgtg   23040
gacatgtgtt tcaattatgt aactttagtt atattttttgt ataactgttt gctcagttgt   23100
tgagaatgtg ttcggtttgt tactataaca atgttgatga cataaatata ctgttaagtt   23160
tatattggaa tttgtggtac aagtctgaag ttgttgattg tgtttgaagc agagtcaatg   23220
gcatttcggt ttatatagag aattacagtt ccttgttttt tggtagaact ggaacctgtt   23280
tcagttctgt tcctaatgct tacacatggg tttgtgctac aagtatagta ttagtattac   23340
agagctcatt gttttggaat cttgattgct ttggaatcag aatcgtttat gtttagctca   23400
tattagtatt agtattacag ctcattgtgt ttatatagga gttttaatct gttctatttc   23460
tgttcctaag tgtcttctga cttttctttt tggcagcgcg ctaggctcgt cctccagctc   23520
ctgttcgtga tggtggtggt ggctccattc ttggaggaat tgggtccacc attgcttaag   23580
gtagttttca aagcttgttc ttttttgaat aacttcagca acaaacatta tcataatcct   23640
tgaattgatt tgaacgaaca cattgtttta ggtatgccat ttggtacgag tagtgccatg   23700
gcacacaggg ctgttgatgc tgtaatgggt ctccggactg ttcggcatga gattgttatc   23760
tcagaagctg ctgctgctgc ccctcctgct ccagtgatga acgctaatgc ttgcagcatc   23820
cattctaagg cttttccaaga tgtatgtctg cttgccacct ttatgctgcc ttgttttccc   23880
tcaatttgat gcatgaaaca tttggttact cacttctgtg atgtagtagt gaagttttat   23940
ggtgtctttt ttttttcctttt actgaacctg caaattactt aatcatcaaa ccttggccat   24000
caatcaagtt ttaatattat gggcatgatc ctaccgttgg ctttgttgag gtcatgttaa   24060
gaattgttaa cctgcatttt gtatactcat tcgatgatgt gttctcaccg atttttcttgg   24120 ttgatgcagt gtcttaacaa ctatggcagt gagatcagca agtgccagtt ctaccttgac   24180
atgttgaacg agtgccgccg tggtgttgtc tgcctgagct tttgctccaa ttgggattat   24240
tcatggattc tcttttcact cccatgtatc tcattaataa gacaccgtga aacttttaac   24300
cctctccacg aatgcaccat ggcatcacgg gttcatcttg ttgaatctgt ggttacgttc   24360
tctttatcct gtgttgttgg aacagacttc tgtctcttct ggtgatcata aatatttaaa   24420
tgaaccagtt gtgttggaaa atgttgtttt cttttgtctc tagactggaa agcggagttc   24480
tcgtcaacac ggttctttca actagggatg aaagtggtaa tccgaattgt tagtacaaat   24540
ttaatatttt aaaatagata tgtataaaat tttatgttga tcttttttat gttatcaagc   24600
acattagtat aaattagtat aaatatgaat aaaatattac ataaaatgtt ttatgtatta   24660
tttggtccct acaacataaa tagttgaaaa aattactaaa tttgttttcg aatctatatc   24720
gaagtttata tctattattt aagaaaaata taggatgaaa aggtttatct tttatgaatc   24780
tttacaagct ggatcttata aacaagaaaa taaatttata ttgtagattt tatatcctat   24840
ttattcgcaa tcaaagaaaa gcgactaaaa aactgattac cgagtaaata ctgtttccaa   24900
ccgttttcgt ccctactatc aacgccttct cccaaccgca gtcgatctgt ccgtctgtat   24960
caggcgcagc ggcacccctg ctgttcgact atctagacca tagaatattt taggtataca   25020
ataattttag ttccacgcta gaacatttta gttagaataa taacaagatt tgctattgat   25080
gtaggactcg cccgtcactg tctaaaaaag cattctgtcg gtcttattct ttaggcatca   25140
gcgggtgtac tatctcattt ttcctatcat attcctcagt actctgttaa gtataaatgg   25200 tctatttttac atgatgaact aataaaaacta attaaggatc ctaacttttt gtgaaggtaa   25260
tttggatcat tatgcattac catcctacgt atacctgctg cagcagcatc tgcgtaagca   25320
```

```
cagcctagat atatgcttct gtgtggactg aaaggagact ttgtttatca attagtatac    25380
tcccaaaaaa ctgatgacac caatgatgca aataggctgg gaatagtctg tctaatagtt    25440
tgagtgaatc atgtcactgt gcgtcctctg caggcagttg ttgacatgag cgcatcgtca    25500
ctgctgaatc gccatggtct gaaggcaaca gataaggcat actgggcctt gtggtagttg    25560
ttttactggg cctttttgta tgatctataa aattcactgg gatcaacccg gagaggaatg    25620
gcagcagatg cagtccccag ggtcctccgt cgccgcctga gcacccggca cccgcgctga    25680
accggagagg gacgcgcgga cgccgtgcag ctggtgcgga gggggctgtg gcagatgagg    25740
atgagacgcg tacgtggctg ggaaggccag caggccaccg ggtcttcgtc cagcccggcg    25800
cgagtggaca ggactagaga tggcaacggt tacaaacccg ctgggtttta ccgtcccaaa    25860
cccgtacccg tgaaaaatat ctatgcccat taaaaaaccc gtacccatga cgggtttgag    25920
attttgccca aacccgtacc catcgggtta acgggtaccc atgggttacc cgcgggtttc    25980
atctccaata tacctgttct tctcataatc aataagtatc gtaatgatta atgatatcat    26040
gatccaaaat ctatgtaatg aacaacgagt tcatgatttg gtataaaaat tattagtaga    26100
gagaatgaaa tacaaataat aagttgtata attaagtgac cttgcactaa gttatccatc    26160
catcacatat ataacgctag taaaaactat aatatcaagc aagcaacact ctcaccgact    26220
actgatacat tcaccaattg ataaaaaata tgaagtaaat aaggaataac aagtttgttg    26280
ttcgtttata aaataaaatg acaatatgca ctaggtttgg tcgggtttaa aaaacccacg    26340
ggttcacggg tttgggtact ataggaacaa acccgtaccc ataaacccat tgggtacaga    26400
tttatgcccg ttaacaaacc catgggtatg aaaattgacc caaacctata ccctaatggg    26460
gtaaaaaccc atcgggtttc ggatttcggg tacccattgc catctctaga caggacaacc    26520
tcggccggtc ctgtatgtag gccaccagca tcggccagtt ggtacatcca gccgggtca    26580 ggtcactttt actcgtctca atcagacaat caccgtccac caacgaacgc caacgttgtc    26640
acttgtcagg tcggttgaga cttgtatttt tttttgtcct ccgtaaaaat cagttccaac    26700
gacagatacc ccgacggtaa gcggacagcg ctgtcgtagt cgttttgttt gagtccacaa    26760
atgagccgaa gatgcaagca gcatatgcaa cgtgtgttac aaagaaaaga agtggatgca    26820
aaggcactac gagaatgaac tggtgccacg gaaagatgga accaaaccaa cgaactattt    26880
tttccctcct tttttttatt aatgcttcgg acgacgatag cagtttctgt acaactcttg    26940
atatataaaa aacaaacaat atgacggatt aacctaggca tccaatgccc cccaatttc     27000 ctcctgctat agcgccacac cttgctgctg cgacgactgg agccttccct tgaggaagcc    27060
cctgcacacc ttgctccaca gctccttgtc cggctgccgc acgtcgaagc tcgtcttggc    27120
cacttccacc tggcagtcct gccaacaaca aacaaaacaa ggacagatat ttttttttgt    27180
cctccgtaaa aatcagctcc aacgacagat accccgacgg taagcggaca gcgctgtcgt    27240
agtcgtttag tttgagtcca caaatgagcc gaagatgaaa gcagcatatg caaggtgtgt    27300 taaaagaaa agaagtggat gcaaaggcac tacgagaatg aactggtgcc acggaaagat    27360
ggaaccaaac caacgaacaa tttttttccct ccttttttttt tattaatgct tcggacgaag    27420
atagcagttt ctgtacaact cttgagttct gaagcacata taataaaaaa caaacaatat    27480
gacggattaa cctaggcatc caatgccccc caatttcctc ctgctatagc gccacacctt    27540
gctgctgcga cgactggagc cttcccttga ggaagcccct gcacaccttg ctccacagct    27600
ccttgtccgg ctgccgcacg tcgaagctcg tcttggccac ttccacctgg cagtcctgcc    27660
aacaacaaac aaaacaagga cagatatttt ttttccatgt cacagacaga cagacagaca    27720
```

```
gacagacaga gagacaaacg aacactcggc acgctgtcgt tactattatg attaattacc   27780
agtatgtggt tgtggcggag gaggcggtcg gcgatgctca tgaggacgtc cttgctgtac   27840
tccgggtggc cctggacgcc catggcgcgg ccgccgaggc ggaacatctc gacgcgggtc   27900
ttgtcggacc gcgccagcgc ctcggcgccg ggggcagct cccacacctc gtcctggtgg    27960
aactcgatca ccggcatgtg cacgggcagc ttcagcggcg cgaacagccg cgccgccgcc   28020
gccgtcgggt ggatgcagct caccccgatg tcccagccct tggccgaccg ccccgtgcgc   28080
ccgcccagcg cccggcacag gatctgcgtg ccgcaatcaa acagcttcag gagttaagac   28140
ggaagtgtag tagccacagg agtttagagg tacgtgtgcg taacgtggac gcgtgcaagt   28200
ctgcctggca tcggcgcccc accaccgaca gggccgatgg acgcaactaa aacgttttct   28260
tcgggaacac gccaagtaat tgattcatgt gcacacagac tgtcccccctt ctgtttgtag  28320
tacgatattg ggaacctcct aggattccac tgctaaacaa ttggtgtctc ctgttcctgc   28380
gtacgagtac gacgacggaa gacttcgcgg ccacaagagc aatccaaatc caaggctctg   28440
gctctcggac cacagggaca gcgacagtgt aagagctctt tgaagttgcg agtgttatta   28500
acatagaacc aagtaataat taggagaaga ggtcagtacg tcctcacgcg tcgaggcacg   28560
tctctgacaa aagcgtggtt cgcgcgggcg attgcgtgcg cttgggcttg ggcgctaccc   28620
gcacgccctt gggcgtgatc tgatcccctg agctgctggg ttggtacgct agtagcatcg   28680
tcatcccaaa agcaatctcg ctcggcaggc gagatgcgtc acgccatttg cgttcttcgt   28740
cctcctcctc cttcccgggg gatttgattt taaaatttgc aggcgcggtt tacgcgccac   28800
tttgaggcaa acaaaccggc gaaccggaat aggggaaccg ctcgctcctc taagccaggg   28860
caggggcgca gggctctgtg actgtgagcc aaacgtccgg ccacagacgc agcgggccgt   28920
aggagatcct gcagaacaga tacccactcc acttgtctgt gtgccaacaa caacagcaac   28980
ccagctgcca cggccacgtc acaccacgtg aatcagcgat gtcagcctcg agccttaacc   29040
cttttgtttga gagatgctgc cgtgtcttaa acctagatta gcgtggagtt tgtagtcact   29100
aatccatcca atcagtcccg tgtccgtctg tttgcttcga cccgaatcaa accaggggcc   29160
tctgcttcta tgaactgaac tggcatggac tgaaacaaaa cagcgtcatg gcagaagcaa   29220
gagctctata ttgtgcgctc taaatggaga ttggtaaaac tcgtagaatt gggggttcgt   29280
ttcttccgtc aaactctaac tgtgggcttg atgctagcac tgagtcacct ttgtcattct   29340
ctggggaaaa aaaataaggc atctttccgt ccccattgct actgctcacc aattaagcag   29400
ccagtaccgt ttgtactagt caaaatgcat caagaacgac cacgggtcgc cgtaaaaaaa   29460
aagaaagaaa ataatagaaa agaaaaggtg cgccgggtgg acgggaaggc gctaggctag   29520
aagagcggca gccccaccag gtggtgcccg cagcgtcccg cggtcccgtg attcaccagc   29580
gacgacggag aaacccagct acgcgcggaa gggactagac gagaaccaac cgcaccgcac   29640
ctaaacccaa ccaaacagca agtcgaacca aacatggacg gatgggatgg gcacctggtg   29700
gccgaagcag acgccgagga cgcgcttgcc ggcggcgtgg acgcggcggg tgaggtcgac   29760
gagcgcgagg atccagggct cgtcgccgtg cgcgtcggcg cagctcccgg agatgacgaa   29820
cccgtcgaac ccggctgcct cggcgtcggc ggggagctcc ccgcggacgg cgctgtacac   29880
ccgccacctc tcgccgtcct cctccagcag cgcgcggaag acggcgaagt agccgccgta   29940
cttctgccgc acgtactccg agtcctgccc gcactgcagc accgcgtacg agcccgcccg   30000
cgaggggggcg gcgcggcgg cggcggcggc ctccagcgcg gccgacgcgg cgttgtcgag   30060
```

```
cggcccatt   cccatggctg   gcggcgtcgc   ggccaggcag   gcgcgtctcc   ggcccgggaa   30120
tggaggcggg   ggttgggcgt   cgcttggctt   ggctgactcg   cttgcggggg   gtgagaggtg   30180
gcggggagga   tgggggagaa   acggcgaggc   gaggcgaggg   cgatatttaa   agtaagcacg   30240
agcggttttc   cctcggattt   tttttatttt   ttcgtcgctg   gttttccatt   ttgctattat   30300
agtactgttt   ctgtttttt   ttactggtac   tggggctggc   cgctaccggc   ctaccgctaa   30360
catttggtat   ggacgtatgg   catggcaacg   gccagcaggc   gcgggacggg   ggctaccggc   30420
gagcggcggt   tttgctcggg   tccccttcac   tgctcgggtc   tttggccggg   tcctagtaat   30480
gggtacccaa   aatcgggtat   ccgatagata   aaaatcctat   tagagcatgg   atgtagcgaa   30540
ttttaatatc   tatggatatt   ttattaggtc   atttattaaa   tttcactcgc   tcatgcatac   30600
aatatactta   acaagcaaag   aagacaaacg   tggaccccct   aatctcacct   ttaaaacata   30660
tattgataaa   agagttttt   tttctagacc   gatcttgtca   aatactgtat   ctacctgcct   30720
gataaaagat   tcaaacagga   agagcaaaag   cgtatatcaa   attaattgac   acgggagtcc   30780
atttctgtgc   tcagagtaag   cgagcctac   aattgcaaaa   aaaaggggg   gggggggggt   30840
atgcatatgt   aatatctgat   gtcatttata   tatagtgcaa   cgattctctt   tcgtaccaag   30900
ttgcaagtcc   tcatatcgaa   tcgtaagtta   ttctgttttc   ctgtgtacat   atgaacatat   30960
ctatcttta   atacaaacag   catttttat   agtttttct   aagtacatat   gaacatatat   31020
ctatcttcta   atacaaacaa   catattttt   gtatagttt   tgttatgatc   atatgttttc   31080
ccatgctacc   gtttgtatta   aaacacggaa   actaaactac   actaatttat   tttattcata   31140
tttctttctt   taaaaaatg   tttttatcg   ttccatcctc   tctatttcaa   accgtaagct   31200
gttctggctt   tttttttcta   aatgcgtatt   ttagttatat   ttctagatat   aattagagtg   31260
tacataaaca   cataaaaacc   cacttactaa   aatcacaaca   acttacagca   atttaaaacc   31320
gtgagattgc   cgagcagggc   gagaaccgac   tgttagacat   gctcacatgc   atgtctgggg   31380
cattgtttga   ttttatttgc   ccgagaaatt   gctctgtttt   cattcgtaga   atttgtacta   31440
gtattttctt   accgaggctg   gctgggcata   cgtgcacgcg   cgcgatcgtg   cagcgacatg   31500
cacatgcaat   gcaatcaccg   cgtgacggag   taccgaggcg   aggtcgtcga   ccacgtgccg   31560
tatgggccgc   tggcacgtga   caccaccgat   tcggatcctt   atttattcat   tcatttgtca   31620
gtccccacgc   attgtattta   aaaattcaga   aacgtaagcc   cacttttacg   caaaaacaac   31680
tttactgtcc   gaaacgcctt   gtgcaactag   ctaggctagg   aggctaactc   attagtaaaa   31740
tgttgtgttt   tccaccccttc   ctttgtacta   attttataga   ctattagccc   ggacgagctg   31800
gctaggccag   acagggaaat   tatattttac   tttgacgcct   catctggatc   attggaattg   31860
aattccattc   taacaatatt   aatttaggta   tatatcaatt   aagctaatcc   ggttttatgc   31920
aaaatatatt   tatatactat   tattagcaag   atgtcggaga   tatttatgtg   ctacattttt   31980
actataaagg   agtgaaacga   agagtgtcat   gtaaattaca   gactagaaac   gaattctact   32040
aatgcataaa   atcatttcac   acactccacc   ccatgaattt   gagatagcct   tatatctgaa   32100
ctttggaaag   tggtggaatg   tcaaattcca   aactaaataa   gttatttat   tgagtgaatt   32160
ccaattcctc   taaaatgaag   ggatccaaat   gccccgtgac   tggaatttgg   agacgaagcg   32220
cgcgcagaat   attcgggtca   aatagaatca   gctacatact   atgtgcatta   gggctcacat   32280
aaataatcca   tatcttgagg   agtatcaaga   gagtaagtgt   aaaaaaaata   caagagacat   32340
atcttgatga   agagatgtat   ctagctcagt   tctctaagtc   tagatacagt   ttcgtccata   32400
caacccacat   aaatgagtta   tatcatgaga   gattctagtg   aataagatat   atgattatat   32460
```

```
acaaaaatag tttcttatat gttttttgt attttgaaaa ccgaactgga gtcttaaggt   32520
tgcacatgcc ctggatgtat ctagtgtttg taaaacctgt ttgtaaaacc gcaacaaagt   32580
ttctacattg tacatgccct tagggatgtt accaattttg gtagtgaaac gcaataatga   32640
attaagcaat aattcaagcg gatcagaatt aaatgagacg tgtggtgtag actgtagaga   32700
gtactctacg atatgtagtg ggatacttgg agcagtaatt attactaaac atgaggtgta   32760
gtaaacattg acgggataac gctgcacatt aaatactagt atcagtaaac gatgcaatat   32820
gcacgatcat ggtccgagag aatattcgga tcaacacatc tatctcctgc gtttatatat   32880
tattaaaact gaacgttacc gttttttgtt agtagtgata aagatcgatt aaggtaactc   32940
cagcaacgtt ggatgtgtat aacactgttt tgtattgtag atgtactctt tttatataag   33000
gagaagttta aaatagaaat tacgataacg taaagtgggt ttttaccggc taaatttgaa   33060
cgttttccct ttccttccct ggtcctgtac ttgcagtatt gcactgtcgc ctgtcggttc   33120
atcgatcgga acgacgacgt cgtcgcgcgc ggcactatgg gcactagtac tttggtggca   33180
gtggcacacg ttcgtagtgt gtgtcacttt ggtgtctgga gcctgctgga gcaagacagc   33240
aagtcaggct gaggccggct actcagctgg gcgagtgggg gttgctgcga gctttggcgg   33300
atatcagggt atgcatatat ggcaacggct ccaaaaacgc gctgctgcga ctgcgatgcc   33360
ctgcagcatt gcaatggctg gccggccggt gcgcgttgct tggaagaaag atgctgtccg   33420
gtcggcgaac cagcctcgat cagccatgcg gttgtgatgc atgcgcatgc ttaacagtct   33480
ggaccctaac acgggctggg tgaagctgaa gaggacctaa tttttggtag ttttgtttga   33540
ctgaattatt ggtagttaag ctagattagt cctacttttg ggccggggct ggctttctgg   33600
cctagctcaa cacataattg ttttttttc tccatacgga cggcgtacat gcgttcaaat   33660 tttaaaccttt gaccttttac ttttattcac gtacggtgta ctgaacccgc gtagtccgg   33720 tagaaaaaag tttaaaaatg agagacacga cctcatgtta accgtcaccc gtgcatcatc   33780
gatggacgta cgttgacagc atcacaacga ctacaaaaat atcaaataat gcatgttaat   33840
ctgattctta gtatagcctt tcggtgtcgg caaattgcaa tgccgtgtgc cactatgttc   33900
attctcaaaa aaactgacca attgacgccg gactaatgct ggatcaacaa cgaccgcaca   33960
agtcgtgata gtaacggtct agctagtttt cacttttcag agattaattt agagacagct   34020
agctagctca ttagttagtt agcaaattag ctagttatt gttagttagc taatttcact   34080
aatatttttt agccaactaa ctatatatat cttcagtgca ttcaaacagt ccctatataa   34140
tctagattaa tttagttgta gctatttggc atcctagatt aatggaactc agattttcat   34200
cattagacaa cactgtccac ggtcgtattt cttcattatt tatgatactg tagcagtttg   34260
taggtacata aaaacgttga acatgttcaa acacattaaa aataaatatt tcatacacat   34320
tttgtgccca tatcatacta catttgaaat taaattacat tcttctcgca aataatacat   34380 tgacaattt atctagaaaa gtattcgcgg ttccctcttc atctcccaat ccggtatcgt   34440
gatgacttga tggtatttaa tcgttgtcgt cttcatcaca tcaatcaaat agttcttccc   34500
gtatatgtta ctacctcaaa tgaaaaaatt attccttcaa cattggataa cttggtaagt   34560
ccaataaaat tatgaatttc atcttcgaga cagcgaaaga ttgctcaata tgataagtgc   34620
aattggttga atacatctca tcatcacatg tcagtcaatt aattagtcga tcaacgatga   34680
aaattaagcc ctgaggttca ccgtgctaca aaacgacatg attgtgtgta cagttttcgt   34740
actatttaag ttttacctcc ttcctatatg aaacataatt cctcaacgat tgtttgcttc   34800
```

-continued

```
ggattaaagc ggactatttta gattggtgta ggtgtaatct ataaaaacaa aagtactata    34860
gaaccagtag aaaccggtat agattaaagt caagggaacg actgaaagtc cacaaagcta    34920
ctggattcca tgagcttctg tagataacaa gcccgacatg gcgacgtcca catgggccgg    34980
gtctgaaaat tcccttccca gcaaataaag agaaactagc aaattgttca tatatgctac    35040 ggttctatttt atacttatgt atagaatata aaatataaag atatgagtgt attgttagtt    35100
atgtggatat gaatgtgagt ttagagctaa taatcatagt tcgaatctct atttgtatat    35160
aattttagca tttttataat ttaaatgtga ggtatacgat gaaaatcata aaactaggaa    35220
aattagtgtt ttaatatagt acagatatta ttctctgaac caaagacaca caccagaata    35280
caactcacat atgcattgca cgtgtgaagc tccgacacac agggcgcaac aactcagctg    35340
ctttctttac gtgatcagat tgctagagta cttcacaaag gacgccgag agagtatcgt    35400 tcaccaacct ggcagtggca gttgccgcat tgtactagtg tacaaaagcc cagctgaacg    35460
gtgatcagtg gcctcccaat gccattctgt gtaggcgatc acagatctat caacaccacc    35520
aaacccaagc cagcacactg caaaacacca aaaggattga agcaagctgc caaatggcac    35580
gcgttgcagg aacaccgacc ctgcctgatt cagagtcaga aatgcaatta tagacgagtc    35640
tatgggcatt gtcactgaca gaatgacagg gcaaagatac cacagtttca cgcgaaaaca    35700
tggccgtggc acgttggccg ctcgaggcaa caacttctat attggcatag ccagaatgat    35760
aatattgttg tacaactcag ttagagatcg agtcgcacga tcatgctcgc actctctgat    35820
tagggacgta acaatctgtt ggttaataag ttctcctttc ataccacata ataaatagtc    35880
aaagaaccga tacgcgaacc aacattcata ccgagattcg atctaatatc taccggccat    35940
cttttcgact ccccgaacca tagccggagt ggccatgggc atttctccgc ccttgatcag    36000
catggcatct ccttccaatt ctggaggtac aaatctatgt tctatgattt ctaatggcta    36060
ggattacgag tcgaggtctt aaaatctaat agtggtatca aagccatggt tttaggctcg    36120
ggctctaact ataaatgaca gttttcctta agttttatga caaatccga gaaaacacc    36180 tcttaactct ttgtattcgt gttcctactc acgtagaaca agcaaaggg gagaaagaaa    36240 ctctaaccca acatttccac ctttcccaaa ctctaatcct aaggcagtcc ataatctgag    36300
cacccaagca cacaaagaaa gggaaagcag acgttaggaa agcagccatg tgctatatat    36360
tcgaagacct agcctacaca cacatctgtg aaactgtatt aaattgttaa atattttttag    36420 tttgttaaat atttttaaat tacgttaact cgtctttttct agttattact tatagcttca    36480
aatctagttt catttacgat aaagttcaat aatcattatc cttctcttga ttactatttt    36540
catttggtat gaatcatgat cggttgtttt tctctaaatg tttgggtgag taatctttag    36600
gcttgacaaa cgaggatggt gaattcattt tttacgcatc tcatattatt taaagtgcat    36660
cacttgtaca cgagcacaaa ctcgatggca tgtaagtgat tttagggtgt gattgacaca    36720
caaaataggc tattgggagt gacaaacaac tcctcaagtc taaggactaa ataagaatat    36780
ttagaaaatt agtatatttg gatatctcat ttaaaaaccc attgaagctt gattttttggt   36840 taataacatc ctacattatt tttagggcct gttttgggaa ctagagatgt tctaagggct    36900
accactcaat tggataccta attagttgtt gactaatctt gattagttgg atgacagaaa    36960
atagaatgga actaggtaac taaggggggtg ttggattaca ctagagataa tagttagctg    37020
ctaaaattag ctgaagacat ccaaacactt tagctaatag ttaaactatt agctattttt    37080
agcaaattag ctaatactcc ctccgatttt tttatttgac gtttgttagt gaaaatctga    37140
actattgagt gtcaaataaa taaaaatgga ggtagtagtt aggtagacat ttgttaggta    37200
```

```
gctaattaca ctaacaatgt ttagccaact aactattagt tctagtgcat taaaacatcc    37260
tctgaggtga tgacctgcat gtggtatgac ttaagtcact tggcctcatt agcctaattt    37320
gcaactctac atgcagccat cgtcctagag ttaattggtc actagttagt tgctaactgg    37380
tcatagttag ttgtccgtgt gtgctagggt ttctttatac catatagata ggctttatcg    37440
aaaaaagata tttatttaaa cacgatctaa actcatagat tctcatatcg cacaattata    37500 ttttttatt tttaaattat ttgtatatat atttacaata tcaattctta ggcacaaatg    37560
aacatgtggt atactggtta gagactcttt gttttgtctc tcactgagtg agcaggattt    37620
gaaccctcat aggctgcgtt ggacgcacgg ccgcgagagt tagacgatcc acgataaaac    37680
tcatgtttta agggtgtgtt tggttgtaat gatgggaatg agacagaatg aaatgtgatg    37740
atcctcaaat aaggttgttt agtttagggt caagggttgg aacaagactg tcccagtatt    37800
gtcccagtta tccctcgaaa ttagagagac gagagggac gcgaggaaac gtctctgacc    37860
tggctatccc tatgtgtacc gcaaccaaac gcaccataaa ttaatgatga tgatgcttat    37920
tgttgttgaa agggttgcaa ccttaactac agcactaacc gccttatcca aggatcaaac    37980
acaaaaggcc aaacctgtga agatttactg ttgtattaca taattacaag attaccctgg    38040
aatgtttcgc atgtctgtaa accgaagaaa aatagttggt tccaaacatc ccaggtacta    38100
gcctgtgtgc accttggcgc gcagaggctg gagttgattt ttcctttatc gaaaaggaaa    38160
tatttctaag cctctaacca ttttttgcatt ctatgcagtg tcacctcatc agagagttaa    38220
tagttaatca agcctcccaa aaccttcatt tattaatgag ccagtgaaac tacatgatac    38280
catcatagta agaagttcca tgagtaacag gtcagcagat tcattttca tttgtgaaac    38340 tagattaaac aaaatattcc tttgggttga agttttttt gtctatttga cttttgggtt    38400
gtaacatgaa caaaaatata ccacctgcaa ctgaaacatt caaagattca aaggtacctt    38460
cctttggaat gtttacaagc tcaaatgcct ggagggtctc tgcagtgagg ccattgccct    38520
cacttcctaa cactaagcac agagattcat tcaacatcga atcagctagt tctttggaca    38580
gcgagtagat tttttttggat gcagcactac tactttctgg atggcctgcc atcatcttca    38640
taccatactt tgtcatcaat gcatgcaggt catgccaggt accagagaca ataggaagct    38700 gcaaagggc tccacgggct gcacgaacag ccttttccatt gaaaggacca caacaagccg    38760
gaagaaggaa tactccatcc tgatggcatt tgggttcaga ggttgttaag aggtgtagag    38820
ttggaacagc aaaaactaga gtgtttggtt ttctctattg gagattgtta gtttctatgg    38880
tgcctaagat cgattcctaa gtccctaata ctaatccgta acagaaagta aaacctcgat    38940
gacgagtaga tctgatctac tgagatcaat agggaaacac acttttgttg ttgttgttgg    39000
agcgttgtcg cagttgccgt cttcataccg ttgccctgca gagaagcagc aggcatcgga    39060
ttcgagccgc tgtgggttgt agcgtttcca ggcactccga cgcttaggtg atgggcctc    39120 tggggactag ggtttgggg cgaggtacta gtgttagtct ttcctgcgac ctttagtcct    39180
atatttatag cgttgtgtgc ccggaggctc caaccgaggt taacgtggcc cctctcaatc    39240
aagggtccgt ttaaggagat agatagttgg gattagccca atctgatcac tgatgaccag    39300
ctatagagga cacacccaac agagataact aatacatata aatcatgtat tgtgtatcct    39360
ataaaaaata ttgtgtaccg gaatcagaga taaggaggta aggacatcca tcctatctta    39420
cttaagagca gaatcaaatt cttttttagca aaggagaact ggagcacaat gaaatttagt    39480
ggcattcctc aaattctatg gtagagtagc aagattattt aacactatgc aatgcagcaa    39540
```

```
taatacagtc tgacatactt caataagcgg ccttcagaaa agaatatggc atacccattt   39600
gaaagcacaa gctgatctta tcagtgttcc gaggttacca gggtcctgca aggtaggggc   39660
accagtgcac catgcttacc atgagaccca ctgaacggat atgcataact acatttgctt   39720
caaacaaaaa cagcatgcat agattgaatt atgccttgca ttctactccg tccgttcttt   39780
tttatttgtc acggtttatt agtttagttc aaaaatgaac tagcgggcga caaatattcg   39840
agaatggata tagtattatt taaggatgac agcaatcatc tctctgcaca atggtggcct   39900
tgatgggtac tgcatatcct cacctgaatc ccatcaagga ctagaatcct ctttggacaa   39960
ctgaacaacc catcaagagc atcccatcct catggctcct gaggtcgcgg aaatggttag   40020
gcatgtgcat gacagcaatc gcctcggtgg aatcagccga ttgcatcccg gacaccttct   40080
tcatcaccgc gtcgctgcaa tacacgacat taaaggactc gcgcagcacc tccgggacct   40140
aggataagca agtaatcgat gacaaggggt agaagcacag gtttaggaag agaagaaacc   40200
tcgcaggaca tgtaaatatg acaagggcct ggagttgcag aggagtacag gatgggcacg   40260
aggccgacaa aatttgacca tcacatttgg tatgtttggt taactttcgc atcatatagg   40320
ataggagtat aggactagga tccatttcaa attatcgtgc atttcataat ggtttctgaa   40380
gctttggtca ccaagtattc ctatttctcg gctggaattt cacgtttgcg ctgcgaggga   40440
gtgtttcgtc ttcgactctt cgttcagaca gaccccgcgc ggactggagc caagccgctg   40500
ctacctgccg cacgctgcca ctgtcaggtc cgctcggcac atagcgacac agcgagcgca   40560
aacatttcgt tcgcactggt ttagcaaccg aaacgctcct ctatctaatc tcttatatca   40620
tcccctattt catacttatc tctacaaaca gtgttatata tagttccacg tcatatattt   40680
tccactctac tagaaacatg tttgattcgc ccctgactgt gccacaattt acaatttatc   40740
taaggttagt aaaaaaaagt tagataaagt atgataagat ggcgaactaa atatacccta   40800
gcgacacaac agcttggaac aacttcaacc agccctagtt agccactcgt agcttcatgg   40860 taaagattt ggataatttt ttacaagttt acacacttca tcacgacaaa gattgtgaat   40920
gctggatgtt tttggatttt gacacccttta cacacttcat aacgtgtgcc atctattaga   40980
ggagaaacga gaactgcacg cagcaacgca ccaggctaat aagtgacaac cgaacaagga   41040
aaggcgggaa gggggcaacc tggaaaatag agagcagagc agaactttat tcctcctctc   41100
aggaagtgtc cttgtcactc taaacgctaa cagccgaagg aaagaaggct gagagtgaga   41160
tttggagcca caaaaagata accggcatac tcagaactac atgggtccaa atttgagatg   41220
gtattcaaat tttagatggc aaggtctctt aggcacagct cattcgtctc ccattgcaag   41280
ttctagcgcg taatcatctc tttcctgaaa aacaaggagt ccattttatc tcagtgaagt   41340
gtctaataac ctataatcac actttgcaga tcagaaagta ttgttactca ccactggccc   41400
tcgtgcaaag tatctcccga attggagcca atatacctgc aaattgacaa acaacatgct   41460
ttgaagagcg aatttcctac tacatataga gctagatatt aattaatttc aaaaggtgtt   41520
ttagactacg tgcttgcctc atcttcatct tgagtctcga cttcaacatc gccagatggg   41580
aaaccaacac acaacaaagc atagccctga aaggaaaacc atacaataga actctaaaat   41640
ccttaagtac catacttgat aggcaacatc ggacaatgct cctttccact ttagctatga   41700
atttggattt atccgaattt atagctaagt gtctactatt ttaggacgaa gatagtactt   41760
tataattggt agctaatttg tattgatgaa catttctatg ttgcttggcc aagaataact   41820
gatcaataaa aaaatctatt gtcatatctg taacacaaaa aatacaaaat aaattgtggg   41880
tcacattgca atcataatcc ttccttaaaa gtcgacataa tagttatgca tcaaactcta   41940
```

```
gcaattgccc aggaacattc aggaaattgt acaaactagg taactgacta aactggagga   42000
caggttaaga gtgaaataca acctctcatt tccagaccat gtacacaggg aacaataata   42060
tgtcatgggc acaatactcc aatcgtgctt caactagtgg aagaaaaaat ggatgtacct   42120
tatcttttag ttctgcagat atcccaagtg cttcaggctg ccttatctgt cctgatttta   42180
ttcggactgc acagcttgtg cagcaacctg attaccaaaa tgagttttca attgttatat   42240
agaccacacg gaacaatcaa ataagagatg ctatccaatc aaaaggtatt catagttaaa   42300
taatatatca aaagccaatg gcatgggtag ttttttttt aatttatagt tgctataagt    42360
atttgacaaa tagaaagagt cccaaatgag tccaacatgg ttctgactac atattccaaa   42420
atcaaaacca acatcacact cccacacgat actatctata tcaacataaa ggaggatgag   42480
aaatagccaa cattcagttt gcacatattg gagcagctag tggtggagct tggccataaa   42540
aagaggacgg accattatga tatgaagtgt aaagagaagg gagacagatt agtatttcat   42600
cagttccgcc actcaagaca gggcttcatc aggctctatt tgtaacaaat gaagacggtt   42660
caagctgaag ggtgacattc atgcttagca cttagtgtag ctgctactaa ctaggcatgc   42720
ataatgagtc gcccaatagc ttactgtcat gtacggccgc acttacaggc gccgtcgtga   42780
cgccaggagg gctgcagatc gcgcagccaa ggcaggcgcc acaatcagtg gctaagttta   42840
gaaagataag gattagtttc cctcttgcat gccttaatca taggagggat tggttacgat   42900
tagtttcctt ttcatatgcc ttaataatag gagagattgg ttaagattag tttccttttc   42960
atatgcctta atcataggaa aggttggttg aaccagaggc tatatatatg ccgtgtaata   43020
ggctgggaaa taatcaagca agatcaatta tccaaaactg ctcttctcct ttgcctctct   43080
caagccaccg gtgaggaatc cctcacggtg aaggtctaga gcgcgactac gaactgcgta   43140
gccgcggtcc agcgacgttg ggcgtcgagg cgcttgacaa cctggtatca gcgtcacgtc   43200
gatcctcacc cacccgctct tgccctccac catccccttc cacgcccacc acctccaccg   43260
accactccat caccatggct gagcccacca tcaaggacct catggagctg atgcagtctt   43320
tccaaaccga gttggctgcc gtgaaagcca ccatgaagga caagtcgtcc tcgtcgtcca   43380
ccgacggcgg cggcgagcgc gaggatcccc ctcgtgtgga tcggcccccc aggttccaga   43440
agctcgactt tccccggttc gatggcacca ccgacccgat gctcttcatc aacaaatgtg   43500
aatcctattt tcgccaacag cgcaccatgg cggaggaacg cgtgtggatg gcctcttata   43560
atctggagga cgtcgcgcag ctgtggttca tccagctgca ggacgacgag ggcacaccat   43620 cctggggcg gttcaaggac ctcctcaatc ttcgcttcgg gccaccactc tgctcagcgc   43680
ccctgttcga gttggcggag tgtcgccgca ccgggaccgt ggaggaatac tccaaccggt   43740
tccaggccct gctgccgcgc gcgggtcgcc tcacggaggg ccagcgtgtc caactctaca   43800
caggcggtct ccttccccca ttgagccacg ttgttcgcat ccacaacccg gagacacttg   43860
atggggccat gagtctcgcc cgtcaagccg agcagctgga gttggcacgg ggaccgccac   43920
cggccgccag gggagcccct cgctctcttc ccccagcgcc ggcgcccaag cagccgctgc   43980
tcgccctccc tgcaccaccc gcgggcgcgc cccagccgcg accagagggt ccgcccttga   44040
agcggctatc accggaggaa caggcggaac ggcgccgcct cggcctctgc ttcaactgca   44100
atgagccgta caaccgcggc cacaaccgtg tctgccgccg catcttctac ctccatggcg   44160
tcgagctcac ggccgctgcc gaggaactcg taggggacga cccgcaggac ggcgcccctg   44220
tcttctccct cagggcagtc actggcatgc ccatctgcaa ttccatgcag gtgcgggcca   44280
```

| | |
|---|---|
| ccctaggcgc caccaccctc ctcgcgctcc tggacaccgg ctccacgcat aacttcattg | 44340 |
| gggaggatgc cgcccgccgc accggcctgc cgatccagcc gcacctcacg gccactgtgg | 44400 |
| ccaacggtga acgtgtcacc tgcccaggag tcattcgccg cgcccaggtc atcatcgagg | 44460 |
| gcgagccatt cttcatcgac ctcttcgtca tgccgctcgc agggtacgac ctcgtcctag | 44520 |
| ggactcaatg gatggtcacc cttggtcgca tggtgtggga cttcgtcgac cgctccgtct | 44580 |
| ccttcctgca ccaaggtcgc caggtctcct ggtcggacgt cgccgaccgt cagcatcccc | 44640 |
| tgctcgccgc taccacgaca ccgagcgccc tccttgagga gctcttgcac tccttcgacg | 44700 |
| gggtgtttgc tgagccggcg ggtctgcccc cacagcgagc tcgggaccac gccatcgtcc | 44760 |
| tcaagccagg ctctacacct gtggcggtcc ggccgtaccg ctaccggtg gcgcacaagg | 44820 |
| atgagttgga gcggcaatgt gccgccatgt tgacccaagg catcgtacac cgcagtgact | 44880 |
| cggcgttctc ctcaccggtt ctgctggtca agaagcacga cggggcttgg cggttttgcg | 44940 |
| tggactaccg cgcccttaat gccctcaccg tcaaagacgc cttccccatc cccatcgtcg | 45000 |
| acgagctcct tgacgagctg catggtgcgc agttcttcac gaagctggac cttcgctccg | 45060 |
| gtgatagtcg cctagagggg gggtgaatag ggcgaaactg aaatttacaa atataaacac | 45120 |
| aactacaaga cggggttagc gttaggaata agaaacgagt ccgcaagaga gggcgcaaaa | 45180 |
| caaatcccaa gcgaataagc aagtgagaca cggagatttg ttttaccgag gttcggttct | 45240 |
| ctcaaaccta ctccccgttg aggaggccac aaaggcctgg tctctttcaa cccttccctc | 45300 |
| tctcaaacga tccacggatc gagtgagctt tctcttctca atcacttgga acacaaagtt | 45360 |
| cccacaagga ccaccacaag attggtgttt cttgccttaa ttacaagtga gtttgattgc | 45420 |
| aaagaaggat caagaaagaa gaaagcaatc caagcgcaag agctcgaaag aacacgagta | 45480 |
| aatcactctc tctagtcact atggcgttgt gtggaatttg gagaggattt gatctctttg | 45540 |
| gcgtgtctag aattgaatgc tagagctctt gtagtagttg ggaagtggaa aacttggatg | 45600 |
| caatgaatgg tggggtggtt ggggtattta tagcctcaac caccaaaagt ggccgttgga | 45660 |
| aggctgtctg ttcgatggcg caccggacag tccggtgcac accggacagt ccggtgcccc | 45720 |
| ctgccacgtc atcactgtcg ttggattctg accgttggag cttctgactt gtgggcccgc | 45780 |
| ctgggtgtcc ggtgcacacc ggacaggtac tgtttgctgt ccggtgtgcc agcatgggcg | 45840 |
| tttctgactc ctgcgcgcgc agagcgcgca ttaaatgcgc ggcagagagc cgttggcgcg | 45900 |
| gagaagaccg ttgctccgga gacgcaccgg acagtccggt gaattatagt ggactagccg | 45960 |
| ttggggtttc ccgaagctgg cgagttcctg aggccgacct cctttggcgc accggacact | 46020 |
| gtccggtgta caccggacag tccggtgaat tatagcgcga gtgcctctgg aaattcccga | 46080 |
| aggtggcgag tttgagtctg agtcccccctg gtgcaccgga cagtccggtg cgccagacca | 46140 |
| ggggtgcctt cggttgcccc tttgctcttt tgttgaatcc aaaactgggt ctttttattg | 46200 |
| gctgagtgtg aaccttttac acctgtgtaa tctatacact tgggcaaact agttagtcca | 46260 |
| attatttgtg ttgggcaatt caaccaccaa aattaattag ggactaggtg taagcctaat | 46320 |
| tccctttcaa tctcccccctt tttggtgatt gatgccaaca caaaccaaag caaatataga | 46380 |
| agtgcataat tgaactagtt tgcataatgt aagagtaaag gttgcttgga attgagccaa | 46440 |
| tgtaaatact tacaagatat gcagggattg tttctttctt atatattatt ttggaccacg | 46500 |
| cttgcaccac atgttttgtt tttgcaaatt cttttttgtaa atccatttca aagatctttt | 46560 |
| gcaaatggtc aaaggtaaat gaataagagt ttgcaaagca ttttcaagat ttgaaatttt | 46620 |
| ctcccccctgt ttcaaatgct tttcctttga ctaaacaaaa ctccccctaa aagagatcct | 46680 |

```
cctcttagtg ttcaagaggg ttttgatata tcattttttga aatactactt tctccccctt    46740
ttgaacacaa taggatacca attgataaat actcttggaa aacactaagt tttttgaaatt   46800 ggttgtggtg cggtcctttt tgctttgggc tcatactttc tccccctttg gcatgaatcg    46860
ccaaaaacgg aatcattaga gcctatcgaa gtactatcgt cccctttggt cataagtaaa    46920
tgagttaaga ttataccaaa gacgaaatcc ggtcttttag ctttgggttc ttactctctc    46980
cccaaagaca aggtccttta ttggagcgat ggcgaaggat gagttaccga gtggaagcct    47040
ttgtctttca ccgaagactc caattccctt tcaatatacc tatgacttgg tttgaaatag    47100
acttgaaaac acattagtca tagcatatat gattaaaagt ataaatgagc tatgtgtgca    47160
atctagcaaa agaagttgcg tgaatcaaga atattgagct catgcctaag tttggtaaaa    47220
gtttgttcat caagaggctt ggtaaagata tcggctaatt gatctttagt gttaatgtaa    47280
gaaatctcga tatcccccttt tgttggtga tccctaagaa aatgataccg aatggctatg    47340
tgcttagtgc ggctatgctc gacgggattg tcggtcattt tgattgcact ctcattatca    47400
catagcaaag ggactttggt taatttgtaa ccgtagtccc gcagggtttg cctcatccaa    47460
agcaattgcg cgcaacaatg acctgcggca atgtactcag cttcggcggt ggaaagagcg    47520
accgaatttt gcttctttga agcccaagac accaaagatc ttcccaagaa ctggcaagtc    47580
cctgatgtgc tcttcctatt aatttttgcac cccgcccaat cggcatccga ataaccaatc    47640
aaatcaaatg tggatccccg agggtaccaa agtccaaact taggagtata agccaaatat    47700
ctcaagattc gttttacggc cgtaaggtgg gattccttag ggtcggattg gaatcttgca    47760
cacatgcata cggaaagcat aatgtccggt cgagaagcac ataaatagag taaagaacct    47820
atcatcgacc ggtataacctt tgatccacg gacttacctc ccgtgtcgag gtcgagatgc    47880
ccattggttc ccatgggtgt cttgatgggc ttggcatcct tcattccaaa cttgcttaga    47940
atatcttgag tatactttgt ttggctaagg aaggtgccct cttggagttg tttgacttgg    48000
aatcctagaa aatacttcaa ctcccccatc atagacatct cgaatttctg tgtcatgatc    48060
ctactaaact cttcacatgt agactcgtta gtagacccaa atataatatc atcaacataa    48120
atttggcata caaacaagtc atttttcaaga gttttagtaa agagtgtagg atcggccttg    48180
ccgactttga agtcattagc aataaggaaa tctctaaggc attcatacca tgctcttggg    48240
ggcttgcttg agcccataaa gcgcctttga gagcctatag acatggttag ggtactcact    48300
atcttcaaag ccgggaggtt gctcaacata gacctcttcc ttgattggtc cgttgaggaa    48360 ggcactttttc acgtccattt gataaagctt aaagccatgg taagtagcat aggctaataa    48420
tattcgtatt gactcaagcc tagctacggg tgcataggtt tcaccgaaat ccaaaccttc    48480
gacttgggag tatcccttgg ccacaagtcg tgctttgttc cttgtcacca caccatgctc    48540
atcttgcttg ttgcggaaga cccatttggt ccctacaaca ttttgggtta ggacgtggaa    48600
ccaaatgcca tacctcattc ctcgtgaaat tgttgagctc ctcttgcatc gcccaccacc    48660
caatccgaat ctgaagtgct tcctctatcc tatgtggctc aatagaggaa acaaaagagt    48720
aatgctcaca aaaatgggca acacgagatc gagtagttac cccctatga atgtcgccga    48780 ggatggtgtc gacggggtga tctcgttgta ttgcttggtg gactcttggg tgtggcggtc    48840
ttggttcttc ctcatgctcc ttctcttgat catttgcatc tccccccttga tcattgtcat    48900 tatcttgagg tggctcatct tcttgatttt gcccttcatc aacttgagcc tcatcctcat    48960
tttgagttgg tggagatgct tgcgtggtgg aggatgattg atcttgtgca cttggaggct    49020
```

```
cttcggattc cttaggacac acatccccaa tggacatgtt ccttagcgct atgcatggag    49080
cctcttcatt acctatctca tcaagatcaa cttgctgtac ttgagagccg ttagtctcat    49140
caaacacaac gtcacatgag acttcaacta gtccagtgga cttgttaaag accctatatg    49200
cccttgtgtt tgagtcataa ccaagtaaaa agccttctac agttttagga gcaaatttag    49260
attttctacc tcttttaaca agaataaagc atttgctacc aaaaactcta agtatgaaa     49320 tgttgggctt tttaccggtt aggagttcat atgatgtctt cttgaggatt cggtgaagat    49380
ataaccggtt gatggcgtag caggcggtgt tgaccgctgc ggcccaaaac cggtccggtg    49440
tcttgtactc atcaagcatg gttcttgcca tgtccaatag agttcgattc ttcctctcca    49500
ctacaccatt ttgttgaggg gtgtagggag aagagaactc atgcttgatg ccctcctcct    49560
caagaaagcc ttcaatttgt gagttcttga actccgtccc gttgtcgctt cttatttct     49620 tgatccttaa gccgaactca ttttgagccc gtctcaagaa tcccttcaag gtctcttggg    49680
tttgagattt ttcctgtaaa aagaataccc aagtgaagcg agaataatca tccacaataa    49740
ctagacagta cttactcccg ccgatgctta tgtaagcaat cgggccgaat agatccatgt    49800
gtaggagctc cagtggcctg tcggtcgtca tgatgttctt gtgtggatga tgagctccaa    49860
cttgcttccc cgcctgacat gcgctacaaa tcctgtcttt ctcaaaatga acatttgtta    49920
atcctaaaat gtgttctccc tttagaagct tatgaagatt cttcatccca acatgggcta    49980
gtcggcggtg ccagagccaa cccatgttag tcttagcaat taagcatgtg tcgagttcag    50040
ctctatcaaa atctactaag tatagctgac cctctaacac acccttaaat gctattgaat    50100
cattacttct tctaaagaca gtgacaccta catcagtaaa aagacagttg tagcctattt    50160
gacataattg agaaacagaa agcaagttgt aatctaaaga atcaacaaga aaacattgga    50220
aatagaatgg tcaggagata tagcaatttt accaagtcct ttgaccaaac cttgatttcc    50280
atccccgaat gtgatagctc gttggggatc ttggtttttc tcatatgagg gaacattct    50340 tttctcccca gtcatatggt ttgtgcaccc gctgtcgagt atccaacttg agcccccgga    50400
tgcataaacc tacaaaacaa atttagttct tgactttagg tacccaaact gttttgggtc    50460
ctttggcatt agaaacaaga actttgggta cccaaacaca agtcttggaa cccttgtgtt    50520
tgcccccaac aaacttggca actactttgc cggatttgtt agtcaaaaca taggatgcat    50580
caaaagtttt aaatgaaata gcatgatcat ttgaagcatt aggagttttc tttctaggca    50640
acttagcacg ggttggttgc ctagaactag atgtctcacc cttatacata aaagcatggt    50700
tagggccaga gtgagacttc ctagaatgag ttctcctaat tttgctctca ggataaccgg    50760
cagggtacaa aatgtaaccc tcgttatcct gaggcatggg agccttgccc ttaacaaagt    50820
tggacaagtt cttaggaggg gcattaagtt tgacattgtc tcccctttgg aagccaatgt    50880
catccttaat gccggggcgt ctcccattat aaagcatgct acgagcaaat ttaaatttct    50940
cattctctaa gttgtgctcg gcaatttttag catctagttt tgttatatga tcattttgtt    51000
gtttaattaa agccatatga tcatgaatag catcaatatc aacatttta catctagtgc      51060 aaatagtgac atgctcaatg gtggatgtag atggtttgca agaattaagt tcaacaatct    51120
tagcacgaag tatatcattc ttatctctaa gatcagaaat tgtaattttg caaacatcaa    51180
aatctttagc cttagcaatt aaattttcat tttctaatct aaggctagca agagatacat    51240
tcaattcatc aatcttaaca agcaaatcaa cattatcatc tctaagattg ggaattgaaa    51300
catcaccaaa tatgtgaatc aaccttaa                                      51328
```

```
<210> SEQ ID NO 107
<211> LENGTH: 58
<212> TYPE: DNA
<213> ORGANISM: Zea mays

<400> SEQUENCE: 107
cactgtgcgt cctctgcagg cagttgttga catgagcgca tcgtcactgc tgaatcgc    58
```